(12) United States Patent
Allinson et al.

(10) Patent No.: US 10,159,451 B2
(45) Date of Patent: Dec. 25, 2018

(54) ASSEMBLY, APPARATUS, SYSTEM AND METHOD

(71) Applicant: University of Lincoln, Lincoln (GB)

(72) Inventors: Nigel Allinson, Lincoln (GB); Grainne Riley, Lincoln (GB); Chris Waltham, Lincoln (GB); Michela Esposito, Lincoln (GB); Tony Price, Birmingham (GB); Phil Allport, Liverpool (GB); Jon Taylor, Liverpool (GB); Gianluigi Casse, Liverpool (GB); Phil Evans, Guildford (GB); Gavin Poludniowski, Guildford (GB); Stuart Green, Birmingham (GB); Spyros Manolopoulos, Coventry (GB); Jaime Nieto-Camero, Faure (ZA); Marcus Verhoeven, Dresden (DE)

(73) Assignee: University of Lincoln, Lincoln (GB)

( * ) Notice: Subject to any disclaimer, the term of this patent is extended or adjusted under 35 U.S.C. 154(b) by 0 days.

(21) Appl. No.: 15/317,396

(22) PCT Filed: Jun. 9, 2015

(86) PCT No.: PCT/GB2015/051690
§ 371 (c)(1),
(2) Date: Dec. 8, 2016

(87) PCT Pub. No.: WO2015/189601
PCT Pub. Date: Dec. 17, 2015

(65) Prior Publication Data
US 2017/0120076 A1 May 4, 2017

(30) Foreign Application Priority Data

Jun. 9, 2014 (GB) .................................. 1410188.5
Jun. 9, 2014 (GB) .................................. 1410206.5
Jun. 9, 2014 (GB) .................................. 1410207.3

(51) Int. Cl.
*A61N 5/10* (2006.01)
*G01T 1/02* (2006.01)
(Continued)

(52) U.S. Cl.
CPC ............ *A61B 6/4266* (2013.01); *A61B 6/032* (2013.01); *A61B 6/4064* (2013.01);
(Continued)

(58) Field of Classification Search
CPC .......... A61N 5/10; A61N 5/1071; G01T 1/02; A61B 6/03; A61B 6/032
(Continued)

(56) References Cited

U.S. PATENT DOCUMENTS

2011/0220794 A1   9/2011 Censor et al.
2012/0292517 A1*  11/2012 Izaguirre ................. G01T 1/201
                                                          250/362

(Continued)

FOREIGN PATENT DOCUMENTS

DE      102 44 176 A1    4/2004
EP      0 421 869 A1     4/1991
(Continued)

OTHER PUBLICATIONS

Afanaciev et al, "Investigation of the radiation hardness of GaAs sensors in an electron beam," IOP Publishing Ltd and Sissa Medialab, Nov. 2012, pp. 1-11.
(Continued)

*Primary Examiner* — Nicole Ippolito
(74) *Attorney, Agent, or Firm* — Myers Bigel, P.A.

(57) ABSTRACT

Some embodiments of the present invention provide a 2D position-sensitive detector assembly comprising at least three substantially planar detector portions arranged in over-
(Continued)

lapping relationship as viewed normal to a plane of the detector portions, each detector portion comprising an array of substantially parallel, linear detector elements, the detector elements of respective detector portions being mutually non-parallel, the detector elements each being configured to generate one or more electrical signals in response to interaction of a particle of radiation therewith.

18 Claims, 36 Drawing Sheets

(51) Int. Cl.
    *A61B 6/03*     (2006.01)
    *A61B 6/00*     (2006.01)
    *G01T 1/29*     (2006.01)

(52) U.S. Cl.
    CPC .......... *A61B 6/4241* (2013.01); *A61B 6/4258* (2013.01); *A61N 5/1071* (2013.01); *A61N 5/1077* (2013.01); *G01T 1/02* (2013.01); *G01T 1/2928* (2013.01); *G01T 1/2985* (2013.01); *A61N 2005/1054* (2013.01); *A61N 2005/1085* (2013.01); *A61N 2005/1087* (2013.01)

(58) Field of Classification Search
    USPC ............................................. 250/396 R, 397
    See application file for complete search history.

(56) References Cited

U.S. PATENT DOCUMENTS

| | | | |
|---|---|---|---|
| 2013/0015352 A1* | 1/2013 | Karonis | ................ G01T 1/201 250/307 |
| 2017/0160211 A1 | 6/2017 | Schulte et al. | |

FOREIGN PATENT DOCUMENTS

| | | |
|---|---|---|
| EP | 1 124 129 A2 | 8/2001 |
| EP | 2 279 776 A2 | 2/2011 |
| EP | 2 634 601 A2 | 9/2013 |
| JP | 63-40381 A | 2/1988 |
| WO | WO 2011/100628 A2 | 8/2011 |
| WO | WO 2013/116709 A1 | 8/2013 |

OTHER PUBLICATIONS

Borchi et al., "The Compensation Condition in Hadron Calorimeters by the Filtering Effect," IEEE Transactions on Nuclear Science, vol. 37, No. 3, Jun. 1990, pp. 1186-1190.
Cirrone et al., "Monte Carlo Studies of a Proton Computed Tomography System," IEEE Transactions on Nuclear Science, vol. 54, No. 5, Oct. 2007, pp. 1487-1491.
Combined Search and Examination Report, GB Application No. 1410188.5, dated Dec. 18, 2014, 6 pages.
Combined Search and Examination Report, GB Application No. 1410206.5, dated Dec. 18, 2014, 8 pages.
Combined Search and Examination Report, GB Application No. 1410207.3, dated Dec. 12, 2014, 9 pages.
Furetta et al., "Large-Area Sandwich Calorimeter for Hadronic Calorimetry," IEEE Transactions on Nuclear Science, vol. 35, No. 1, Feb. 1988, pp. 446-450.
Hurley et al., "Water-equivalent path length calibration of a prototype proton CT scanner," Med. Phys. 39 (5), May 2012, pp. 2438-2446.
Kim et al., "Study on Proton Energy Measurement by Using a Si(Li) Detector Stack," Journal of the Korean Physical Society, vol. 54, No. 5, May 2009, pp. 2050-2054.
Menichelli et al., "Characterization of a Silicon Strip Detector and a YAG:Ce Calorimeter for a Proton Computed Radiography Apparatus," IEEE Transactions on Nuclear Science, vol. 57, No. 1, Feb. 2010, pp. 8-16.
Notification of Transmittal of the International Search Report and the Written Opinion of the International Searching Authority, or the Declaration, PCT/GB2015/051690, dated Aug. 31, 2015, 13 Pages.
Notification of Transmittal of the International Search Report and the Written Opinion of the International Searching Authority, or the Declaration, PCT/GB2015/051691, dated Aug. 31, 2015, 12 Pages.
Notification of Transmittal of the International Search Report and the Written Opinion of the International Searching Authority, or the Declaration, PCT/GB2015/051692, dated Aug. 31, 2015, 13 Pages.
Notification of Transmittal of the International Search Report and the Written Opinion of the International Searching Authority, or the Declaration, PCT/GB2015/052208, dated Oct. 16, 2015, 11 Pages.
Pensotti et al, "Experimental results form a sandwich calorimeter using U-absorbers and $0.25m^2$ of Si active area," European Organization for Nuclear Research, Geneva, Jul. 11, 1987, 16 pages.
Poludniowski et al, "Proton-counting radiography for proton therapy: a proof of principle using CMOS APS technology," Phys. Med. Biol., vol. 59, 2014, pp. 2569-2581.
Schulte et al, "Density resolution of proton computed tomography," Med. Phys., vol. 32, No. 4, Apr. 2005, pp. 1035-1045.
Schulte et al, "Design of a Proton Computed Tomography System for Applications in Proton Radiation Therapy," IEEE Nuclear Science Symposium. Conference, 2003, vol. 3, pp. 1579-1583.
Schulte et al., "Conceptual Design of a Proton Computed Tomography System for Applications in Proton Radiation Therapy," IEEE Transactions on Nuclear Science, vol. 51, No. 3, Jun. 2004, pp. 866-872.
Schulte et al., "Overview of the LLUMC/UCSC/CSUSB Phase 2 Proton CT Project," Trans Am Nucl Soc., 2012, vol. 106, 12 pages.
Simon, Frank, "Energy Reconstruction of Hadron Showers in the CALICE Calorimeters," IEEE Nuclear Science Symposium Conference Record, 2009, pp. 2292-2295.
Bruzzi et al., "Prototype Tracking Studies for Proton CT", IEEE Transactions on Nuclear Science, vol. 54, No. 1, Feb. 2007, pp. 140-145.
Bucciantonio et al., "Development of a fast proton range radiography system for quality assurance in hadrontherapy", Nuclear Instruments and Methods in Physics Research A, vol. 732, Dec. 2013, pp. 564-567.
Combined Search and Examination Report, GB Application No. 1413729.3, dated Mar. 11, 2015 (5 pages).
Cormack et al., "Quantitative Proton Tomography: Preliminary Experiments", Physics in Medicine & Biology, vol. 21, No. 4, Jul. 1976, pp. 560-569.
Cormack, "Representation of a Function by Its Line Integrals, with Some Radiological Applications", Journal of Applied Physics, vol. 34, No. 9, Sep. 1963, pp. 2722-2727.
Notification of Transmittal of the International Search Report and the Written Opinion of the International Searching Authority, or the Declaration, PCT/GB2015/052208, dated Oct. 16, 2015.
Pemler et al., "A detector system for proton radiography on the gantry of the Paul-Scherrer-Institute", Nuclear Instruments and Methods in Physics Research A, vol. 432, No. 2-3, Aug. 1999, pp. 483-495.
Rit et al., "Filtered backprojection proton CT reconstruction along with most likely paths", Medical Physics, vol. 40, No. 3, Mar. 2013, pp. 031103-1-031103-9.
Sadrozinski et al., "Detector Development for Proton Computed Tomography (pCT)", 2011 IEEE Nuclear Science Symposium Conference Record, Valencia, Spain, Oct. 23-29, 2011, pp. 4457-4461.
Sadrozinski et al., "Development of a head scanner for proton CT", Nuclear Instruments and Methods in Physics Research A, vol. 699, Dec. 2011, pp. 205-210.
Schulte et al. "Conceptual Design of a Proton Computed Tomography System for Applications in Proton Radiation Therapy", IEEE Transactions on Nuclear Science 51(3):866-872 (2004).
Schulte et al., "A maximum likelihood proton path formalism for application in proton computed tomography", Medical Physics, vol. 35, No. 11, Nov. 2008, pp. 4849-4856.

(56) References Cited

OTHER PUBLICATIONS

Sipala et al., "A proton Computed Tomography system for medical applications", 14th International Workshop on Radiation Imaging Detectors, Figueira da Foz, Portugal, Jul. 1-5, 2012 (published Feb. 12, 2013), 7 pp.

Suzuki et al., "Comparison between an image reconstruction method of filtering backprojection and the filtered backprojection method", Applied Optics, vol. 27, No. 14, Jul. 15, 1988, pp. 2867-2870.

Wang et al., "On the use of a proton path probability map for proton computed tomography reconstruction", Medical Physics, vol. 37, No. 8, Aug. 2010, pp. 4138-4145.

Williams, "The most likely path of an energetic charged particle through a uniform medium", Physics in Medicine & Biology, vol. 49, No. 13, Jul. 2004, pp. 2899-2911.

Zeng et al., "Can the Backprojection Filtering Algorithm by as Accurate as the Filtered Backprojection Algorithm", 1994 IEEE Nuclear Science Symposium and Medical Imaging Conference, Norfolk, VA, Oct. 30-Nov. 5, 1994, pp. 1232-1236.

\* cited by examiner

ASSEMBLY, APPARATUS, SYSTEM AND METHOD

RELATED APPLICATIONS

This application is a 35 U.S.C. § 371 national stage application of PCT Application No. PCT/GB2015/051690, filed on Jun. 9, 2015, which claims priority from Great Britain Patent Application No. 1410188.5 filed on Jun. 9, 2014, Great Britain Patent Application No. 1410206.5 filed on Jun. 9, 2014, and Great Britain Patent Application No. 1410207.3 filed on Jun. 9, 2014, the contents of which are incorporated herein by reference in their entireties. The above-referenced PCT International Application was published in the English language as International Publication No. WO 2015/189601 A1 on Dec. 17, 2015.

FIELD OF THE INVENTION

The present invention relates to apparatus for use in a range of applications involving the use of particles of radiation. In particular but not exclusively some embodiments of the present invention relate to apparatus for use in the treatment of patients receiving radiotherapy. Some embodiments of the present invention relate to apparatus for use in the treatment of cancer using protons or other charged hadrons although some embodiments may employ other radiation such as X-ray radiation.

BACKGROUND

Over 12 million new cancer cases are diagnosed worldwide each year. About 40% of all cancer patients receive radiation therapy as part of their curative treatment. Most types of radiotherapy use photons (X-rays or gamma-rays) or electron beams for the local treatment of disease. Ionizing radiation damages the DNA of tumour and healthy cells alike, triggering complex biochemical reactions that eventually result in prolonged abnormal cell function and cellular death.

The aim of radiotherapy treatment is to maximize the absorbed dose (and hence damage) to the target tumour and to minimize radiation-induced morbidity to adjacent healthy tissue. This is generally achieved by targeting a beam of radiation at the tumour area along a path that spares nearby critical and radiosensitive anatomic structures. In some known arrangements, multiple beams may be employed each travelling along a different path, the paths being arranged to cross one another in the tumour region. This has the advantage of avoiding overexposing the same healthy tissues. The total radiation dose to be delivered to a tumour may be partitioned into fractions over successive sessions. Because healthy tissues recover better and faster than malignant ones, with each radiotherapy session the accumulated cellular damage in the targeted tumour increases, whilst normal (non-tumour) tissues are given the opportunity to repair.

The absorbed dose of radiation as a function of depth in human tissue is illustrated in FIG. 1 for X-ray radiation of energy 4 MeV (trace T1), X-ray radiation of energy 20 MeV (trace T2) and proton radiation of energy 150 MeV (trace T3). It can be seen clearly from FIG. 1 that proton radiation exhibits the sharpest peak in energy deposited as a function of depth, and that a beam of energy 150 MeV is able to deposit a substantial amount of energy at a depth in the range corresponding to that of the tumour site, the depth being between depth d1 (around 10 cm) and depth d2 (around 12 cm) in the example of FIG. 1, with relatively low amounts of energy deposited at depths outside of this range.

When irradiating beams are composed of heavy charged particles (protons and other ions, such as carbon), radiation therapy is generally called hadrontherapy. If protons are used, radiation therapy may be called proton therapy. The strength of hadron therapy lies in the unique radiobiological properties of these particles. The particles can penetrate tissue, and hadrons deposit their maximum energy just before stopping within the tissue. This allows a precise definition of the specific region to be irradiated. The peaked shape of the proton (or hadron) energy deposition as a function of distance in the tissue is called the Bragg peak as indicated at BP in FIG. 1 and FIG. 2. FIG. 2 is a plot of deposited dose as a function of depth for proton beams of energy 50 MeV (trace T1), 150 MeV (trace T2) and 200 MeV (trace T3). With the use of protons and other hadrons, a tumour at a given depth can be subject to a substantial deposited dose of energy by means of protons or other hadrons whilst the damage to healthy tissues as a consequence of irradiation of the tissue is less than in the case when x-rays are employed as illustrated in FIG. 1.

The depth of tissue traversed prior to the depth at which the Bragg peak is found is set by the energy of the incident proton beam as illustrated in FIG. 2. The width of this peak can be moderated by manipulating the range of energies of the protons or other charged hadrons that comprise the irradiating beam.

It is to be understood that the Bragg peak occurs immediately before charged hadron particles come to rest. The peak in energy loss by a charged particle as it moves through a material occurs because the interaction cross section increases as the energy of the particle decreases.

It is to be understood that the position of the Bragg peak can be adjusted by means of an attenuator which absorbs a portion of the energy of a particle, or by modifying the properties of the particle accelerator. By varying the amount of attenuation in real time, the Bragg peak associated with an otherwise monoenergetic proton beam (exhibiting a relatively sharp Bragg peak) may be effectively widened over a given time period by increasing the range of energies, so that a larger volume of tissue (for example tumour tissue) can be treated. Real-time adjustment of the amount of attenuation can be achieved by movement of a variable thickness attenuator such as by rotation of a wedge-shaped attenuator forming part of a spinning wedge attenuator device.

As a consequence of the relatively sharp Bragg peak immediately prior to charged hadrons coming to rest, tissues closer to the surface of the body than the tumour site receive much reduced radiation when protons or other hadrons are employed, and therefore reduced damage. Tissues deeper than the tumour within the body receive very few hadrons, so that the hadron dose becomes immeasurably small.

The advantages of hadron therapy, such as proton therapy, through its ability to deliver very high doses into tumours with much reduced dose to neighbouring tissues, may include at least one of reduced probability of second cancers, increased ability to treat tumours adjacent to critical organs or structures, a reduction in overall treatment time, and improved quality of life for patients during and after treatment.

FIG. 3 is a schematic illustration of a known proton beam computerised or computed tomography (CT) scanner 100. The scanner 100 has first and second beam tracker structures 110, 120 and a calorimeter device 170, each of which is in communication with a computing device 190. The scanner 100 is arranged to allow a subject to be positioned between the first and second beam tracker structures 110, 120. A beam of protons 101B is projected towards the subject from a source (not shown) through the first beam tracker structure 110 to the subject 101S. Protons emerging from the subject 101S pass through the second beam tracker structure and into the calorimeter device 170.

The beam tracker structures 110, 120 each have a pair of mutually parallel beam position-sensitive detectors 110A, 110B, 120A, 120B configured to detect a location within a 2D X-Y plane defined by each detector 110A, 110B, 120A, 120B at which the beam 101B passes through the detector 110A, 110B, 120A, 120B. By knowing the position within the 2D planes defined by each of the detectors 110A, 110B of the first beam tracker structure 110 at which the beam 101B passes through the computing device 190 of the apparatus 100 is able to calculate a vector v1 defining the path of travel of the beam 101B from the source to the subject 101S.

Similarly, knowing the position within the 2D planes defined by the detectors 120A, 120B of the second beam tracker structure 120 at which the beam 101B passes through the detectors 120A, 120B the computing device 190 is able to calculate a vector v2 defining the path of travel of the beam 101B from the subject 101S to the calorimeter device 170.

The calorimeter device 170 is configured to measure the amount of energy contained in the beam 101B entering the device 170. The device 170 provides an output signal to the computing device 190 indicative of the amount of energy contained in the beam 101B at a given moment in time. In the example shown the calorimeter is a CsI-based scintillator calorimeter device 170.

The computing device 190 is configured to correlate measurement of vectors v1 and v2 with a measurement of the energy of the beam 101B as determined by the calorimeter device 170. It is to be understood that, based on a knowledge of the energy of protons incident on the subject 101S, the vectors v1 and v2 and the energy of the beam 101B emerging from the subject 101S, the computing device 190 is able to calculate an amount of proton energy absorbed by the subject 101S (i.e. the dose) at a given location within the subject 101S in a known manner.

In the scanner 100 shown in FIG. 3, the subject 101S is rotated about an axis A through the subject 101S parallel to the Y-axis as shown in FIG. 3. Proton intensity data is captured as a function of rotational position of the subject 101S about the A-axis, and the computing device 190 is able to build up a 3D image of the fraction of proton energy absorbed at a given 3D location within the subject 101S. The scanner 100 of FIG. 3 is a 'broad beam' scanner 100 in that the beam 101B is arranged to irradiate substantially continuously the area being imaged, in contrast to scanned beam systems in which the beam 101B is scanned in the X-Y plane.

Since different tissues exhibit different absorption characteristics, the internal structure of the subject's anatomy can be determined from the 2D images (radiographs) and 3D datasets built up from the 2D images captured as a function of rotational position of the subject 101S about axis A.

It is to be understood that, knowing the incident energy of a proton, and tracking it through the apparatus so as to determine its residual energy following passage through the tissue, allows an absorbed dose of proton radiation to be calculated. Additionally, tracking the paths of individual protons over a range of incident angles allows the reconstruction of the 3-dimensional volumetric CT image as described in further detail below. It is to be understood that measuring the energy of each proton and tracking the path of the proton so as to calculate where in the subject the proton lost its energy is important in some embodiments. This is because charged hadrons such as protons are typically relatively strongly scattered by the subject compared with X-rays. In contrast, in the case of X-ray CT scanner systems it is not necessary to measure the exit energy of each X-ray in order to generate a CT image of a subject.

The first proton CT experiment and reconstruction was performed in 1976 (A. M. Cormack and A. M. Koehler, "Quantitative Proton Tomography: Preliminary Experiments," Phys. Med. Biol. 21, 560-569, 1976). Little further development was made until about 2000, when the challenge of producing clinically viable proton CT was taken up. The Paul Scherrer Institute (Switzerland) published details of their system (P. Pemler, J. Besserer, J. de Boer, M. Dellert, C. Gahn, M. Moosburger, U. Schneider, E. Pedroni, H. Stauble, "A detector system for proton radiography on the gantry of the Paul-Scherrer-Institute," Nuclear Instruments and Methods in Physics Research A432:483-495, 1999)), which used single-layer segmented scintillating fibers and a range telescope constructed from closely-packed plastic scintillator plates. With only one plane of detectors before and after the object being investigated, they could only detect the position of an individual proton and not its direction. The use of scintillating plates in a range telescope for measuring proton beam energy post-passage through tissue meant that only one proton could be unambiguously detected at one time.

Loma Linda University, USA, developed a proton CT system having four x-y resolving silicon strip detectors, two positioned before the patient and two after, in a similar manner to that shown in FIG. 3. The range telescope was a Cesium Iodide-based scintillator calorimeter comprising 18 crystals with the resultant light detected by a photodiode connected to each crystal (H. F. W. Sadrozinski, V. Bashkirov, B. Colby, G. Coutrakon, B. Erdelyi, D. Fusi, F. Hurley, R. P. Johnson, S. Kashiguine, S. McAllister, F. Martinez-McKinney, J. Missaghian, M. Scaringella, S. Penfold, V. Rykalin, R. Schulte, K. Schubert, D. Steinberg, A. Zatserklaniy, "Detector Development for Proton Computed Tomography (pCT)", in Conference Proceedings of IEEE Nuclear Science Symposium and Medical Imaging Conference, 2011). The system was very slow, taking several hours to obtain one scan. The system also had limited energy resolution of the range telescope due to the use of a calorimeter and the thickness of strip detectors which perturb the proton beam. More recently, the same group announced the development of a second system, again using silicon strip detector pairs either side of the patient but with a range telescope having a stack of polystyrene scintillators (3 to 10) read out by photomultipliers (H. F.-W. Sadrozinski, R. P. Johnson, S. Macafee, A. Plumb, D. Steinberg, A. Zatserklyaniy, V. A. Bashkirov, R. F. Hurley, R. W. Schulte, "Development of a head scanner for proton CT," Nuclear Instruments and Methods in Physics Research A699:205-210, 2013). These systems suffer from limited energy resolution due to the use of a low number of scintillating planes in the range telescope and the use of relatively thick silicon strip detectors, which adversely affect the quality of the incident proton beams entering the patient. Moreover, the present applicant has recognized that the limitations of two conventional crossed x-y strip detectors will create a high proportion of false events. This is because with N events (protons) detected within one read cycle, there will be N(N−1) false events recorded.

A further system has been developed that apparently overcomes some of the range telescope limitations in terms of energy resolution by using 48 thin plastic scintillators coupled to silicon photon multipliers (M. Bucciantonio, U. Amaldi, R. Kieffer, F. Sauli, D. Watts, "Development of a Fast Proton Range Radiography System for Quality Assurance in Hadron therapy," Nuclear Instruments and Methods in Physics Research A: http://dx.doi.org/10.1016/j.nima.2013.05.110). As currently described the system is unsuitable for proton CT as no provision is made for positional detectors prior to the patient being imaged.

US2013/0015352A1 describes a proton computed tomography (pCT) detector system, including two tracking detectors in sequence on a first side of an object to be imaged, two tracking detectors in sequence on an opposite side of the object to be imaged, a calorimeter, and a computer cluster, where the tracking detectors include plastic scintillation fibers. All fibers in the detector system are read out by silicon photomultipliers.

A limitation of range telescopes which comprise of sheets of scintillator is that they are unable to distinguish between multiple protons passing through the sheets within the resolving time of the system, and there is no information provided about the location of the proton within the area of the sheet. Reducing the flux of protons to such a low level so that normally there is only one proton passing through the range telescope at one time, in order to compensate for this deficiency, means that the time to record a satisfactory CT image can be excessively long.

It is desirable to provide improved apparatus for delivery of radiotherapy treatment. It is an aim of the present invention to address disadvantages associated with the prior art.

SUMMARY OF THE INVENTION

Some embodiments of the present invention may be understood with reference to the appended claims.

Aspects of the present invention provide an assembly, an apparatus, a system and a method.

In one aspect of the invention for which protection is sought there is provided a 2D position-sensitive detector assembly comprising at least three substantially planar detector portions superimposed on one another with respect to a normal to a major plane of each detector portion, each detector portion comprising an array of substantially parallel, elongated strip elements, the strip elements of the respective detector portions being mutually non-parallel, the strip elements each being configured to generate one or more electrical signals in response to interaction of a particle therewith.

This feature has the advantage that a 2D position-sensitive detector assembly having reduced ambiguity in respect of determination of the number and location of protons passing through the detector portions may be provided.

It is to be understood that interaction of a particle of radiation may occur in the form of passage of a particle of radiation through a strip element or absorption of a particle of radiation by a strip element.

In one aspect of the invention for which protection is sought there is provided a 2D position-sensitive detector assembly comprising at least three substantially planar detector portions arranged in overlapping relationship as viewed normal to a plane of the detector portions, each detector portion comprising an array of substantially parallel, linear detector elements, the detector elements of respective detector portions being mutually non-parallel, the detector elements each being configured to generate one or more electrical signals in response to interaction of a charged particle of radiation therewith.

The charged particle may be a hadron such as a proton.

In a further aspect of the invention for which protection is sought there is provided a 2D position-sensitive detector assembly comprising at least three substantially planar detector portions arranged in overlapping relationship as viewed normal to a plane of the detector portions, each detector portion comprising an array of substantially parallel, linear detector elements, the detector elements of respective detector portions being mutually non-parallel, the detector elements each being configured to generate one or more electrical signals in response to interaction of a particle of radiation therewith.

This feature has the advantage that a 2D position-sensitive detector assembly having much reduced ambiguity in respect of determination of the number and location of particles of radiation passing through the detector portions such as charged hadrons, other particles or photons may be provided compared with known assemblies, commonly referred to as 'strip detectors'.

It is to be understood that interaction of a particle of radiation may occur in the form of passage of a particle of radiation through the detector element or absorption of a particle of radiation by the detector element.

The particle of radiation may be a quantum of radiation such as a photon, a hadron such as a proton, or any other suitable particle of radiation. It is to be understood that the particle may be considered to be a wavepacket. It is to be understood that reference to particle includes reference to a quantum of radiation such as a photon, charged hadron such as a proton, electron or other quantum of radiation.

Some embodiments of the present invention may be for detection of charged particles such as hadrons.

It is to be understood that by the term linear is meant that a physical layout or structure of the detector elements is linear. With regard to one or more electrical characteristics of a given detector element, in some embodiments the one or more electrical characteristics may be non-linear or linear.

It is to be understood that the detector portions may be arranged in overlapping relationship such that a notional line passing through one detector portion substantially perpendicular to a plane of the detector portion will also pass through each of the other detector portions. The detector portions may each be of similar or substantially identical size such that the detector portions substantially directly overlie one another in a substantially fully overlapping relationship.

Optionally, the linear detector elements of respective detector portions are oriented at substantially equal angles with respect to one another as viewed normal to a plane of the detector portions.

It is to be understood that reference to the plane of the planar detector portions is intended to be reference to the major plane of the detector portions.

The detector assembly may have only three substantially planar detector portions.

Optionally, the linear detector elements of respective detector portions are oriented at substantially 120 degrees with respect to one another.

It is to be understood that the linear detector elements may effectively enjoy a 2-fold axis of rotational symmetry being an axis normal to a plane containing the linear detector elements, through each detector element. That is, rotation of a linear detector element about this axis through 180 degrees results in the linear detector effectively having the same position in terms of the location of radiation sensitive detector area. Accordingly, linear detector elements oriented at substantially 120 degrees with respect to one another may also be considered to be oriented at substantially 60 degrees since the detectors are substantially coaxial about the axis about which each detector is rotated relative to the others.

It is to be understood that, in the case of known strip detector assemblies in which a pair of crossed (orthogonal) arrays of strips of semiconductor material are employed, the number of ambiguities for N hits per readout cycle (or read-time) is $N^2-N$. For example, for 5 actual hits in a given read-time for two orthogonal planes, there may be up to 20 ambiguities (400% higher).

Based on extensive simulations by the present applicant, three strip detector devices, with strip elements (with dimensions 100 um width and 50 mm length) oriented respectively along axes u, v, and x arranged at 120° to one another, will have an average ambiguity rate in respect of detection of the location and position of proton 'hits' will be only 0.6% at a read cycle of 40 ns.

Optionally, the detector portions each comprise a plurality of substrates each comprising an array of substantially parallel linear detector elements, respective detector elements of each of the plurality of substrates being substantially parallel and/or substantially collinear.

The plurality of substrates of a given detector portion may be substantially coplanar.

By way of example, in some embodiments a detector portion may have two or more substrates placed in a side by side relationship, with linear detector elements of each substrate parallel to respective linear detector elements of the other.

Alternatively, or in addition, two or more substrates may be placed in a side by side relationship with linear detector elements of one substrate being substantially collinear with those of the other. Other arrangements may also be useful.

This feature has the advantage that each respective substrate of the detector portion bearing an array of linear detector elements may be made smaller than in the case that a single substrate is employed to form a detector portion. This has the advantage that a manufacturing yield of devices may be increased. It is to be understood that, in the case of silicon processing technologies, manufacturing yields typically decrease with increasing circuit or device size. A further advantage is that the smaller overall area will increase the total number of particles that can be detected within a given read time at a specified ambiguity rate.

Optionally, each linear detector element comprises a strip or stripe element formed in or on a semiconductor substrate.

Methods of forming strip or stripe elements for silicon strip detectors are well known, and may be suitable for use in some embodiments of the present invention. Other types of linear detector element may be useful such as strip or stripe elements formed in semiconductor substrates other than silicon.

The detector assembly may comprise a gas ionization detector device.

The gas ionization detector device may comprise an array of conductive linear elements arranged to detect charged particles generated by ionization of gas comprised by the device.

The linear elements may be provided in a sealed environment of an ionizing gas or gas mixture, arranged wherein incident radiation creates a local ionization of the gas which in turn may be arranged to cause charge to be collected by one or more of the linear elements.

The gas ionization detector device may be a multi-wire proportional chamber device, a microstrip gas chamber, gas electron multiplier or any other suitable ionizing gas detector. The detector may have an array of 1D electrodes for detecting ionization of gas by hadrons.

The detector assembly may comprise a readout circuit portion configured to:
receive the one or more electrical signals generated by each linear detector element in response to interaction of one or more particles therewith, and
provide an output signal indicative of an identity of each linear detector element in which the one or more electrical signals have been generated.

It is to be understood that the readout circuit portion may be configured to determine that an electrical signal is a signal generated by a linear detector element in response to interaction of one or more particles therewith in dependence at least in part on a magnitude of the signal. In some embodiments the readout circuit portion may determine that an electrical signal is a signal generated by a linear detector element in response to interaction of one or more particles therewith if the magnitude of the signal exceeds a predetermined threshold value.

Optionally the readout circuit portion is configured to:
receive the electrical signals generated by a predetermined number of linear detector elements in substantially real-time over a predetermined readout period; and
provide the output signal indicative of the identity of the linear detector elements in which the electrical signal has been generated, and
the readout circuit portion being configured not to process further electrical signals generated by the predetermined number of linear detector elements until the output signal indicative of the identity of the linear detector elements in which the electrical signal has been generated has been provided.

Reference to being configured not to process further electrical signals is to be understood to mean that, once the readout circuit portion has received the electrical signals during the readout period, no further signals are received and/or processed until the next readout period begins. Thus the readout period refers to the period during which the readout circuit portion receives electrical signals from the detector portions, rather than the period during which the readout circuit portion outputs data processed by the readout circuit portion.

During the period between readout periods, the readout circuit portion may process data in respect of the electrical signals received, and provide the output signal indicative of the identity of the linear detector elements in which the electrical signal has been generated.

This feature has the advantage that a statistically significant data set in respect of the density distribution of particles over a cross-sectional area of a beam of particles of radiation may be generated, without a requirement to detect substantially continuously all particles passing through a detector assembly. Thus, the readout periods may be spaced apart over time and electrical signals generated by particles of radiation passing through the detector assembly may be captured by the readout circuit portion only during the readout periods. The readout periods may be spaced apart over time by periods dependent on the amount of time required to process the electrical signals received from the detector portions, and generate the output signals indicative of the identity of the strip elements in which the electrical signal has been generated. The period between readout periods may therefore be longer in some cases, where a relatively large number of signals are received in a given readout period.

It is to be understood that the length of the readout periods themselves may also be dependent on the number of electrical signals received by the readout circuit portion during a readout period. The readout circuit portion may terminate the readout period when a predetermined number of electrical signals have been received, for example when the readout circuit portion becomes saturated. Other arrangements may be useful in some embodiments.

It is to be understood that, if electrical signals indicative of detection of a particle are generated in a relatively large number of linear detector elements, the amount of time required to read out data indicative of the identity of the linear detector elements may take a longer period of time than in the case that electrical signals indicative of detection of a particle are generated in a relatively small number of linear detector elements. Accordingly, the time period between readout periods may be larger in the former case than in the latter case. However the present inventors have recognised that this is not necessarily a problem if a statistically significant number of readout periods can occur in a reasonable length of time.

Optionally, the readout period corresponds to one pulse period or an integer number of pulse periods greater than one, wherein a pulse period is a repetition period of pulses of radiation generated by a source of radiation.

The repetition period may for example be 1 millisecond, or any other suitable period.

The source may be any suitable source of radiation such as a cyclotron or a linear accelerator. The source may be configured to generate a beam of particles such as hadrons, optionally protons, with particles having an energy in the range from 50 MeV to 350 MeV.

It is to be understood that by reading out all hits over a given pulse period, P, and recording the total number of pulse periods, it is possible to form a good estimate of the integrated flux over a given time period even though the number of pulse periods for which data is read out may be unpredictable, and dependent on the flux.

Optionally the detector is configured to receive a timing signal indicative of a time at which a source of radiation generates a pulse of radiation.

The timing signal may be received from a controller associated with the source. Alternatively the timing signal may be generated by a controller associated with the detector assembly and provided to a controller associated with the source thereby to control the generation of pulses of radiation by the source.

Optionally the detector assembly is configured to provide an output indicative of the magnitude of the electrical signal generated in a detector element during a given readout period.

In some embodiments the readout circuit portion may comprise an analogue to digital converter portion for converting the magnitude of the electrical signal to a digital numerical value.

The detector assembly may be configured to provide an output indicative of an amount of electrical charge generated in a detector element in response to interaction with one or more particles of radiation during a given readout period.

The detector assembly may be configured to provide an output indicative of the number of particles contributing to generation of the electrical signal in a detector element during a given readout period.

It is to be understood that in some embodiments the electrical signal may have a magnitude that is dependent on the number of particles that interact with the linear detector element during a given readout period. However it is to be understood that, in the case of hadrons at least, the magnitude of the signal may depend at least in part on the energy of any particles such as hadrons interacting with a given linear detector element in a given readout period.

It is to be understood that the apparatus may produce a binary signal indicative that a given linear detector element has experienced a 'hit', i.e. an electrical signal corresponding to particle interaction with the linear detector element has been detected, or a signal indicative of the number of hits that have been experienced by a given linear detector element. For example, the signal may be a binary digital signal indicative of the number of hits, or a multi-level signal indicative of the number of hits.

In one aspect of the invention for which protection is sought there is provided apparatus comprising a first beam tracker structure and a second beam tracker structure and configured to allow passage of radiation through the first and second beam tracker structures, wherein the first and second beam tracker structures each comprise at least one detector assembly according to any preceding claim.

Optionally, the first and second beam tracker structures each comprise a pair of detector assemblies mutually spaced apart in a direction parallel to a direction of travel of radiation through the apparatus.

The apparatus may be configured to synchronise the readout period of the readout circuit portions of each detector assembly of the first and second beam tracker structures such that the readout periods begin at substantially the same time.

This feature has the advantage that passage of individual particles of radiation through the first and second beam tracker structures may be detected. Accordingly, in some embodiments, a trajectory or path of individual particles through the apparatus may be determined.

The apparatus may be configured to determine a direction of travel of individual particles of radiation through each of the beam tracker structures in dependence on detection of a location at which radiation passes through each detector assembly. In some embodiments the first beam tracker structure identifies the direction of the incident particle (on the patient) and the second beam tracker structure identifies the particle's exit direction from the patient.

The apparatus may be configured to:
determine a number of particles of a beam of radiation interacting with each of a plurality of linear detector elements of each detector portion of a detector assembly over a predetermined time period; and
provide an output indicative of a position and shape of the beam of radiation with respect to an active area of each detector portion in dependence on the number of particles interacting with each of said plurality of linear detector elements over the predetermined time period.

This feature has the advantage that characterisation of a beam of radiation interacting with the apparatus may performed. In some embodiments, the first beam tracker structure may be employed to monitor at least one of the position and shape of the beam and/or the flux of protons during treatment of a subject, i.e. during a period for which the beam energy has been set such that the Bragg Peak for proton absorption lies within the subject, thereby delivering a dose of proton beams to a site to be treated such as a tumour. It is to be understood that, under such conditions, relatively few (if any) protons may pass to the second beam tracker structure located downstream of the subject. The apparatus may be configured to correlate data in respect of the position and/or shape of the beam with data in respect of location of the region of the subject to be irradiated, to verify that the intended region is being irradiated. In addition or instead, beam flux of other measure of the number of particles may be monitored to verify that a required dose and/or dose rate is being employed at a given moment in time.

The apparatus may be configured to provide the output in the form of plots indicative of the number of particles of a beam of radiation that have interacted with each of the plurality of linear detector elements of each respective detector portion of a detector assembly.

This feature has the advantage that the apparatus may provide the output in a relatively rapid manner without a requirement to calculate (say) an (x,y) coordinate of each particle of radiation detected. It is to be understood that, because the output is indicative of the rate of detection of particles, the output may provide an indication of integrated flux.

The apparatus may be configured to provide the output in the form of plots indicative of the number of particles of a beam of radiation that have interacted with each of the plurality of linear detector elements of each detector portion of a detector assembly over a predetermined time period.

The predetermined time period may be a substantially fixed time period, giving a 'snap shot' of the number of particles interacting with each detector element in that time period. Alternatively or in addition the predetermined time period may be a period from a start time until a current time, the data (and plots) being repeatedly updated and the integrated flux of particles detected by each detector element displayed and updated in substantially real time.

Other arrangements may be useful in addition or instead in some embodiments.

The apparatus may comprise an energy resolving portion comprising at least one energy resolving portion detector element, the energy resolving portion being configured to measure an energy of particles that have passed through the first and second beam tracker structures.

The apparatus may be configured to measure a location at which a particle interacts with at least one energy resolving portion detector element.

The apparatus may comprise an energy resolving portion readout circuit portion configured to read out a location at which a particle interacts with the at least one energy resolving portion detector element during a readout period.

The apparatus may be configured to synchronise the readout period of the readout circuit portions of each detector assembly of the first and second beam tracker structures with the readout period of the energy resolving portion readout circuit portion.

This feature has the advantage that passage of individual particles through the first and second beam tracker structures, and subsequently the energy resolving portion, may be tracked.

It is to be understood that the readout periods of the readout circuit portions of each detector assembly of the first and second beam tracker structures may be substantially the same. The readout period of the energy resolving portion readout circuit portion may be different from the readout periods of the readout circuit portions of the detector assemblies of the first and second beam tracker structures. It is to be understood that the readout periods of the readout circuit portions of the detector assemblies of the first and second beam tracker structures may be much less than that of the energy resolving portion readout circuit portion.

In another aspect of the invention for which protection is sought there is provided a computerised tomography (CT) scanner apparatus comprising apparatus according to any preceding claim.

The apparatus may be configured to cause rotation of the first and second beam tracker structures with respect to a subject located therebetween.

The apparatus may be further configured to cause rotation of the energy-resolving portion with respect to a subject.

Optionally, the first and second beam tracker structures and the energy-resolving portion remain in substantially fixed orientation relative to one another when rotated with respect to a subject.

The apparatus may be configured to cause rotation of a subject with respect to the first and second beam tracker structures.

In an aspect of the invention for which protection is sought there is provided a system comprising apparatus according to a preceding aspect and a generator configured to generate radiation, the system being configured to deliver radiation from the generator to the apparatus.

The generator may be configured to generate pulses of radiation, the system being configured to synchronise by means of a timing signal the generation of pulses of radiation by the generator and the readout period of the readout circuit portion such that the readout period includes the period in which electrical signals are generated in the detector assembly in response to the pulses of radiation.

Optionally, the generator is configured to generate the timing signal or the apparatus is configured to generate the timing signal.

In one aspect of the invention for which protection is sought there is provided a method of detecting a particle of radiation comprising generating one or more electrical signals in a linear detector element of each of three substantially planar detector portions of a 2D position sensitive detector assembly in response to interaction of a common particle therewith, each detector portion comprising an array of substantially parallel, linear detector elements, the detector elements of respective detector portions being mutually non-parallel, the detector portions being arranged in overlapping relationship as viewed normal to a plane of the detector portions.

In a further aspect of the invention for which protection is sought there is provided apparatus for determining an energy of particles of radiation comprising:
  a plurality of solid state semiconductor detector devices provided at spaced apart locations along a direction of travel of a particle, the detector devices each being configured to generate an electrical signal indicative of passage of radiation through or absorption of radiation by the device; and
  at least one absorber portion provided upstream of at least one detector device with respect to a direction of travel of particles, the absorber portion being configured to absorb at least a portion of an energy of a particle,
  the apparatus being configured to provide an output signal in dependence on the electrical signals indicative of passage of radiation through or absorption of radiation by the detector devices.

In a still further aspect of the invention for which protection is sought there is provided apparatus for detecting particles of radiation comprising:
  a plurality of solid state semiconductor detector devices provided at spaced apart locations along a beam axis, the detector devices each being configured to generate an electrical signal indicative of passage of a particle through or absorption of a particle by the device; and at least one absorber portion configured to absorb at least a portion of an energy of a particle, wherein one said at least one absorber portion is provided in a particle path between at least one pair of adjacent detector devices, the apparatus being configured to provide an output signal indicative of the energy of a particle, the output signal provided being dependent on the electrical signals indicative of passage of a particle through or absorption of a particle by the devices.

It is to be understood that interaction of a particle of radiation may occur in the form of passage of a particle of radiation through the detector device or absorption of a particle of radiation by the detector device.

The particle of radiation may be a photon, a hadron such as a proton, or any other suitable particle of radiation. It is to be understood that the particle may be considered to be a wavepacket. It is to be understood that reference to particle includes reference to a quantum of radiation such as a photon, charged hadron such as a proton, electron or other quantum of radiation.

Some embodiments of the present invention may be suited to detection only of particles such as charged hadrons or electrons rather than with photons. Some embodiments may be suited to detection of charged hadrons such as protons and not to the detection of photons.

In one aspect of the invention for which protection is sought there is provided a computerised tomography (CT) scanner system for exposing a subject to hadron radiation, the system comprising apparatus for detecting particles of radiation that have passed through the subject, the apparatus comprising:

a plurality of detector devices, the plurality of detector devices comprising at least a first set of detector devices, the first set of detector devices comprising a plurality of solid state semiconductor detector devices provided at spaced apart locations along a beam axis, the detector devices each being configured to generate an electrical signal indicative of passage of a particle through or absorption of a particle by the device; and at least one absorber portion configured to absorb at least a portion of an energy of a particle, wherein one said at least one absorber portion is provided in a particle path between at least one pair of adjacent detector devices, the apparatus being configured to generate a signal indicative of the energy of a particle, the signal being dependent at least in part on the electrical signals indicative of passage of a particle through or absorption of a particle by a detector device.

In one embodiment, each detector device produces a binary signal indicative of the passage of a particle therethrough or absorption of a particle thereby when the amount of charge generated in the detector device by a particle exceeds a noise threshold. In some such embodiments, the indication of particle energy provided by the apparatus may be determined by reference to the number of detector devices generating a signal indicative of particle interaction therewith, whether passage therethrough or absorption thereby. This may then be related to the thickness and type of material that detected particles pass through before no longer being detected. Such apparatus may, accordingly, sometimes be referred to as a "range telescope", the range of travel of the particle as determined by the apparatus being indicative of particle energy.

It is to be further understood that, when a proton or other charged hadron comes near the end of its travel through a material, it typically loses relatively large amounts of energy relatively quickly, giving rise to the so-called "Bragg Peak" in energy absorption by a material close to the 'end of range' of the particle in the material. It is to be understood that in some embodiments the amount of charge generated in a detector device by a given particle may be responsive to the energy of the particle as it interacts with the detector device. The lower the particle energy, the greater the amount of energy lost by the particle as it interacts with the detector device, and the greater the amount of charge generated in the detector device. Accordingly, in some embodiments the energy of a particle may be inferred from an output signal that is indicative of the amount of charge generated by a particle in a given detector device.

Such apparatus has the advantage that detection of particle energy can be made in a relatively efficient manner since solid-state semiconductor detectors can enable highly reliable and efficient detection of particles. By providing an absorber portion between a pair of detector devices, an amount of energy of the particle may be reduced further as it travels from one detector device toward the next.

Knowledge of the absorption characteristic of each absorber portion can enable the amount of energy absorbed by an absorber portion to be calculated. The energy of a particle may be determined by determining the amount of energy absorbed by the one or more absorber portions, and any relevant detectors, through which the particle passes before it is no longer detected by a detector device downstream of the one or more absorber portions.

For example, in the case of an apparatus having first, second and third detector devices, a first absorber portion of known absorption characteristic may be provided between the first and second devices and a second absorber portion of known absorption characteristic may be provided between the second and third devices. If a particle is detected by the first and second detector devices but not the third detector device, it may be concluded that the energy of the particle was at least equal to that corresponding to the energy absorbed by the first and second detector devices and the first absorber portion, but less than that corresponding to the energy that would have been absorbed by the first, second and third detector devices and the first and second absorber portions if the particle had travelled through the first and second detector devices and generated an electrical signal in the third detector device.

In some embodiments, the amount of energy absorbed by the detector devices may be relatively small compared with that absorbed by the absorber portions, in which case the amount of energy absorbed by the detector devices themselves may be ignored in some arrangements.

Optionally, the detector devices are each operable to provide an output indicative of a 2D location with respect to a plane of each device at which a particle of radiation passed through or was absorbed by the device.

The output indicative of a 2D location may be an output indicative of a coordinate such as an (x, y) cartesian coordinate, or a range of possible coordinates. The range of possible coordinates may correspond to a pixel element location within a 2D array of pixel elements arranged in rows and columns. Alternatively the range of possible coordinates may correspond to an area such as an elongate linear area of a strip detector comprised by a detector device as described below.

The system may be configured to calculate a trajectory of a particle through the apparatus in dependence at least in part on the output, by each device through which a particle passed or in which a particle was absorbed, indicative of a 2D location with respect to a plane of each device at which a particle of radiation passed through or was absorbed by the device.

Optionally, the absorber portions each comprise one or more substantially planar absorber elements.

Optionally, the detector devices are provided in the form of substantially planar detector devices, and the detector devices are provided with a major plane thereof substantially normal to a direction of travel of particles through the apparatus.

Optionally, the apparatus further comprises a second set of detector devices, wherein the detector devices of the second set each comprise at least one substantially planar detector portion comprising an array of substantially parallel, linear detector elements each configured to generate one or more electrical signals in response to interaction of a particle of radiation therewith, wherein the substantially planar detector portions are provided with a major plane thereof substantially normal to a direction of travel of particles through the apparatus.

It is to be understood that, in some embodiments, employment of detector devices comprising linear detector elements has the advantage that such devices may have a lower readout period, enabling more rapid detection of passage of a proton. It is to be understood that the more rapid readout may be provided at the expense of reduced spatial resolution in terms of determination of the 2D location with respect to a plane of each device at which a particle of radiation passed through or was absorbed by the device. Nevertheless, a combination of detector devices of slower readout performance but higher spatial resolution (such as detector devices of the first set) with detector devices of reduced resolution but faster readout performance (such as detector devices of the second set) can enable an increase in the reliability with which proton path through the apparatus can be determined. This may in turn result in a reduction in the time required to acquire a given CT scan dataset.

Optionally, detector devices of the second set are each provided with at least one absorber portion configured to absorb at least a portion of an energy of a particle, wherein the at least one absorber portion is provided in a particle path between the detector device and an immediately adjacent detector device being a device of one of the first and second sets.

This has the advantage that energy may be absorbed by the absorber portion before it is incident on the detector device.

Optionally, the detector devices of the second set are interleaved with detector devices of the first set such that at least one detector device of the first set is provided between respective adjacent detector devices of the second set.

Optionally, respective adjacent detector devices of the second set are arranged wherein their respective arrays of substantially parallel, linear detector elements are mutually non-parallel.

Optionally, successive detector devices of the second set are arranged wherein longitudinal axes of their respective arrays of substantially parallel, linear detector elements are rotated through successively higher angles with respect to a detector device of the second set at or near a given end of the apparatus.

The successively higher angles may be arranged to increase by substantially the same amount from one device to the next, or by different amounts.

Optionally, the detector devices of the second set are arranged wherein successive detector devices have substantially the same angular difference between longitudinal axes of their respective arrays of substantially parallel, linear detector elements.

The angular difference between longitudinal axes may be substantially equal to (180/n) degrees where n is the number of detector devices of the second set. Thus in the case of 6 devices the angular difference may be substantially 30 degrees. Other angular differences may be useful in some embodiments.

The detector devices of the second set may each comprise at least two substantially planar detector portions arranged in overlapping relationship as viewed normal to a plane of the detector portions, longitudinal axes of the substantially parallel, linear detector elements of the respective detector portions of a given device being mutually non-parallel.

The angular difference between longitudinal axes of linear detector elements of the respective detector portions of a given device may be substantially equal to (180/n) degrees where n is the number of detector portions of each device. Other angular differences may be useful in some embodiments. Thus in the case of two detector portions the angular difference may be substantially 90 degrees, i.e. the linear detector elements of one portion may be substantially orthogonal to those of the other. In the case of three detector portions the angular difference may be substantially 60 degrees.

Optionally, the detector devices of the second set each comprise at least three substantially planar detector portions.

The detector devices of the second set may each comprise only three substantially planar detector portions, optionally with longitudinal axes at substantially 60 degrees to one another.

Optionally, the linear detector elements of each detector portion of the second set of detector devices comprise a doped strip or stripe element formed in or on a semiconductor substrate.

The strip or stripe element may be doped so as to form a p-n junction between the strip or strip element and the substrate in or on which the strip or stripe element is formed. Thus in the case of a p-doped substrate the strip or stripe element may be n-doped. Conversely, in the case of an n-doped substrate the strip or stripe element may be p-doped.

Each detector portion may comprise a semiconductor strip detector.

Optionally, each detector device of the second set comprises at least one gas ionization detector device.

Optionally, the gas ionization detector device comprises an array of conductive linear elements arranged to detect charged particles generated by ionization of gas comprised by the device.

Optionally, the linear elements are provided in a sealed environment of an ionizing gas or gas mixture, arranged wherein incident radiation creates a local ionization of the gas which in turn may be arranged to cause charge to be collected by one or more of the linear elements.

It is to be understood that the use of semiconductor strip detectors or gas ionisation detector devices has the advantage that detection of protons may be made relatively rapidly due to the lower readout periods of such detectors compared with CMOS photodiode arrays.

This feature has the advantage that in some embodiments the reliability with which the path of a given proton may be tracked through the apparatus may be increased. This may in turn enable a reduction in the amount of time required to obtain a given data set, such as given CT scan data set.

The apparatus may comprise a plurality of absorber-detector pairs, each absorber-detector pair comprising one of the at least one absorber portions and one of the detector devices, the absorber portion of a given pair being provided upstream of the detector device with respect to a direction of travel of particles through the apparatus.

The detector devices may be detector devices of the first and/or second sets.

Optionally, at least one absorber portion has a first absorption factor and at least one absorber portion has a second absorption factor different from the first.

By absorption factor is meant as the extent to which a medium is able to absorb energy from particles of radiation passing therethrough. In some arrangements, a water equivalent path length (WEPL) may be employed to characterise absorption factor, by which is meant the path length of a particle in water that would result in the same loss of energy as is caused by the at least one absorber portion. Other media may be used as a means for comparing absorption of radiation by a given material in addition or instead. By way of comparison, 200 MeV protons will travel 4 cm in lead, 8 cm in aluminium and 30 cm in water. Accordingly, 4 cm of lead has a WEPL of 30 cm.

Optionally, the at least one absorber portion having the first absorption factor and the at least one absorber portion having the second absorption factor are formed from materials of substantially the same absorption factor for a given thickness thereof, the second absorber portion having a different thickness to the first.

By reference to materials having substantially the same absorption factor for a given thickness is meant that, for samples of each material of substantially the same thickness (e.g. a thickness of 1 cm), the amount of energy absorbed from a particle of radiation such as a charged hadron, optionally a proton, would be substantially the same.

Optionally, the second absorption factor is less than the first.

Optionally, the absorber portion having the second absorption factor is provided downstream of a detector device that is itself downstream of the absorber portion having the first absorption factor.

This feature has the advantage that the resolution with which particle energy may be determined may be increased without increasing the number of detector devices required. It is to be understood that a larger reduction in particle energy may be effected by means of one or more absorber portions of the first absorption factor, and subsequently, a smaller reduction in particle energy effected by means of one or more absorber portions of the second absorption factor, when the particle is of lower energy and therefore more likely to be absorbed by an absorber portion. It is to be understood that the lower the absorption factor of the absorber portion between detector devices that is immediately downstream of the most downstream detector device that detects a particle, i.e. between that detector device and the next detector device downstream thereof, the greater the resolution with which particle energy may be determined. This is because in the worst case scenario where a particle passes through the detector device, causing the detector device to register the particle, the particle may travel through the next absorber element but, immediately before exiting the absorber element and entering the next detector device, the particle may be fully absorbed. Accordingly, the smaller the amount of energy absorbed by that absorber element, the lower the error in determining particle energy.

Therefore, the method may comprise providing absorber portions of lower absorption factor between respective detector devices downstream of one or more absorber portions of higher absorption factor, such that the most downstream detector device detecting a particle is immediately adjacent and upstream of an absorber portions of lower absorption power (or factor) than the one or more absorber portions of higher absorption power upstream thereof.

It is to be understood that a first absorber-detector pair may be provided that has a greater combined absorption factor than that of a second absorber-detector pair downstream of the first absorber-detector pair.

More than two absorber-detector pairs may be provided, each having a different absorption factor (or WEPL) from the others. Absorber-detector pairs of lower WEPL may be provided downstream of absorber-detector pairs of higher WEPL. Other arrangements may also be useful in some embodiments.

The first absorber-detector pair may have a greater absorption factor than each one of a plurality of absorber-detector pairs downstream of the first absorber-detector pair.

The system may be configured to determine the energy of a particle passing through at least a portion thereof in dependence at least in part on the identity of the most downstream detector device that generates an electrical signal indicative of passage of radiation through or absorption of radiation by the device.

Thus it is to be understood that the apparatus may be configured to determine the energy of the particle at least in part by identifying the most downstream detector device that detects the particle. The apparatus may be configured to calculate the amount of energy lost by the particle in dependence on the number of solid state semiconductor detector devices and the number of absorber portions (if any) through which the particle has travelled in order to reach the most downstream detector device detecting the particle.

It is to be understood that, equivalently, the energy of the particle may be determined in dependence on the identity of the detector device immediately downstream of the most downstream detector device that generates an electrical signal indicative of passage of radiation through or absorption of radiation by the device.

It is to be understood that in some embodiments the energy of particles passing through the apparatus may be varied in real time by means of a variable absorber element such as a rotating wedge-type device. This is so as to enable the Bragg peak of energy absorption in a subject such as a patient to be spread out in a direction along the direction of travel of radiation through the apparatus, enabling a larger volume of the subject to be subject to relatively high levels of radiation absorption at the end of range of the particles. The apparatus, or a system of which the apparatus forms part, may be configured to take into account variations in initial particle energy when determining the amount of energy absorbed by a particle. However, for a given particle, the distance travelled through the apparatus before the particle is absorbed may be employed to estimate particle energy.

In embodiments in which the absorber portions each comprise one or more substantially planar absorber elements, each absorber portion may comprise a plurality of elements, the plurality of elements defining a total thickness and therefore the absorption factor of the absorber element. The elements may be in the form of plates or plate-like elements. The absorber portions may therefore each comprise a plurality of elements such as plates of plate-like elements. The absorber portions may be of modular construction, comprising one or more elements, optionally coupled to one another to form an absorber portion. This feature has the advantage that absorber portions of different respective thicknesses may be provided in a convenient manner by use either of a single element, or an assembly of two or more elements.

It is to be understood that the apparatus may be configured to allow the absorber portions to be provided such that a normal to a plane of an absorber portion is substantially parallel to a beamline, and therefore the nominal direction of particle flux in the apparatus. It is to be understood that the actual trajectories of particles may deviate from a direction normal to a plane normal to the beamline due to scattering.

Optionally, the apparatus comprises means for introducing an absorber portion between respective adjacent detector devices or removing an absorber portion from between respective adjacent detector devices.

Optionally, the apparatus comprises means for introducing an absorber portion between respective adjacent detector devices or removing an absorber portion from between respective adjacent detector devices whilst the detector devices are in-situ.

By in-situ is meant that the absorber portion may be introduced between respective adjacent detector devices without disturbing the relative positions of respective adjacent detector devices. Thus in some embodiments the detector devices may remain installed in an apparatus such as a CT scanner apparatus whilst one or more absorber portions are inserted or removed. This has the advantage that alignment of detector devices, which may be critical for system operation, may be substantially undisturbed by insertion or removal of absorber portions or absorber elements.

Optionally, the means for introducing an absorber portion between respective adjacent detector devices or removing an absorber portion from between respective adjacent detector devices comprises sliding means for introducing or removing the absorber portion by sliding.

Optionally, the sliding means is configured to allow the absorber portion to be slid in a direction substantially parallel to the major faces thereof.

Optionally, the sliding means comprises a guide allowing an absorber portion to slide in contact with the guide into the apparatus to an installed position in which the absorber element is located between respective detector devices.

Optionally, the sliding means comprises a holder for holding an absorber element, the holder being supported by a guide allowing the holder to slide from an installed position, in which the holder supports an absorber element between respective detector devices, to an extended position, in which the apparatus allows an absorber element to be removed from the holder.

Optionally, the apparatus comprises one selected from amongst at least four absorber-detector pairs, at least six absorber-detector pairs, at least eight absorber detector pairs, and at least ten absorber-detector pairs.

Optionally, the apparatus comprises from three to one hundred absorber-detector pairs.

Optionally, at least one absorber portion is configured to allow an absorption factor thereof to be adjusted in-situ.

This feature has the advantage that the Bragg Peak in respect of absorption of radiation in the apparatus may be adjusted without a requirement to remove an absorber element or add an absorber element.

Optionally, at least one absorber portion is configured to allow an absorption factor thereof to be adjusted in-situ such that an amount of energy absorbed from a particle may be varied from at least one selected from around 2 MeV to around 5 MeV, from around 5 MeV to around 10 MeV, from around 10 MeV to around 20 MeV, and from around 20 MeV to around 50 MeV.

Optionally, at least one absorber portion is provided upstream of the detector devices.

Optionally, at least one absorber portion is configured to allow an absorption factor thereof to be adjusted in-situ is provided upstream of the detector devices.

Optionally, at least one absorber element is provided that is configured to absorb an amount of particle energy in the range from 1 MeV to 10 MeV.

Optionally, at least one absorber element is provided that is configured to absorb an amount of particle energy in the range from 2 MeV to 5 MeV.

Optionally, at least one absorber element is provided that is configured to absorb an amount of particle energy in the range from 5 MeV to 10 MeV.

The system may have a working or active cross-sectional area over which particles may pass through the detector devices and be detected thereby, in the range from 1 to 500 square centimeters, optionally in the range from 1 to 200 square centimeters.

Optionally, the detector devices of at least the first set are each configured wherein charge is generated therein in response to passage of a particle therethrough or absorption of a particle thereby, the detector devices being configured to provide an output indicative of the amount of charge generated therein in response to passage of a particle therethrough or absorption of a particle thereby.

This feature has the advantage that further information in respect of energy of a particle passing through a detector may be obtained as discussed above. It is to be understood that, for a particle of a given energy, the amount of charge generated in a detector device, which corresponds to the amount of energy absorbed by the detector device, may be dependent on the energy of the particle. The greater the energy of the particle, the smaller the amount of energy lost as the particle passes through the detector device. Accordingly, a peak in the amount of charge generated in a detector device may be indicative of the position of the Bragg Peak in particle absorption. It is recognised that some charged particles may not exhibit such behaviour.

It is to be understood that in some embodiments the detector devices may each be operable to provide an output indicative of a 2D location at which a particle of radiation passed through or was absorbed by the device, and an indication of the amount of charge generated in the device by the particle.

Optionally, the detector devices of the first set are each in the form of a two dimensional array or pixel elements, each pixel element being configured to generate an electrical signal in response to passage of radiation through or absorption of radiation by the pixel element.

Optionally, the apparatus is configured to generate a signal indicative of the pixel element of the detector devices of the first set in which an electrical signal is generated in response to passage of radiation through or absorption of radiation by the pixel element.

Optionally, the pixel elements of each detector device of the first set each comprise at least one photodiode device.

Optionally, the pixel elements of each detector device of the first set are provided on a single semiconductor substrate.

Optionally, the pixel elements of each detector device of the first set are distributed over a plurality of semiconductor substrates.

This feature has the advantage that the detector devices may be fabricated more cheaply in some embodiments. This is at least in part because a yield of semiconductor substrates (for example in the form of wafers) bearing pixel elements typically decreases with increasing wafer area. Two smaller semiconductor substrates may in some cases be provided more cheaply than a single substrate of similar size, the detector device being formed by combining the two smaller substrates.

In addition or instead, this feature may have the advantage that a rate at which electrical signals may be read out from the pixel elements of a given device may be increased in some embodiments. This is at least in part because separate readout electronics may be provided to process signals generated by the pixel elements of each substrate, allowing substantially parallel processing of the electrical signals from the pixel elements of the respective substrates. It is to be understood that, in order to increase the chances of detection of a given particle incident on a detector device, the plurality of substrates may be arranged to be provided substantially in abutment with one another, and with pixel elements provided close to adjacent, abutting edges of the respective substrates so as to reduce an amount of any dead area of the otherwise active area of the detector device, the dead area being an area substantially unresponsive to particle irradiation. Unless this precaution is taken, the otherwise active area of the device may have relatively large dead areas or regions that are in fact unresponsive to particle irradiation.

It is recognised that more than two semiconductor substrates may be used to make up the total effective active area in some embodiments.

Optionally, the apparatus is configured to read out the electrical signal indicative of passage of radiation through or absorption of radiation by the device at a rate in the range from around 500 frames per second to around 3,000 frames per second.

It is recognised that there may be advantages of devices that operate much faster than 3,000 frames per second.

By frame is meant data indicative at least in part of whether a particle has passed through or been absorbed by a given detector device over a given time period, the time period being given typically by the reciprocal of the frame rate. Thus at a frame rate of 1000 per second, the time period would be around 1 ms. It is to be understood that because of the unpredictable and non-linear trajectories of the particles as they pass through the layers and the need to identify the trajectories of individual particles then it is necessary that the number of particles detected in one frame time is relatively low. Hence, the frame rate needs to be high.

It is to be understood that by providing a plurality of substrates each bearing pixel elements and preferably with substantially parallel processing of electrical signals from the pixel elements, such relatively high frame rates may be achieved.

Optionally, the apparatus is configured to read out the electrical signal indicative of passage of radiation through or absorption of radiation by the device at a rate in the range from around 800 frames per second to around 1500 frames per second.

Optionally, the apparatus comprises a housing, wherein the absorber portions and detector devices are provided within the housing.

Optionally, the housing is configured to prevent passage of particles therethrough.

Optionally, the housing is configured to prevent passage therethrough of radiation generated by interaction of the particles with the apparatus.

Thus the housing may be configured to prevent passage therethrough of radiation that might be generated by the particles as they interact with the apparatus or the more general environment. A knowledge of the type of radiation and energy thereof will be sufficient to enable a designer to determine the required construction of the housing in order to ensure that substantially no such radiation is able to penetrate a wall of the housing.

Optionally, the apparatus comprises a plurality of detector modules configured to be coupled to one another, each detector module comprising a detector device.

Optionally, each detector module is configured to receive an absorber portion.

Optionally, each detector module comprises an absorber-detector pair.

Optionally, each detector module comprises only one absorber portion and only one detector device.

Optionally, the apparatus is a range telescope apparatus or energy discriminating apparatus.

The apparatus may be configured to calculate a trajectory of a particle through the apparatus in dependence at least in part on the output, by each device through which a particle passed or in which a particle was absorbed, indicative of a 2D location with respect to a plane of each device at which a particle of radiation passed through or was absorbed by the device.

It is to be understood that knowledge of the trajectory of each particle may enable the location within a subject at which a particle was scattered to be determined. This may enable radiographic images of a subject to be produced that have enhanced resolution compared with energy discrimination apparatus that does not allow the trajectory of a particle to be determined, such as a conventional calorimeter apparatus.

In an aspect of the invention for which protection is sought there is provided a method of computerised tomography whereby a subject is exposed to hadron radiation, the method comprising:

generating an electrical signal by means of one or more of a plurality of solid state semiconductor detector devices provided at spaced apart locations along a direction of travel of the particles, the electrical signal being indicative of passage of radiation through or absorption of radiation by the device; and causing absorption of at least a portion of an energy of the particle by means of at least one absorber portion provided upstream of at least one of the detector devices, the method comprising generating a signal indicative of the energy of a particle, the signal being dependent at least in part on the electrical signals indicative of passage of a particle through or absorption of a particle by a detector device.

The method may comprise generating an output signal indicative of the energy of the particle in dependence on the electrical signal.

Thus it is to be understood that the output signal may provide an indication of the energy of the particle, the output signal being generated in dependence on the electrical signal generated by each detector device. In some embodiments the output signal may be in the form of a signal directly indicative of the energy of the particle, for example in the form of a data stream or numerical value indicative of the energy. Alternatively the output signal may be indicative of whether or not a given detector device detected passage of a particle therethrough, from which the amount of energy of a given particle may be calculated. The output signal may indicate the 2D location within an active area of each detector device at which the particle of radiation passed through the detector device. In some embodiments the output signal may include an indication of the amount of charge generated in each detector device by the passage of a particle therethrough, optionally in addition the 2D location within the active area of each device at which the particle passed through the detector device.

The method may comprise generating a signal indicative of the energy of the particle in dependence on the electrical signal.

Optionally, generating an output signal indicative of the energy of the particle in dependence on the electrical signal comprises generating a signal indicative of the energy of the particle in dependence at least in part on the identity of the most downstream detector device that generates an electrical signal indicative of passage of radiation through or absorption of radiation by the device.

The method may involve generating the output signal indicative of the energy of the particle by identifying the most downstream detector device that detects the particle. The method may comprise calculating the amount of energy lost by the particle in dependence on the number of solid state semiconductor detector devices and the number of absorber portions (if any) through which the particle has travelled in order to enable detection by the most downstream detector device detecting the particle.

It is to be understood that, equivalently, generating the output signal indicative of the energy of the particle in dependence on the electrical signal may comprise generating the output signal in dependence on the identity of the detector device immediately downstream of the most downstream detector device that generates an electrical signal indicative of passage of radiation through or absorption of radiation by the device.

The method may comprise causing absorption of at least a portion of an energy of the particle by means of a plurality of absorber portions each absorber portion being provided between a respective pair of adjacent detector devices.

The method may comprise providing at least one absorber portion having a first absorption characteristic and at least one absorber portion having a second absorption characteristic wherein the at least one absorber portion having the second absorption characteristic has a different effective absorption length from the at least one absorber portion having the first absorption characteristic.

Thus the absorber portions may have different respective absorption characteristics, and therefore different respective absorption lengths. It is to be understood that reference to absorber portions having different respective effective absorption lengths is equivalent to reference to absorber portions having different respective absorption powers or different respective absorption factors. The greater the effective absorption length, the greater the absorption power or absorption factor.

By effective absorption length is meant the effective length of the absorber element with respect to a reference material having a known absorption characteristic. The absorber portions having the first and second absorption characteristics may be made from the same or different materials. However, because the absorber portions have different effective absorption lengths, they would absorb different respective amounts of energy from particles of a given energy passing therethrough.

Optionally, providing at least one absorber portion having a first absorption characteristic and at least one absorber portion having a second absorption characteristic comprises providing absorber portions formed from materials of substantially the same absorption characteristic per unit length, whereby the second absorber portion is of a different thickness from the first.

Optionally the at least one absorber portion having the second absorption characteristic has a lower effective absorption length than the at least one absorber portion having the first absorption characteristic.

The method may comprise providing the absorber portion having the second absorption characteristic downstream of a detector device that is itself downstream of the absorber portion having the first absorption characteristic.

This feature has the advantage that the resolution with which particle energy may be determined may be increased without increasing the number of detector devices required. It is to be understood that a larger reduction in particle energy may be effected by means of one or more absorber portions of the first absorption characteristic, and subsequently, a smaller reduction in particle energy effected by means of one or more absorber portions of the second absorption characteristic, when the particle is of lower energy and therefore more likely to be absorbed by an absorber portion. It is to be understood that the lower the absorption characteristic of the absorber portion immediately downstream of the most downstream detector device that detects a particle, the greater the resolution with which particle energy may be determined. Therefore, the method may comprise providing absorber elements of lower effective absorption length between respective detector devices such that the most downstream detector device detecting a particle is immediately adjacent and upstream of an absorber element of lower effective absorption length.

It is to be understood that the absorption power such as the WEPL of the absorber portions of the apparatus, and relative absorption power such as relative WEPL of respective absorber portions, may be selected such that a Bragg peak associated with particle absorption is located in the region of the absorber elements of lower or lowest absorption power or WEPL, enabling relatively precise determination of the amount of energy loss of particles that are absorbed at a location of the apparatus corresponding to the Bragg peak in particle absorption. The determination of the amount of energy loss may be made at least in part by reference to the amount of charge generated in a given detector device by radiation passing therethrough.

The method may comprise introducing an absorber portion between respective adjacent detector devices or removing an absorber portion from between respective adjacent detector devices.

The method may comprise introducing an absorber portion between respective adjacent detector devices or removing an absorber portion from between respective adjacent detector devices whilst the detector devices are in-situ.

By in-situ is meant that the absorber element may be introduced between respective adjacent detector devices without disturbing the relative positions of respective adjacent detector devices.

The method may comprise introducing an absorber portion between respective adjacent detector devices or removing an absorber portion from between respective adjacent detector devices comprises introducing or removing the absorber portion by sliding.

The method may comprise:
  removing a first absorber portion having the first effective absorption length from between respective adjacent detector devices, and
  replacing the first absorber portion with a second absorber portion having the second effective absorption length different from the first.

The method may comprise, whilst the detector devices are in-situ:
  removing a first absorber portion having the first effective absorption length from between respective adjacent detector devices, and
  replacing the first absorber portion with a second absorber portion having the second effective absorption length different from the first, whilst the detector devices are in-situ.

The method may comprise providing the detector devices in the form of substantially planar detector devices.

The method may comprise mounting the detector devices with a major plane thereof substantially normal to a direction of travel of particles.

The method may comprise providing at least a first set of the detector devices in the form of a two dimensional array or pixel elements, each pixel element being configured to generate an electrical signal in response to passage of radiation through or absorption of radiation by the pixel element.

The method may comprise providing the detector devices such that the pixel elements each comprise at least one photodiode device.

The method may comprise providing at least a second set of the detector devices each device of the second set comprising at least one substantially planar detector portion comprising an array of substantially parallel, linear detector elements each configured to generate one or more electrical signals in response to interaction of a particle of radiation therewith, the substantially planar detector portions being provided with a major plane thereof substantially normal to a direction of travel of particles through the apparatus.

The method may comprise providing detector devices of the second set with at least one absorber portion configured to absorb at least a portion of an energy of a particle, the method comprising providing the at least one absorber portion in a particle path between the detector device and an immediately adjacent detector device being a device of one of the first and second sets.

The method may comprise providing the detector devices of the second set interleaved with detector devices of the first set such that at least one detector device of the first set is provided between respective adjacent detector devices of the second set.

The method may comprise providing respective adjacent detector devices of the second set whereby their respective arrays of substantially parallel, linear detector elements are mutually non-parallel.

The method may comprise providing successive detector devices of the second set arranged whereby longitudinal axes of their respective arrays of substantially parallel, linear detector elements are rotated through successively higher angles with respect to a detector device of the second set at or near a given end of the apparatus.

The successively higher angles may be arranged to increase by substantially the same amount from one device to the next, or by different amounts.

The method may comprise providing detector devices of the second set arranged whereby successive detector devices have substantially the same angular difference between longitudinal axes of their respective arrays of substantially parallel, linear detector elements.

In one aspect of the invention for which protection is sought there is provided apparatus having a particle beamline for passage of charged particles of radiation therealong, comprising:
  a first beam tracker structure comprising at least one position sensitive detector (PSD) for determining a location with respect to a cross-sectional area of the beam line at which particles pass through the PSD;
  energy discrimination apparatus for determining an energy of particles that have passed through the first beam tracker structure; and
  support means for supporting a subject in a path of a particle along the beamline between the first beam tracker structure and the energy discrimination apparatus,
  the apparatus being configured to be operated in a selected one of a first mode and a second mode,
  the apparatus being configured, in the first mode of operation, to control an energy of the beam of charged particles passing through the first beam tracker structure such that a Bragg peak of charged particle absorption is located within the subject, and
  in the second mode of operation, to control an energy of the beam of charged particles passing through the first beam tracker structure such that a Bragg peak of charged particle absorption is located within the energy discrimination apparatus.

The charged particles may be hadrons, optionally protons.

In a further aspect of the invention for which protection is sought there is provided a computerised tomography (CT) system comprising apparatus according to the preceding aspect.

In one aspect of the invention for which protection is sought there is provided computed tomography (CT) apparatus arranged to employ a beam of hadrons to acquire hadron projection images of a subject at a plurality of respective beam angles with respect to the subject, the apparatus comprising a particle beamline for passage of charged particles of radiation therealong, the CT apparatus comprising:
  a first beam tracker structure comprising at least one position sensitive detector (PSD) for determining a location with respect to a cross-sectional area of the beam at which particles pass through the PSD;
  energy discrimination apparatus for determining an energy of particles that have passed through the first beam tracker structure; and
  support means for supporting a subject in a path of a particle along the beamline between the first beam tracker structure and the energy discrimination apparatus,
  the CT apparatus being configured to be operated in a selected one of a first mode and a second mode,
  the CT apparatus being configured, in the first mode of operation, to control an energy of the beam of hadrons passing through the first beam tracker structure such that a Bragg peak of hadron absorption is located within the subject and to provide an output indicative of a position of the beam passing through the first beam tracker structure in dependence at least in part on an output provided by the first beam tracker structure, and
  in the second mode of operation, to control an energy of the beam of hadrons passing through the first beam tracker structure such that a Bragg peak of charged particle absorption is located within the energy discrimination apparatus.

CT apparatus according to embodiments of the present invention has the advantage that a subject may be caused to absorb relatively high amounts of integrated energy (dose) when the apparatus is operated in the first mode, and a relatively small amount of integrated energy (dose) when operated in the second mode. Operation of the apparatus in the second mode may permit hadron projection images of the subject to be recorded in some embodiments.

The ability to record images of a subject (in the second mode) and in addition to being causing relatively high amounts of energy to be absorbed by a subject (in the first mode) using a single apparatus has a number of advantages. In the case that the apparatus is being used to cause absorption of particle energy by a feature within the subject that is distinguishable in an image of the subject from other features within the subject, an operator may first operate the apparatus in the second mode to confirm that the feature within the subject that is to be the subject of energy absorption is still present, and of the expected size and/or in the expected location, before operating the apparatus in the first mode whilst the subject remains present. Thus an operator may confirm a size and/or position and/or shape of the feature whilst the subject is subjected to relatively low amounts of energy absorption before and/or after subjecting the feature to relatively high amounts of energy absorption, for example as part of a radiotherapy programme.

It is to be understood that interaction of a particle of radiation may occur in the form of passage of a particle of radiation through the detector device or absorption of a particle of radiation by the detector device.

Some embodiments of the present invention may be suited to detection only of particles such as charged hadrons or electrons rather than photons. Some embodiments may be suited to detection of charged hadrons such as protons and not to the detection of photons.

Optionally the apparatus, when operated in the first mode, the apparatus is further configured to provide an indication of a flux of hadron particles comprised by the beam in dependence at least in part on the output provided by the first beam tracker structure.

This feature may enable an operator to monitor the flux of hadrons and ensure that the flux is within a predetermined tolerance. The flux, measured for example in particles per second per unit area, may be integrated over time and the area irradiated in order to enable a total dose to be calculated. Operation in the first mode may be terminated once the required dose has been reached.

Optionally, when operated in the first mode, the apparatus is further configured to provide an indication of a 2D intensity distribution of hadron particles comprised by the beam with respect to an active area of the first beam tracker structure.

The intensity distribution may comprise an indication of a cross-sectional shape of the beam. By active area is meant the area of beam tracker structure as viewed substantially parallel to a path of travel of hadrons through the apparatus.

It is to be understood that reference to beamline includes a path for travel of a beam of particles through or within the CT apparatus, as well as the components of the apparatus that define the path such as one or more beam tracker structures where more than one is provided, and energy discrimination apparatus where such apparatus is provided.

Optionally the first beam tracker structure comprises at least first and second PSDs at spaced apart locations along the beamline, each configured to determine a location with respect to a cross-sectional area of the beamline at which a given particle passes through the respective PSD, the second PSD being located downstream of the first with respect to the direction of travel of the beam along the beamline towards the subject.

This has the advantage that a trajectory of a particle passing through the first beam tracker structure may be determined. This is because in some arrangements the trajectory may be considered to correspond to a substantially straight path from a location at which the particle passes through the first PSD to a location at which the particle passes through the second PSD.

Optionally the at least first and second PSDs of the first beam tracker structure each comprise a plurality of strip detector devices, each strip detector device of each PSD comprising a plurality of substantially coplanar, mutually parallel strip elements each having a longitudinal axis, wherein the longitudinal axes of strips of the detector devices of a given PSD are non-parallel.

The first and second PSDs may each comprise a pair of crossed strip detector devices, being a pair that have longitudinal axes arranged substantially orthogonal to one another, in substantially parallel planes at spaced apart locations along the beam and substantially coaxial with respect to a notional longitudinal axis of the beamline.

The apparatus may further comprise a second beam tracker structure comprising at least one PSD, the second beam tracker structure being located in a path of particles along the beamline between the support means and the energy discrimination apparatus.

The presence of the second PSD has the advantage that a trajectory of a particle that has passed through the subject may be estimated at least in part based on particle position data obtained by means of the first and second beam tracker structures.

Optionally, the second beam tracker structure comprises at least first and second PSDs at spaced apart locations along the beamline each configured to determine a location with respect to a cross-sectional area of the beam line at which a given particle passes therethrough, the second PSD being located downstream of the first with respect to the direction of travel of the beam towards the subject.

The presence of a plurality of PSDs in the second beam tracker structure has the advantage that a trajectory of a particle passing through the second beam tracker structure may be determined. This enables a substantial increase in the accuracy with which a path of travel of a particle from the first beam tracker structure to the second beam tracker structure may be determined. This in turn enables a substantial increase in the accuracy with which a location within the subject at which scattering of the particle takes place may be determined.

Optionally, the at least first and second PSDs of the second beam tracker structure each comprise a plurality of strip detector devices, each strip detector device of each PSD comprising a plurality of substantially coplanar, mutually parallel strip elements each having a longitudinal axis, wherein the longitudinal axes of strips of the detector devices of a given PSD are non-parallel.

The apparatus may be configured wherein in the first mode a mean average energy of hadrons passing through the first beam tracker structure is in a first range of energies, and in the second mode a mean average energy of hadrons passing through the first beam tracker structure is in a second range of energies different from the first, the mean average energy of hadrons in the second mode being higher than the mean average energy of hadrons in the first mode.

The apparatus may be configured to operate in a dual energy mode in which the scanner apparatus operates in the first and second modes substantially simultaneously, wherein the dual energy mode the beam passing through the first beam tracker structure consists substantially of a first portion of hadrons and a second portion of hadrons, wherein the first portion of hadrons passing through the first beam tracker structure has a Bragg peak of hadron absorption that is located within the subject and the second portion of hadrons passing through the first beam tracker structure has a Bragg peak of hadron absorption located within the energy discrimination apparatus.

The first portion of hadrons may be arranged wherein the Bragg peak of particle absorption is at a predetermined location within the subject corresponding to a site to be treated. The second portion of hadrons may be arranged to irradiate the subject over a larger area than the first portion in order to enable data in respect of particle absorption character of the subject to be obtained as a function of the location at which particles pass through the subject, as viewed along a path of travel of the beam from the first beam tracker structure to the subject. That is, 2D absorption images may be obtained using the second portion of the beam.

The flux (particles per unit area per unit time) of particles forming the first portion of the beam, within an area defined by the beam, when the apparatus is operated in the dual energy mode (or of the particles that form the beam when the apparatus is operated only in the first mode), may be higher per unit cross sectional area of the beam than those forming the second portion of the beam when the apparatus is operated in the dual energy mode (or the particles that form the beam when the apparatus is operated in the second mode). This is at least in part so as to reduce exposure of the subject to higher energy particles having a Bragg peak of particle absorption in the energy discrimination apparatus, whilst still enabling useful spatial tissue data to be obtained in respect of the subject. Furthermore, particle path through the apparatus may be determined more reliably (with less uncertainty) at lower beam fluxes. It is to be understood that an ability to obtain spatial tissue data, such as spatial tissue density data, may enable the apparatus to ensure that a particular region of the patient of interest is being subject to particle absorption.

The present apparatus may also enable a user to determine whether the region of the subject that is required to be subject to particle absorption has moved with respect to the apparatus, for example due to movement of a patient's head, or changed shape or size. It is to be understood that a region being subject to particle absorption may be a region occupied by cancerous cells such as a brain tumour. The tumour may decrease in size over time and therefore the volume of the region of the subject that is to be subject to particle absorption may decrease, and/or the shape may change.

It is to be understood that the respective spatial areas or volumes swept by the first and second portions of the beam pass may be overlapping, optionally substantially the same areas or volumes. The spatial volume swept by the first portion may be within the volume swept by the second portion.

Optionally, the first energy range is substantially from a first lower energy value to a first upper energy value and the second energy range is substantially from a second lower energy value to a second upper energy value.

It is to be understood that when the apparatus is operated in the first mode, one or more beam shaper elements may be employed to adjust the spatial energy distribution of hadrons for which the Bragg peak of charged particle absorption is located within the subject. The one or more beam shaper elements may be arranged substantially to block charged particles that will not irradiate the target area to be irradiated. The one or more beam shaper elements may be arranged to adjust the energy of particles that will irradiate the target area of interest such that the Bragg peak of particle absorption takes place within the volume of interest. The one or more beam shaper elements may control the lateral shape or extent of the beam being the shape or extent normal to a nominal direction of travel of the beam through the apparatus, i.e. as viewed along the nominal direction of travel, which may be described as a direction 'along the beamline'.

Optionally, the second lower energy value is greater than the first lower energy value and the second higher energy value is greater than the first higher energy value.

Other arrangements may be useful.

The apparatus may comprise means for adjusting the position of the Bragg peak of particle absorption by adjusting an amount of energy absorbed by the apparatus upstream of the first beam tracker structure, optionally in substantially real time whilst a subject is subjected to a flux of particles.

The means for adjusting the position of the Bragg peak may allow real-time adjustment of the position of the Bragg peak of beams forming the first portion of the beam in embodiments operated in the dual mode, or of the beam when the apparatus is operated in the first mode, to allow variation in the depth at which the Bragg peak occurs in the subject.

The apparatus may comprise means for introducing and removing one or more absorber elements upstream of the first beam tracker structure, wherein a position of a Bragg peak of particle absorption may be adjusted.

Optionally, the means for adjusting the position of the Bragg peak of particle absorption comprises means for adjusting an absorption characteristic of one or more adjustable absorber devices of the apparatus.

One or more adjustable absorber devices of the apparatus may each comprise a wedge-type adjustable absorber device. One or more of the adjustable absorber devices may comprise a wedge-shaped attenuator. One or more of the adjustable absorber devices may comprise a spinning wedge attenuator device.

Other adjustable absorber devices may be useful.

The apparatus may comprise a blocking absorber element downstream of the subject support means for substantially preventing particles from being detected by the energy discrimination apparatus.

Optionally, the energy discrimination apparatus is further configured to allow a trajectory of a particle to be determined.

Optionally, the energy discrimination apparatus comprises a plurality of PSDs at spaced apart locations with respect to the beamline, each configured to detect a particle passing along the beamline through the energy discrimination apparatus.

The PSDs of the energy discrimination apparatus may be of a type similar to that of the first beam tracker structure. Alternatively the PSDs of the energy discrimination apparatus may be of different type. The PSDs of the energy discrimination apparatus may comprise CMOS detector devices, optionally CMOS detector devices comprising pixel elements each comprising a photodetector or photodetectors such as photodiodes.

The apparatus may comprise mode selection means for allowing a user to select operation of the apparatus in the first mode or the second mode.

The mode selection means may comprise a user interface of a computing apparatus, optionally a graphical user interface.

Optionally, the mode selection means is configured to allow a user to select operation of the apparatus in the dual energy mode.

The apparatus may comprise mode selection means for allowing a user to select operation of the apparatus in the dual energy mode.

The apparatus may be configured automatically to adjust the position of the Bragg peak of particle absorption in dependence on the selected mode.

It is to be understood that the apparatus may be configured automatically to adjust the position of the Bragg peak using the means for adjusting the position of the Bragg peak of particle absorption.

The apparatus may comprise computing apparatus configured to control the first beam tracker structure to detect a position of a particle by means of the at least one PSD and to determine an energy of a particle by reference at least in part to data output by the energy discrimination apparatus.

Optionally, the computing apparatus is further configured to control the second beam tracker structure to detect a position of a particle by means of the at least one PSD thereof.

Optionally, the subject support means comprises means for rotating a subject about an axis substantially normal to a trajectory of the beam at the location at which the beam passes through the subject.

The apparatus may comprise means for rotating the beamline about an axis substantially normal to the beamline at the location at which the beamline passes through the subject.

In a further aspect of the invention for which protection is sought there is provided apparatus according to a preceding aspect in combination with means for generating a beam of hadrons.

Optionally, the means for generating a beam of hadrons comprises means for generating a beam of protons.

The apparatus may be further configured to generate tomographic CT image data based on the acquired hadron projection images.

The apparatus may be configured to allow a user to select a location of a subject at which a tomographic image of the subject is required to be viewed, and to display a tomographic image of the subject at the selected location based on stored image data that has been acquired by the apparatus.

In one further aspect of the invention for which protection is sought there is provided a CT system comprising apparatus according to a preceding aspect and means for generating a beam of hadrons.

In one aspect of the invention for which protection is sought there is provided a method of computed tomography (CT) implemented by means of a CT apparatus comprising:
  causing a beam of hadrons to pass along a beamline;
  measuring by means of a position sensitive detector (PSD) of a first beam tracker structure a location with respect to a cross-sectional area of the beam line at which particles pass through the PSD;
  determining by means of energy discrimination apparatus an energy of particles that have passed through the first beam tracker structure; and
  supporting a subject in a path of a particle along the beamline between the first beam tracker structure and the energy discrimination apparatus,
  the method comprising, in a first mode of operation, controlling an energy of the beam of charged particles passing through the first beam tracker structure such that a Bragg peak of charged particle absorption is located within the subject and providing an output indicative of a position of the beam passing through the first beam tracker structure in dependence at least in part on an output provided by the first beam tracker structure, and
  in a second mode of operation, controlling an energy of the beam of charged particles passing through the first beam tracker structure such that a Bragg peak of charged particle absorption is located within the energy discrimination apparatus and, whilst operating in the second mode of operation, acquiring at least one hadron projection image of the subject at each of a plurality of respective beam angles with respect to the subject.

It is to be understood that, in some embodiments of the apparatus, the apparatus may be configured to obtain at least one hadron projection image at each of a plurality of beam angles whilst in the second mode, the apparatus being operated in the first mode before or after acquiring each respective image whilst being operated in the second mode. In other words, the apparatus may alternate between operation in the first mode and operation in the second mode at each of a plurality of beam angles.

In an aspect of the invention for which protection is sought there is provided apparatus having a particle beamline for passage of charged particles of radiation therealong, comprising:
  first and second beam tracker structures each configured for determining a trajectory of particles passing therethrough along the beamline;
  support means for supporting a subject in a path of a particle along the beamline between the first and second beam tracker structures; and
  energy discrimination apparatus for determining an energy of particles that have passed through the first and second beam tracker structures,
  the apparatus comprising means for selecting operation in one of a first mode and a second mode,
  in the first mode the apparatus being configured such that an energy of charged particles passing through the subject is in a first range of energies, and
  in the second mode the apparatus being configured such that an energy of charged particles passing through the subject is in a second range of energies different from the first,
  in use, with a subject supported by the support means, the first range of energies being selected such that a Bragg peak of charged particle absorption is located within the subject, and the second range of energies is selected such that a Bragg peak of charged particle absorption is located within the energy discrimination apparatus.

In a further aspect of the invention for which protection is sought there is provided apparatus having a particle beamline for passage of charged particles of radiation therealong, comprising:
  a first beam tracker structure configured for determining a trajectory of particles passing therethrough along the beamline;
  energy discrimination apparatus for determining an energy of particles that have passed through the first beam tracker structure; and support means for supporting a subject in a path of a particle along the beamline between the first beam tracker structure and the energy discrimination apparatus, the apparatus being configured to allow operation in a first mode and a second mode, in the first mode the apparatus being configured such that an energy of charged particles passing through the first beam tracker structure is in a first range of energies, and in the second mode the apparatus being configured such that an energy of charged particles passing through the first beam tracker structure is in a second range of energies different from the first, in use, with a subject supported by the support means, the first range of energies being selected such that a Bragg peak of charged particle absorption is located within the subject, and the second range of energies is selected such that a Bragg peak of charged particle absorption is located within the energy discrimination apparatus.

In one aspect of the invention for which protection is sought there is provided apparatus having a particle beamline for passage of charged particles of radiation therealong, comprising:

a first beam tracker structure comprising at least one position sensitive detector (PSD) for determining a location with respect to a cross-sectional area of the beam line at which particles pass through the PSD;

energy discrimination apparatus for determining an energy of particles that have passed through the first beam tracker structure; and support means for supporting a subject in a path of a particle along the beamline between the first beam tracker structure and the energy discrimination apparatus, the apparatus being configured to be operated in a selected one of a first mode and a second mode, in the first mode the apparatus being configured such that an energy of charged particles passing through the first beam tracker structure is in a first range of energies, and in the second mode the apparatus being configured such that an energy of charged particles passing through the first beam tracker structure is in a second range of energies different from the first, in use, with a subject supported by the support means, the first range of energies being selected such that a Bragg peak of charged particle absorption is located within the subject, and the second range of energies is selected such that a Bragg peak of charged particle absorption is located within the energy discrimination apparatus.

In one aspect of the invention for which protection is sought there is provided a computerised tomography (CT) system comprising an energy discrimination apparatus for determining an energy of particles that have passed through a subject, the system being configured to operate in first or second modes of operation in dependence on a selection by a user, wherein in the first mode of operation the system is configured to control an energy of a beam of particles of radiation such that a Bragg peak of particle absorption is located within a subject, and in the second mode of operation the system is configured to increase the energy of the beam of particles of radiation passing through the subject such that a Bragg peak of particle absorption is located within the energy discrimination apparatus, in the second mode the system being configured to capture image data in respect of the subject.

In the second mode the system may be configured to capture image data in respect of the subject thereby to enable CT data in respect of the subject to be generated.

Within the scope of this application it is envisaged that the various aspects, embodiments, examples and alternatives, and in particular the individual features thereof, set out in the preceding paragraphs, in the claims and/or in the following description and drawings, may be taken independently or in any combination. For example features described in connection with one embodiment are applicable to all embodiments, unless such features are incompatible.

For the avoidance of doubt, it is to be understood that features described with respect to one aspect of the invention may be included within any other aspect of the invention, alone or in appropriate combination with one or more other features.

BRIEF DESCRIPTION OF THE DRAWINGS

One or more embodiments of the invention will now be described, by way of example only, with reference to the accompanying figures in which.

DETAILED DESCRIPTION

Figure 1:
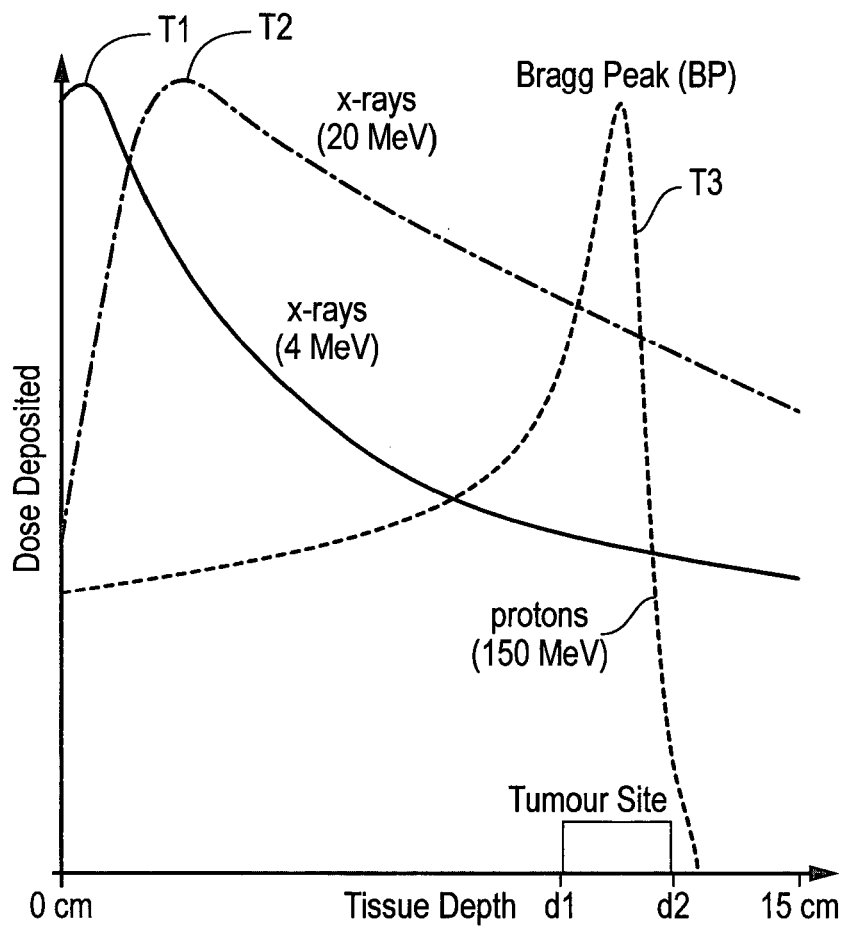
FIG. 1 is a plot of absorbed dose for different radiation types as a function of depth in human tissue.
Figure 2:
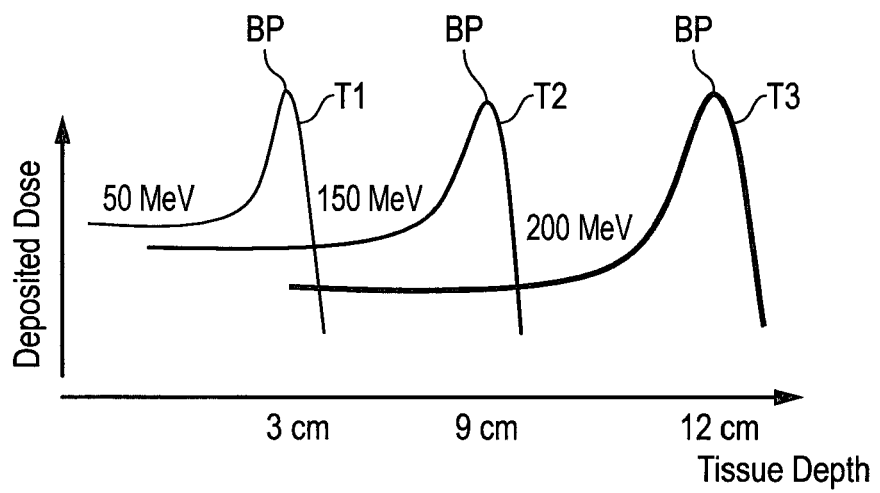
FIG. 2 shows the absorption profile of protons at three respective different energies.

The present inventors have conceived a number of desirable features in respect of apparatus for monitoring, assessing and recording the delivery of proton therapy treatments.

The first desirable feature is a quality assurance feature or mode in which it is ensured that a dose of radiation actually delivered to a subject corresponds to the desired dose. In some embodiments of the present invention, in order to provide this assurance, one or more tests may be conducted as part of a regular non-patient-specific general quality assurance programme in the form of a variety of periodic, such as daily, weekly, monthly and/or quarterly, measurements of the intensity of radiation generated by or passing through a proton beam CT scanner apparatus. Further measurements may be undertaken immediately prior to exposure of a subject in a treatment session to confirm that the dose to be delivered will match the required dose as well as confirming correct operation of the scanner apparatus.

A second desirable feature is an in-treatment monitoring feature or mode. For example, in some embodiments of the present invention a set of measurements may be made and an analysis conducted during patient treatment delivery to confirm that a proton therapy treatment is being delivered as planned, within a desired tolerance. In some embodiments, the primary requirements of this feature or mode of operation are: (i) to provide a record of what dose of particles has been delivered to the patient (in comparison to what was planned) and (ii) to provide a real-time warning if the delivered treatment in terms of dose being delivered is out of tolerance with that planned, allowing a cessation of treatment.

A third desirable feature is to enable a patient tissue imaging feature or mode, by which is meant radiographic (2D) and/or CT (3D) imaging utilizing a proton beam. Images of patient tissue obtained may be used for the guidance of treatment, for treatment planning purposes, and/or progress of treatment. Tissue imaging functionality may provide several functions to the user, replacing or complementing conventional x-ray imaging for radiotherapy. Distinct uses for such imaging include: (i) treatment planning using proton (or other hadron) beam CT scans, enabling 3D images to be established that enable clinicians to identify areas of tissue that are to be targeted for hadron absorption; proton or other hadron CT scans may be used in conjunction with other imaging modalities (e.g., x-ray CT and/or magnetic resonance imaging (MRI)); (ii) monitoring post-treatment changes in tissue by performing proton or other hadron beam CT scans in order to obtain 2D or 3D image data, information in respect of which may be used to alter a planned course of treatment if necessary, and (iii) intra-treatment imaging (both projection radiography and CT) for image-guidance, ensuring the desired area of tissue is being treated.

An example of a workflow might be as follows:
(a) A patient attends a proton facility prior to treatment and a proton CT scan is acquired using proton therapy apparatus according to an embodiment of the present invention, and data obtained as part of the scan is used to reconstruct a 3D image of the region of interest of the subject.
(b) The proton CT scan is subsequently exported to a treatment planning system.
(c) A treatment plan is developed for the patient using the proton CT scan in conjunction with other imaging modalities.
(d) The treatment plan is exported back to the proton therapy apparatus.

In the in-treatment monitoring and quality assurance aspects, the proton beam energy might typically be between 50 MeV and 350 MeV with beam fluxes ranging from $10^7$ to $10^9$ particles/cm$^2$/s and a beam diameter of several cm. Here, we refer to beam currents, which are normally measured by an ion chamber inserted into a beam delivery system just prior to the beam entering a treatment room in which a subject is exposed to the radiation. In the present embodiment the beam energy is measured to a resolution of about 2 MeV or better, which is equivalent to about 5 mm range in water (or soft tissue). A typical integrated dose for a proton therapy treatment fraction session is typically 2 to 5 Gy.

The total dose for proton CT imaging must be at a diagnostic level, as opposed to a treatment level. That is, CT imaging requires that the protons exit the subject so that they can be detected, rather than being absorbed within the subject thereby delivering a dose of radiation corresponding to the Bragg peak of FIG. 1. Thus, the protons need sufficient energy to penetrate the patient's entire anatomy.

Using apparatus according to embodiments of the present invention described herein, the estimated integrated dose in obtaining a full proton CT scan of a human head is 1-10 mGy. Such values compare favourably with conventional x-ray CT scans, since a typical head CT dose is about 50 mGy.

A challenge in developing a unified apparatus that can be used in each of the different operational modes described above, is that the system needs to be capable of operating over a range of very different proton flux levels, typically over a range of 3-4 orders of magnitude. Beam fluxes during treatment could be greater than $10^7$ protons/cm$^2$/s and as low as $10^4$ protons/cm$^2$/s during patent imaging. Such an integrated system would provide significant benefits in terms of reducing dose uncertainties, so providing more effective and safer treatment, as well as enhancing the efficiency of the complete radiotherapy workflow. Some embodiments of the present invention seek to provide such an integrated system.

Figure 4:
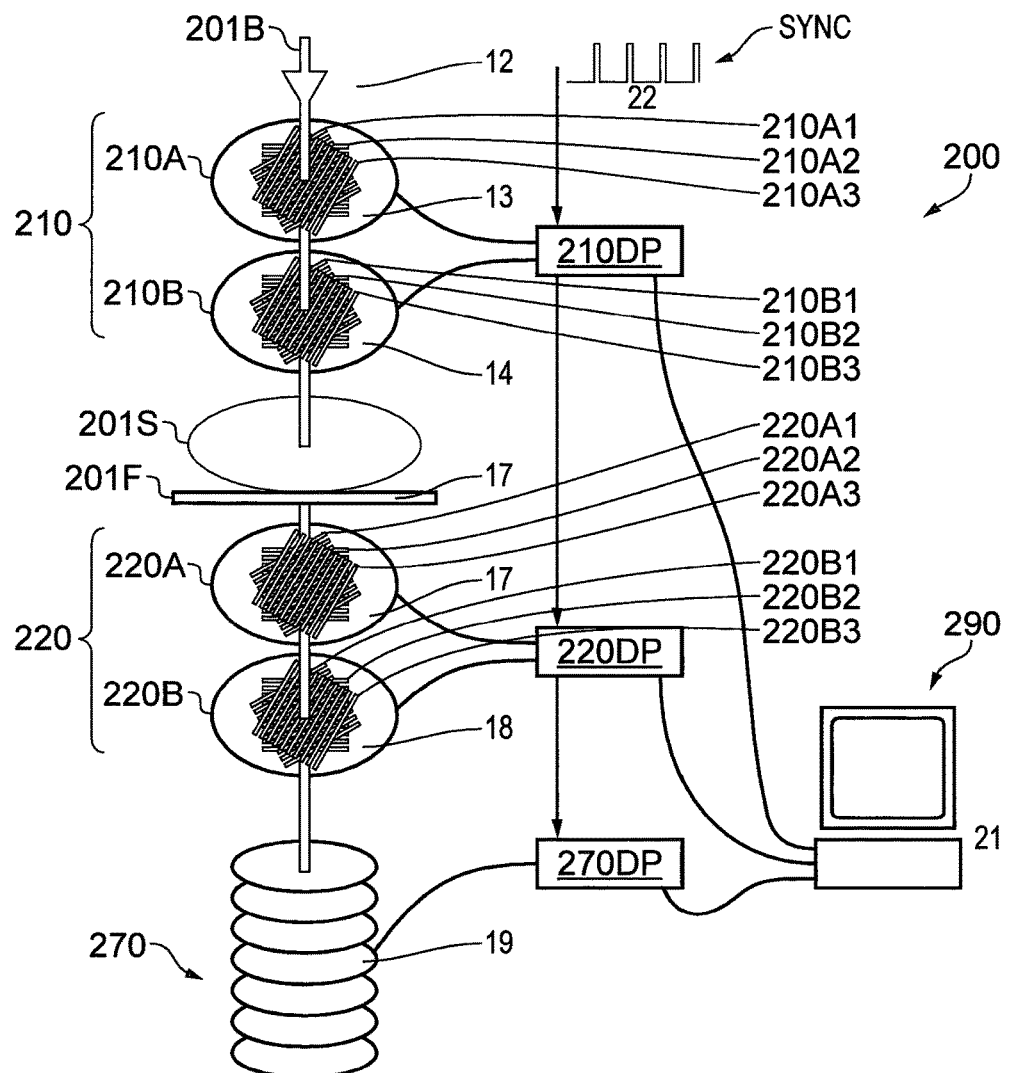
FIG. 4 illustrates apparatus according to an embodiment of the present invention.

FIG. 4 is a schematic illustration of a proton beam computerised tomography (CT) scanner apparatus 200 according to an embodiment of the present invention. The apparatus 200 is shown in a vertical arrangement with the incident proton beam 201B entering at the top of FIG. 4. It is to be understood that the apparatus 200 may be provided in any required orientation such as horizontal or at any other suitable angle. The apparatus 200 is illustrated such that the patient is rotated while the apparatus is stationary. It is to be understood that the reverse situation may be employed; namely that the patient is stationary and the apparatus is moved.

The proton beam 201B passes through a first beam tracker structure 210 which includes first and second position-sensitive detector (PSD) devices 210A, 210B. In the present embodiment the PSD devices 210A, 210B each include three solid-state strip detector devices 210A1, 210A2, 210A3, 210B1, 210B2, 210B3 as described in more detail below. The PSD devices 210A, 210B of the first beam tracker structure 210 will be referred to as the 'proximal PSD devices', with the first PSD device 210A being referred to as 'upper proximal PSD device' 210A and the second referred to as the 'lower proximal PSD device' 210B.

The proximal PSD devices 210A, 210B are each connected to a data processing unit 210DP that receives data from each device 210A, 210B indicative of a 2D location within an active area defined by each device 210A, 210B at which a proton has been detected passing through the respective device 210A, 210B. The data processing unit 210DP is in turn in communication with a primary control device 290 configured to provide overall control of the scanner apparatus 200.

A subject 201S such as a patient may be positioned on a support structure 201F immediately downstream of the lower proximal detector 210B with respect to a direction of travel of the beam 201B. If the apparatus 200 is arranged in a substantially horizontal plane, the subject 201S could for example be seated or positioned in some other manner.

The beam 201B then passes through a second beam tracker structure 220 which also includes first and second PSD devices 220A, 220B. The first and second PSD devices 220A, 220B of the second beam tracker structure 220 will be referred to herein as the 'distal' PSD devices. The first device 220A will be referred to as an 'upper' distal PSD device 220A and the second as a 'lower' distal PSD device 220B. The PSD devices 220A, 220B each include three solid-state strip detector devices 220A1, 220A2, 220A3 and 220B1, 220B2, 220B3, respectively, in a similar manner to the proximal PSD devices 210A, 210B as described in more detail below.

In a similar manner to the proximal PSD devices 210A, 210B, the distal PSD devices 220A, 220B are each connected to a data processing unit 220DP that receives data from the PSD devices 210A, 210B indicative of a 2D location within an active area defined by each PSD device 220A, 220B at which a proton has been detected passing through the respective device 220A, 220B. The data processing unit 220DP is in turn in communication with the primary control device 290.

Figure 5:
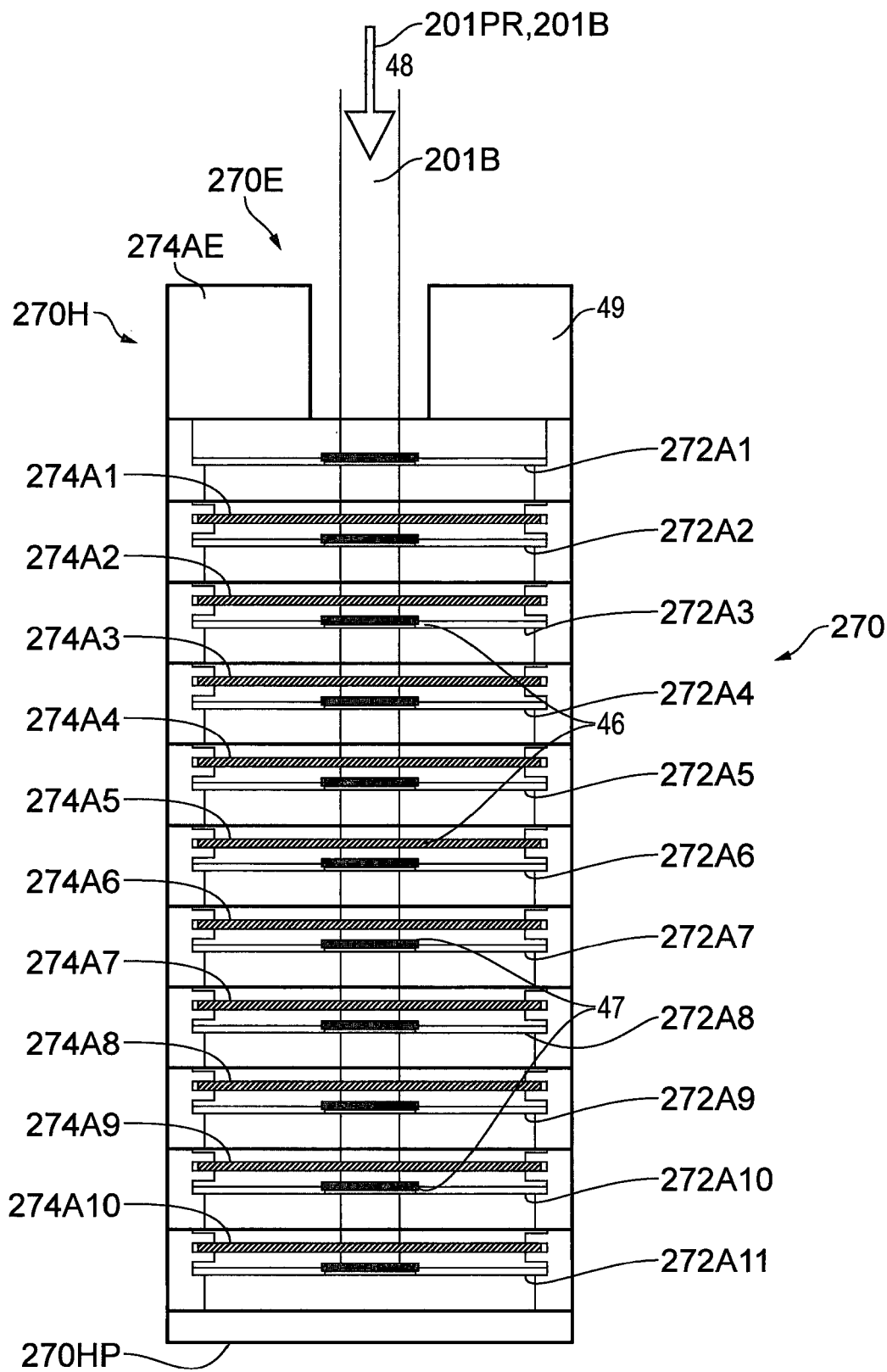
FIG. 5 illustrates a range telescope according to an embodiment of the present invention in cross-section.

After passing through the second beam tracker structure 220, the proton beam 201B enters an energy-resolving detector 270 illustrated in FIG. 5. The energy-resolving detector 270 will be referred to as a 'range telescope' 270. The range telescope 270 includes a stack of eleven (in the example illustrated) CMOS detector devices 272A1-11 mounted within a housing 270H. The CMOS detector devices 272A1-11 each include an array of CMOS photodiode devices enabling 2D position sensitive detection of proton radiation. In the embodiment of FIG. 5 the CMOS detector devices 272A1-11 are spaced apart from one another at substantially equal intervals along a direction of propagation of the proton beam 201B. Absorber elements 274A1-A10 are located between respective CMOS detector devices 272A1-11 and are configured to absorb energy from the beam 201B, the amount of energy absorbed being dependent on the thickness and nature of the respective absorber element 274A1-A10.

The range telescope 270 is arranged such that protons 201B entering the range telescope 270 pass successively through the CMOS detector devices 272A1-11 until they become absorbed by either one of the CMOS detector devices 272A1-11 themselves, an absorber element 274A1-A10 or a portion of the housing 270H of the range telescope 270 such as an end plate 270HP of the housing 270H.

The CMOS detector devices of the range telescope 270 are connected to an associated range data processing system 270DP (FIG. 4) which is in turn connected to the primary control device 290. The range data processing system 270DP is configured to receive a signal from each of the CMOS detector devices 272A1-11 corresponding to a location within a 2D active area, defined by the array of CMOS photodiode devices of each CMOS detector device 272A1-11, at which a proton is detected by each CMOS detector device 272A1-11. As described in further detail below, the range data processing system 270 is configured to determine a path of travel of a given proton through the range telescope 270 and a distance travelled by the proton within the range telescope 270.

As noted above, the primary control device 290 configured to provide overall control of the scanner apparatus 200. The device 290 is configured to accept control signals in respect of operation of the CT scanner apparatus 200 input by a user via a graphical user interface (GUI) and to provide overall control of the apparatus 200. In the present embodiment the apparatus 200 is configured to issue control signals to components of the apparatus 200. By way of example, the primary control device 290 may terminate a treatment session by blocking a path of travel of the beam 201B, for example by means of a beam stopper or blocker located upstream of a subject with respect to a direction of travel of the beam 201B, if unexpected behaviour by the apparatus 200 is detected, for example an unexpected deviation of the beam 201B from a path of travel, an unexpected increase in beam intensity, or other malfunction of the apparatus 200 or a proton generator that provides protons to the apparatus 200.

In the present embodiment, operation of the CMOS detector devices of the range telescope 270 is synchronised with the PSD devices of the first and second beam tracker structures 210, 220 in order to enable tracking of individual protons through the apparatus 200. Accordingly, in the present embodiment accurate synchronisation of event detection by the first and second beam tracker structures 210, 220 and range telescope 270 is performed, by reference to a periodically repeating synchronisation signal SYNC. In the present embodiment the synchronisation signal SYNC is generated by a proton generator that generates the proton beam although other arrangements are also useful. In some embodiments the synchronisation signal SYNC is generated by a signal generator of the apparatus 200. Generation of the signal by the proton generator has the advantage that event detection by the first and second beam tracker structures 210, 220 and range telescope 270 may be synchronised with the generation of the protons used.

Figure 6:
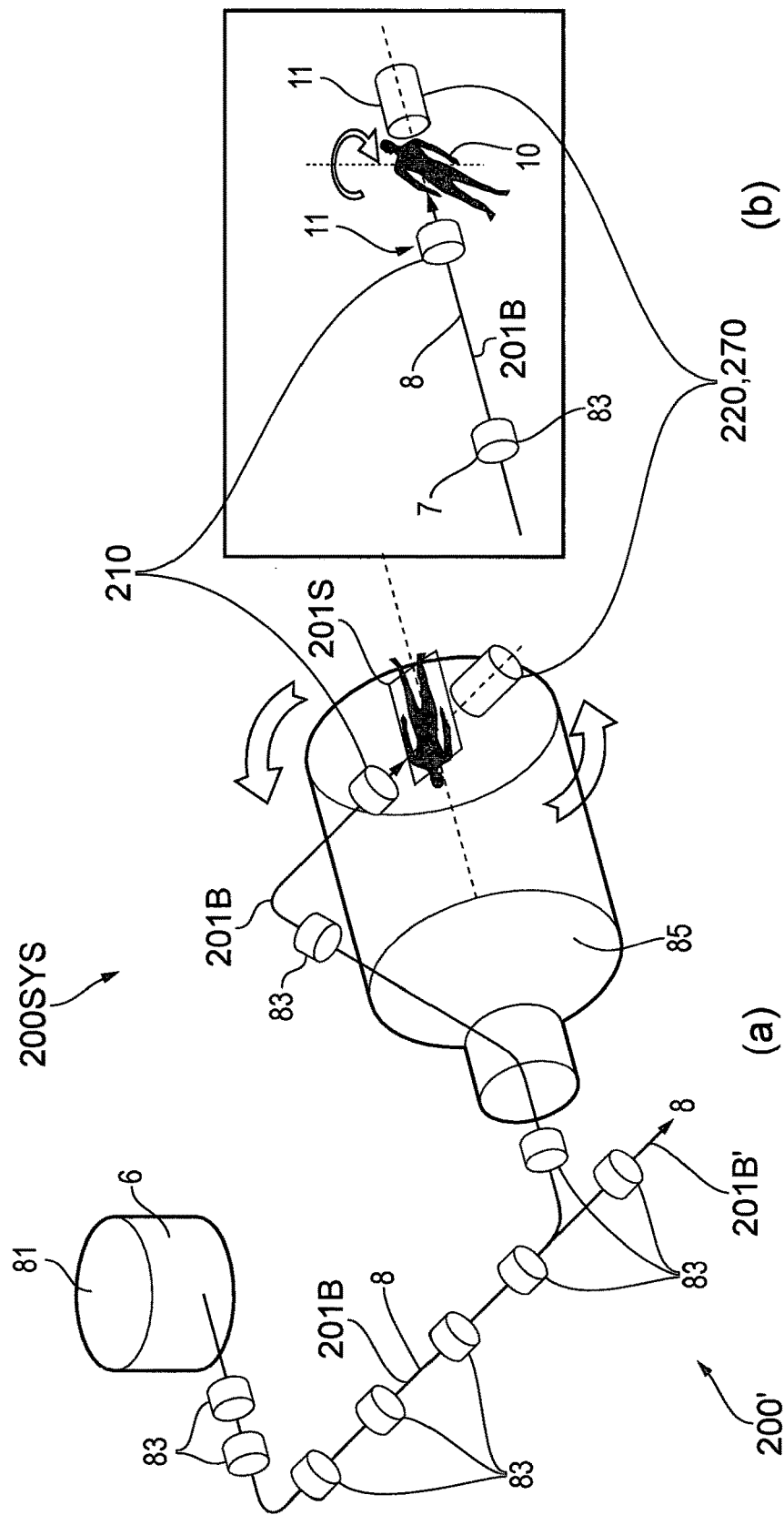
FIG. 6 shows elements of a proton therapy facility according to an embodiment of the present invention.
Figure 19:
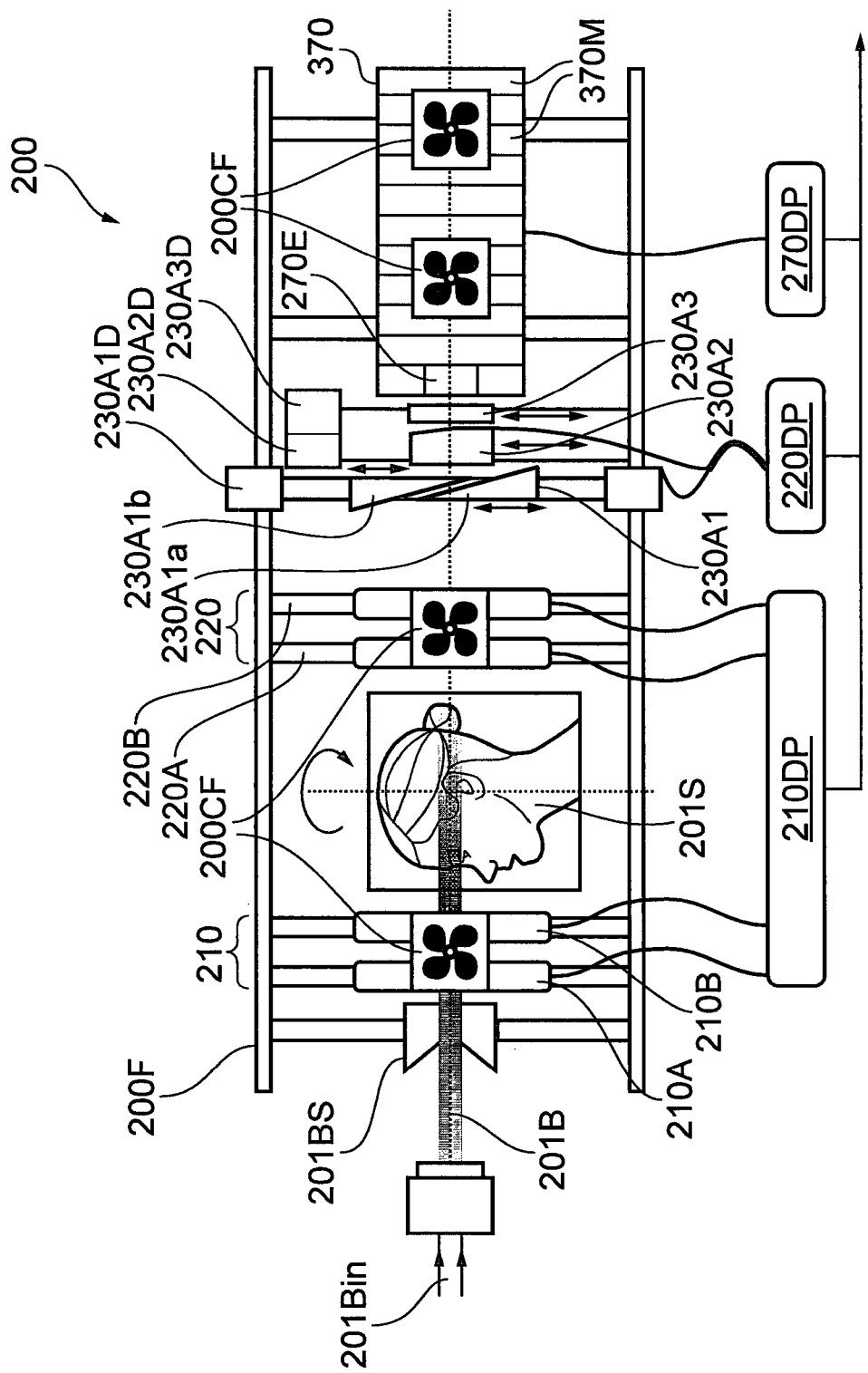
FIG. 19 is a schematic illustration of a general assembly of apparatus according to an embodiment of the present invention showing an arrangement of PSD devices, absorber portions, a subject and a range telescope.
Figure 20:
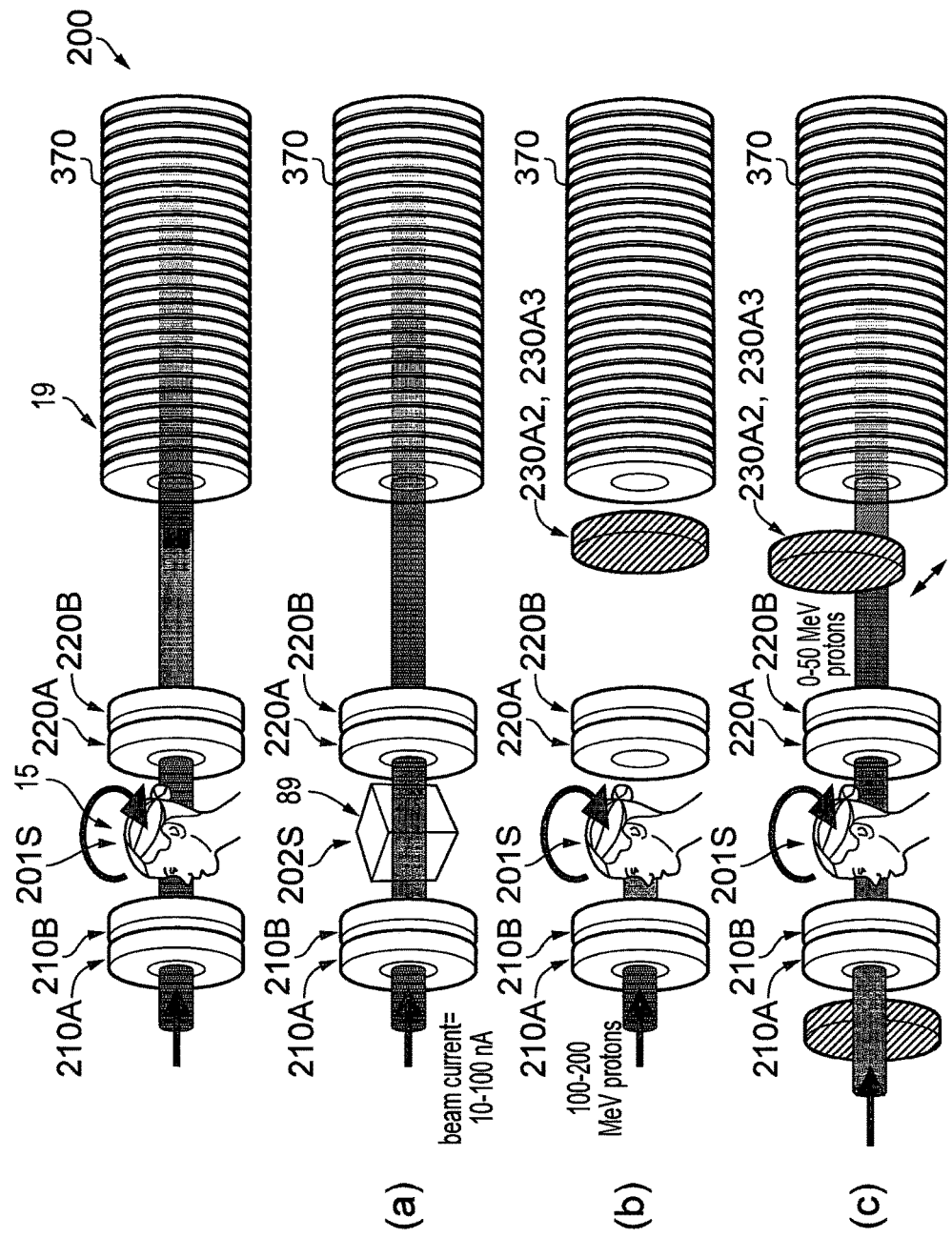
FIG. 20 is a schematic illustration of apparatus according to an embodiment of the present invention configured in (a) a quality assurance mode in which protons in the energy range 100-200 MeV are employed with a beam current of 10-100 nA; (b) a treatment monitoring mode in which protons in the energy range 100-200 MeV are employed with a beam current of 10-100 nA; and (c) a patient imaging mode in which protons in the energy range 150-250 MeV are employed with a beam current of 0.1-1 nA.

FIG. 6(a) illustrates the basic features of a proton therapy system 200SYS according to an embodiment of the present invention. The system 200SYS includes a particle accelerator system 81 and CT scanner apparatus 200'. The accelerator system 81 may be any suitable accelerator system 81 such as a cyclotron or a linear accelerator, which generates a beam of protons 201B with energies typically between 50 MeV and 350 MeV, as required. The beam 201B is directed (steered) and moderated in cross-sectional shape, energy and intensity by means of electromagnets 83 and other known components positioned along the required path of travel of the beam 201B. The beam 201B (which may be a fraction of the beam that entered the apparatus 200' from the accelerator system 81) may be directed to a gantry 85, which is arranged to permit the beam 201B to be delivered to a subject 201S over a predetermined range of angles of incidence with respect to the subject 201S. A gantry 85 is not employed in all facilities. In some alternative embodiments the beam direction may be substantially fixed, for example substantially vertical or horizontal, and the subject moved with respect to the beam 201B. Such a configuration is illustrated in FIG. 6(b), and is the manner in which the apparatus 200 of FIGS. 4, 19 and 20 is configured.

It is to be understood that a variety of different types of detector may be used to detect protons. In the present embodiment solid-state strip detector devices are used for the proximal and distal PSD devices 210A, 210B, 220A, 220B and a stack of CMOS photodiode detector devices 272A1-11 are used for the range telescope 270. It is to be understood that, in some alternative embodiments, other means for determining a path of travel of a proton through a subject, and an amount of energy lost by a proton upon passage through a subject (or the amount of residual energy possessed by a proton after passing through a subject) may be useful.

All detectors can suffer from damage due to exposure to high-energy radiation. Strip detectors are typically more resilient to such damage as they typically do not contain any active components within the detecting region. CMOS detectors can be designed and fabricated to increase their resilience to radiation damage. The passage of protons through the detectors and neighbouring materials gives rise to secondary radiation in the form of neutrons and x-rays, which can cause further damage to portions of the apparatus 200 including the detectors employed if such precautions are not taken.

It is to be understood that CMOS-based imaging devices are capable of recording directly conventional two-dimensional images since they are able to generate a signal that is responsive to the intensity of radiation incident on the detector as a function of position with respect to a two-dimensional active area of the device. CMOS-based imaging devices may be configured to have variable integration times and, in addition, CMOS-based imaging devices are capable of detecting relatively large numbers of individual protons without saturating. The ability to detect relatively large numbers of individual protons without saturating enables tracking of protons through CT scanner apparatus at relatively high fluxes.

Figure 7:
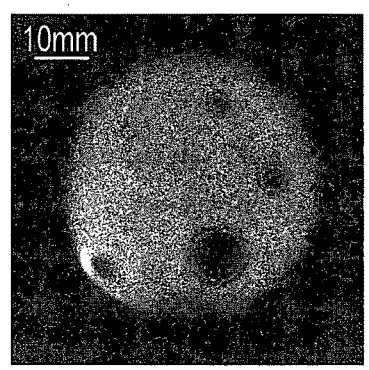
FIG. 7 is a 29 MeV proton projection image of a phantom recorded using a single CMOS detector device according to an embodiment of the present invention.

A radiographic image of a PMMA (polymethyl methacrylate) plate (which may be referred to herein as a phantom), 5 cm in diameter and with a series of different sized holes drilled through it, irradiated with 29 MeV protons, is shown in FIG. 7. The image was recorded using the apparatus illustrated in FIG. 4 which is described in further detail below. In the image, darker areas represent areas of increased detected proton intensity.

Strip Detectors

Figure 8A:
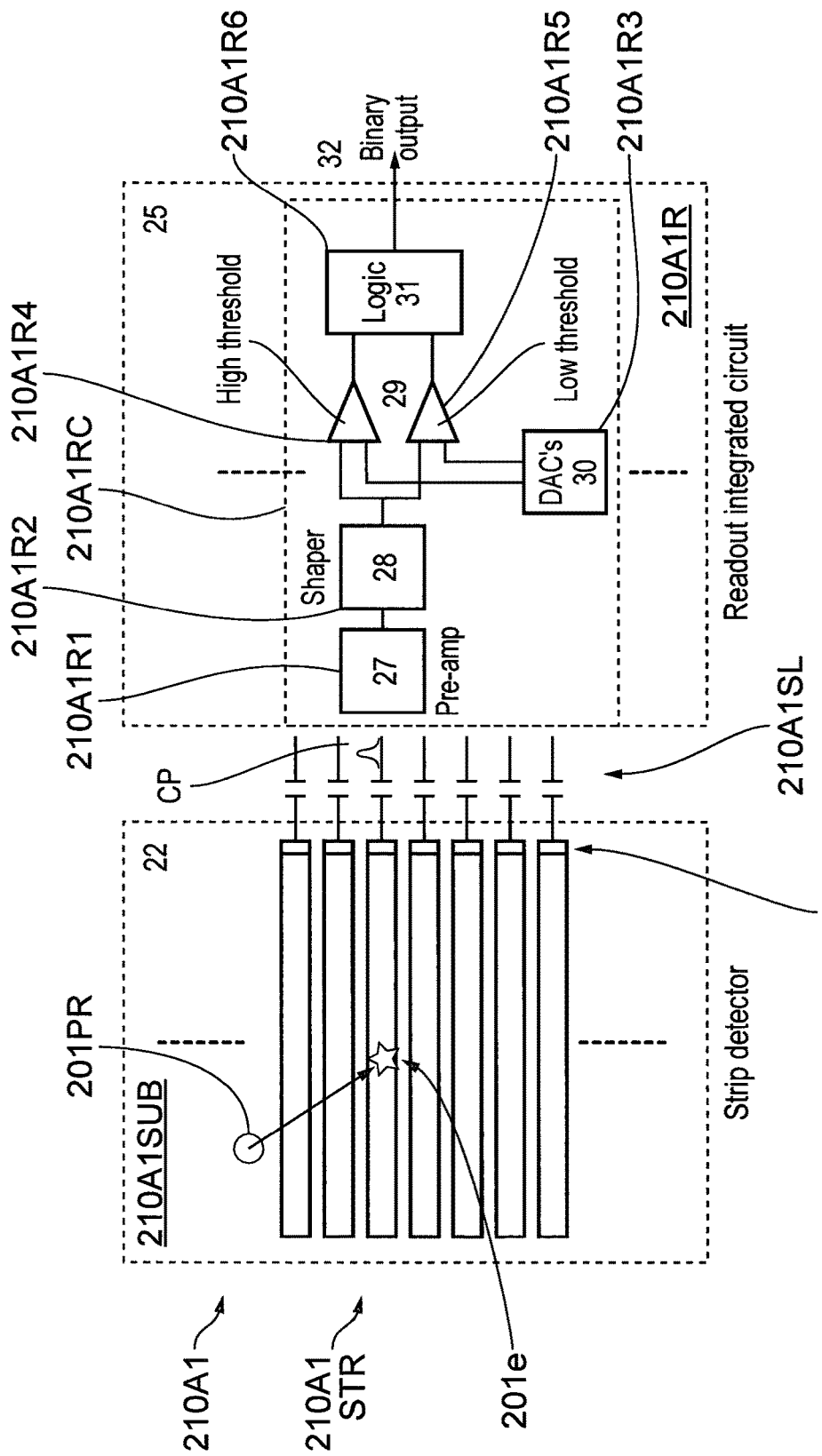
FIG. 8 shows (a) a strip detector device with read-out circuit according to an embodiment of the invention and (b) a strip element of the strip detector device shown in (a)

As noted above, the proximal and distal PSD devices 210A, 210B, 220A, 220B each include solid-state strip detector devices. A first strip detector device 210A1 of the upper proximal PSD device 210A of the embodiment of FIG. 4 is illustrated in FIG. 8(a). It is to be understood that the strip detector devices 210A1-3, 210B1-3, 220A1-3, 220B1-3 of the first and second beam tracker structures 210, 220 are each substantially identical in construction and the following description of the first strip detector device 210A1 of the upper proximal PSD device 210A is applicable to each of the devices 210A1-3, 210B1-3, 220A1-3, 220B1-3 of the apparatus 200.

Figure 8B:
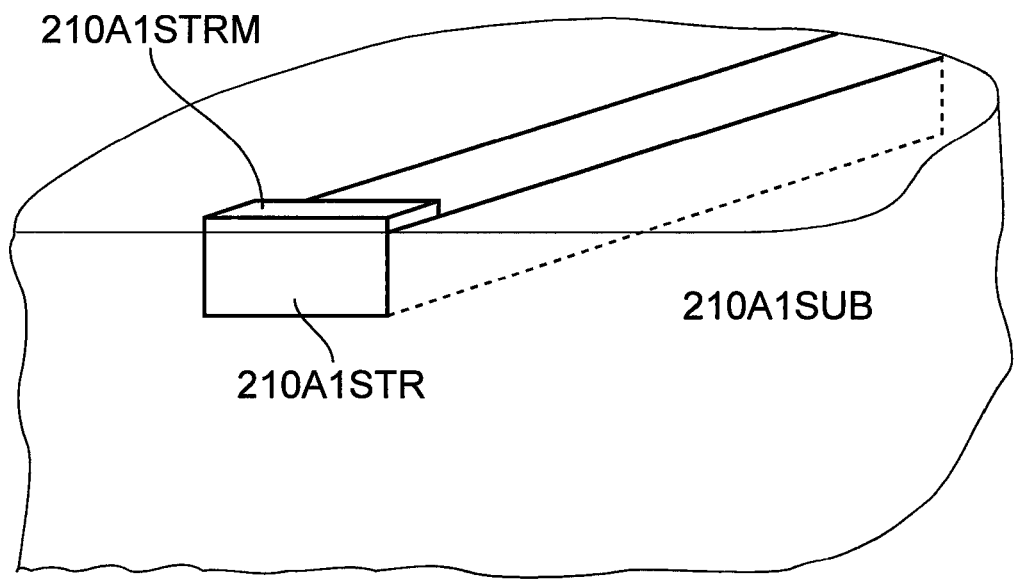

The strip detector device 210A1 includes a semiconductor substrate 210A1SUB upon which is formed an array of semiconductor strip elements 210A1STR one of which is illustrated schematically in FIG. 8(b). In the embodiment of FIG. 8 the substrate 210A1SUB is a lightly doped n-type silicon wafer. The strip elements 210A1STR are each in the form of an elongate volume of n-type doped semiconductor material formed in the substrate 210A1SUB such that a pn junction is formed between the strip elements 210A1STR and the substrate 210A1SUB. In the present embodiment each substrate 210A1SUB has 1000 substantially parallel strip elements 210A1STR although other numbers may be useful in some embodiments.

The strip elements 210A1STR are arranged in a periodic stripe structure across the surface of the substrate 210A1SUB. A metal contact 210A1STRM is provided at one end of each strip element 210A1STR to enable electrical connection to be made to the strip elements 210A1STR.

The strip elements 210A1STR are each connected to a respective channel 210A1RC of a readout circuit 210A1R (FIG. 8(a)). The readout circuit 210A1R is configured to apply a reverse bias potential across the pn junction formed at the interface between each strip element 210A1STR and the substrate 210A1SUB in order to enable collection, and therefore detection, of charged particles generated when a charged particle such as a proton passes through one of the strip elements 210A1STR.

When a charged particle such as a proton 201PR passes through a strip element 210A1STR, free electrons 201e are generated. The free electrons 201e drift to a collection node provided by the metal contact 210A1STRM and a charge pulse CP is generated in a signal line 210A1SL that couples the strip element 210A1STR to the corresponding channel 210A1RC of the readout circuit 210A1R. The readout circuit 210A1R is provided by a custom application specific integrated circuit (ASIC) 215 (FIG. 21) that processes the analogue signal provided by the charge pulse CP. The readout circuit 210A1R is configured to generate a binary signal indicating the identity of the strip element 210A1STR in which the free electrons 201e were generated. It is to be understood that in some alternative embodiments the readout circuit 210A1R may generate an analogue signal or multi-level digital signal in addition or instead. The analogue and multi-level digital signals may provide an indication of the magnitude of the charge pulse CP in some embodiments.

The readout circuit 210A1R includes a pre-amplifier portion 210A1R1, pulse-shaper portion 210A1R2 and comparator portions 210A1R4, 5. Incoming charge pulse CP is amplified by the pre-amplifier portion 210A1R1 and processed by the pulse-shaper portion 210A1R2 to output a signal of reduced noise. The output signal is applied to an input of each of the comparator portions 210A1R4, 5 which have respective different reference potential signals applied thereto by a programmable digital-to-analogue convertor portion 210A1R3. Comparator portion 210A1R4 has a relatively high reference potential applied to an input thereof whilst comparator portion 210A1R5 has a relatively low reference potential applied to an input thereof. Logic circuit portion 210A1R6 receives a signal output by each of the comparator portions 210A1R4, 5 and determines whether a detected charge pulse CP is a valid event signal corresponding to detection of a proton 201PR. The logic circuit portion 210A1R6 performs a range of logical operations in order to determine this, prior to generating a binary output signal indicative of the detection of a proton 201PR. In order to generate a binary output signal indicative of detection of a proton 201PR, the charge pulse CP must have a magnitude that is above a minimum level (set such that random fluctuations in current flow through or potential of a given strip element 210A1STR do not result in an output by the logic circuit portion 210A1R6 indicative of detection of a proton 201PR) and below a maximum level, set such that an output by the logic circuit portion 210A1R6 indicative of detection of a proton 201PR does not occur if a charge pulse CP is detected that was generated by two or more protons.

A single array of strip elements 210A1STR as embodied in each strip detector device 210A1-3, 210B1-3, 220A1-3, 220B1-3 is able to determine the position at which a proton 201PR is incident upon the device 210A1-3, 210B1-3, 220A1-3, 220B1-3, also referred to as the position of a "hit", with respect to the active area of one strip element 210A1STR of a given device. That is, a single array of strip elements 210A1STR is able to determine the position at which a proton 201PR is incident upon the device with respect to one direction or axis, that is parallel to a direction normal to the longitudinal axis of each of the strip elements 210A1STR and parallel to a plane of the substrate 210A1SUB bearing the strip elements 210A1STR.

It is to be understood therefore that in order to recover the position at which a proton 201PR is incident upon the device in two dimensions, for example with respect to Cartesian (x-y) coordinates, two strip detector devices 210A1 are normally used, substantially superimposed on one another, and with the longitudinal axes of the strip elements 210A1STR substantially orthogonal to one another, or 'crossed'.

Figure 10:
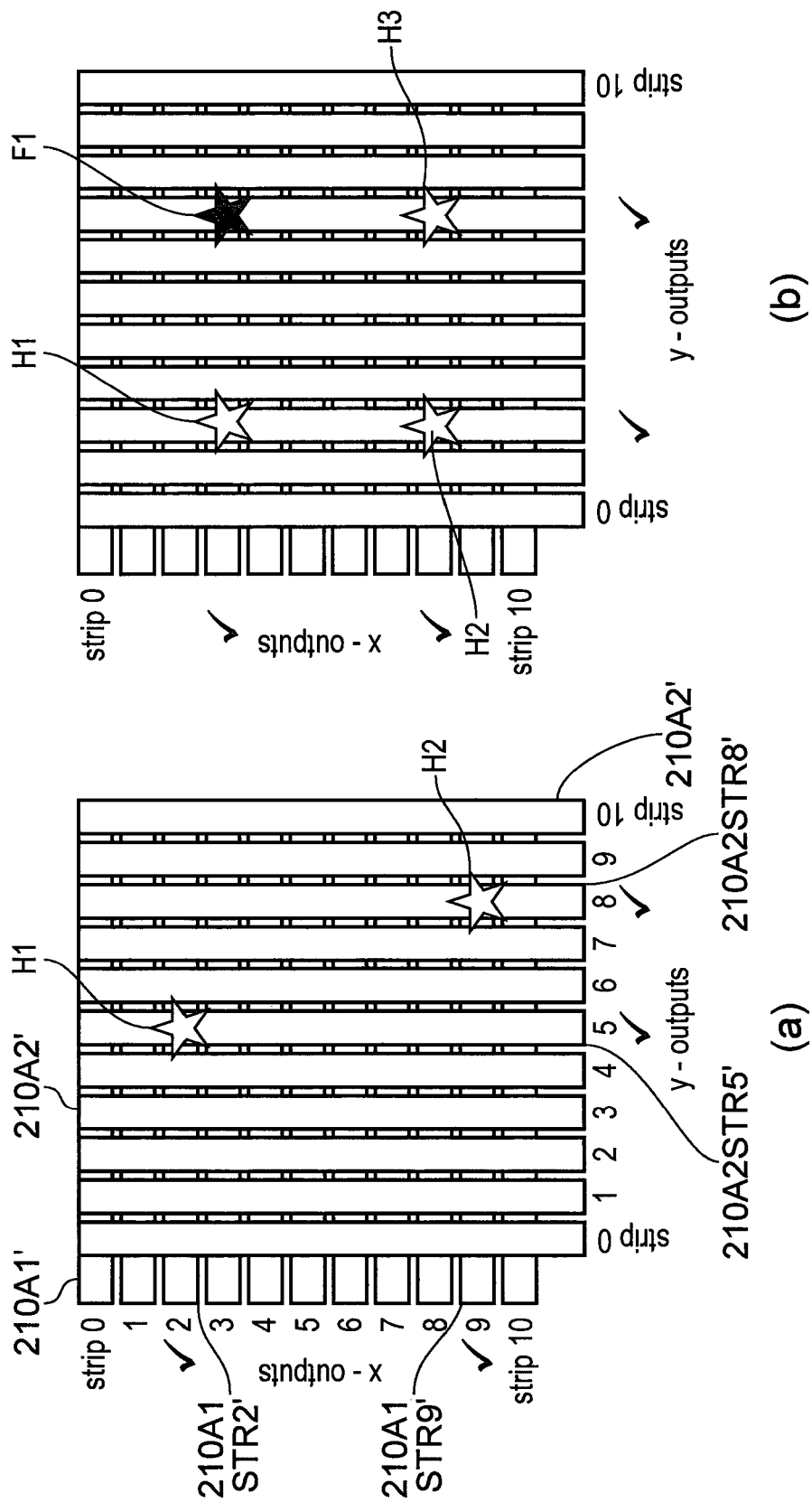
FIG. 10 is a schematic plan view of a known detector device to illustrate the effect of multiple events in a single readout cycle, two substantially simultaneous events being shown occurring in (a) and three substantially simultaneous events being shown occurring in (b)

Using a pair of crossed two strip detector devices 210A1 it is possible to record several hits correctly within the readout time of a readout circuit 210A1R, but the problem exists that false hits may also be recorded. This problem is illustrated in FIG. 10.

Figure 3:
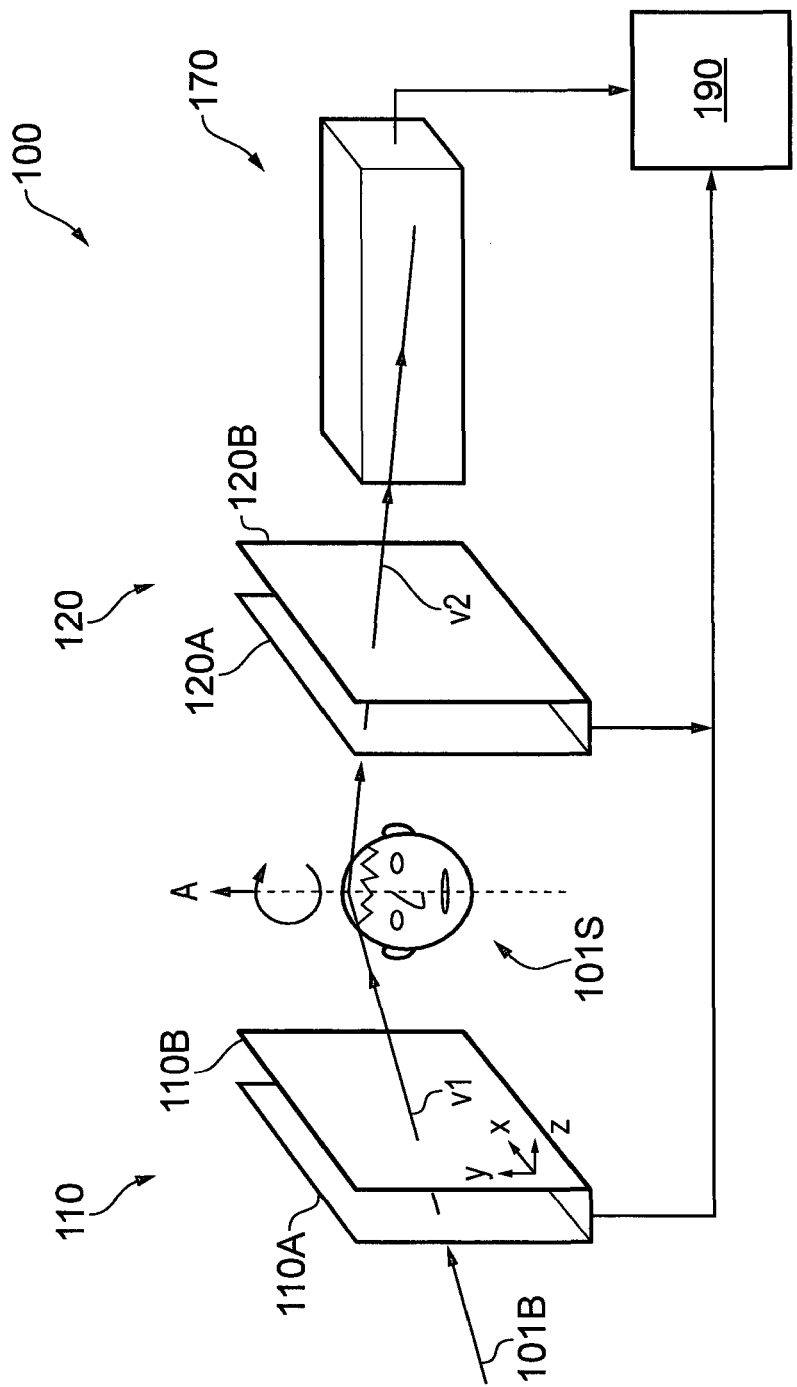
FIG. 3 is a schematic illustration of a known proton CT system or apparatus.

In FIG. 10(a), a pair of strip detector devices 210A1', 210A2' similar to those of the prior art arrangement of FIG. 3 are shown, oriented in the crossed configuration with respect to one another. In the example scenario illustrated, two 'hits' are shown occurring at locations H1 and H2 of the devices 210A1', 210A2' at substantially the same time, i.e. within one readout cycle of readout circuits associated with the strip detector devices 210A1', 210A2'.

Hit H1 results in charge pulses being generated in strip 210A1STR2' of the first strip detector device 210A1' and strip 210A1STR5' of the second strip detector device 210A2'.

Hit H2 results in charge pulses being generated in strip 210A1STR9' of the first strip detector device 210A1' and strip 210A2STR8' of the second strip detector device 210A2'.

As noted above, charge pulses are generated and output to the corresponding readout circuits of the strip detector devices 210A1', 210A2'. The two hits, at H1 and H2, may be correctly detected as having occurred at locations <X, Y> where X refers to the strip number (210A1STR0-10') of device 210A1' by means of which of a proton has been detected and Y refers to the strip number (210A2STR0-10') of device 210A2' by means of which of a proton has been detected. Thus, hits H1 and H2 occur at locations <2,5> and <9,8> with respect to the strips 210A1STR0-10' and 210A2STR0-10' and can be detected even if the hits occur within the same readout cycle.

FIG. 10(b) shows an example scenario in which three hits, H1, H2, H3 occur at locations <3,2>, <8,2> and <8,7> respectively, substantially simultaneously. The hits H1, H2, H3 are detected by the readout circuit associated with the devices 210A1', 210A2' but a false hit is recorded at position <3,7>, indicated at F1. The number of false hits increases as the particle flux increases, and is due to more than one hit occurring on a single strip element during the read-time of the readout circuit. As the charge generated by multiple hits is larger than that from a single hit, it is possible to set an upper threshold in the readout circuit to ignore strips hit by multiple events as described above. This can prevent "false positives", but can create "false negatives" in that real hits are ignored. As the position of individual interactions is a random process, it is not possible to faithfully reconstruct the true flux or the shape of the proton beam. The number of ambiguities can be reduced, for a given flux, by splitting the strip elements in half, applying a reverse bias potential to each strip element. Charge pulses CP can then be read out from both ends. It is to be understood that splitting the strip elements in half halves the effective area of each strip.

As described above, each PSD device 210A, 210B, 220A, 220B has three strip detector devices 210A1-3, 210B1-3, 220A1-3, 220B1-3. The three strip detector devices of each PSD device 210A, 210B, 220A, 220B are oriented at 120° to one another as illustrated schematically in FIG. 9. The three strip detector devices of each PSD device 210A, 210B, 220A, 220B produce individual binary output data streams from respective data signal output lines associated with the respective detector. The data signal output lines associated with the three strip detector devices 210A1-3 of the upper proximal PSD device 210A are labelled 210A1D, 210A2D and 210A3D, respectively in FIG. 9, by way of illustration. It is to be understood that if one of the strip elements 210A1STR of a given PSD device 210A, 210B, 220A, 220B, such as a strip element of device 210A1 (which may be referred to as detecting particle position with respect to an 'x' direction), is hit more than once in a given read cycle, there is an increased probability that the corresponding strips 210A2-3 (which may be referred to as being arranged to detect particle position with respect to 'u' and 'v' directions, respectively), are hit only once. It is therefore possible to unambiguously record the locations of more hits than in the case of only two crossed strips, per the arrangement of FIG. 10.

The number of ambiguities for N hits per readout cycle (or read-time) where only two strip detector devices are employed in an orthogonal (crossed) orientation with respect to one another, is $N^2-N$. For example, for 5 actual hits in a given read-time for two orthogonal planes, there will be on average 20 ambiguities.

Figure 9:
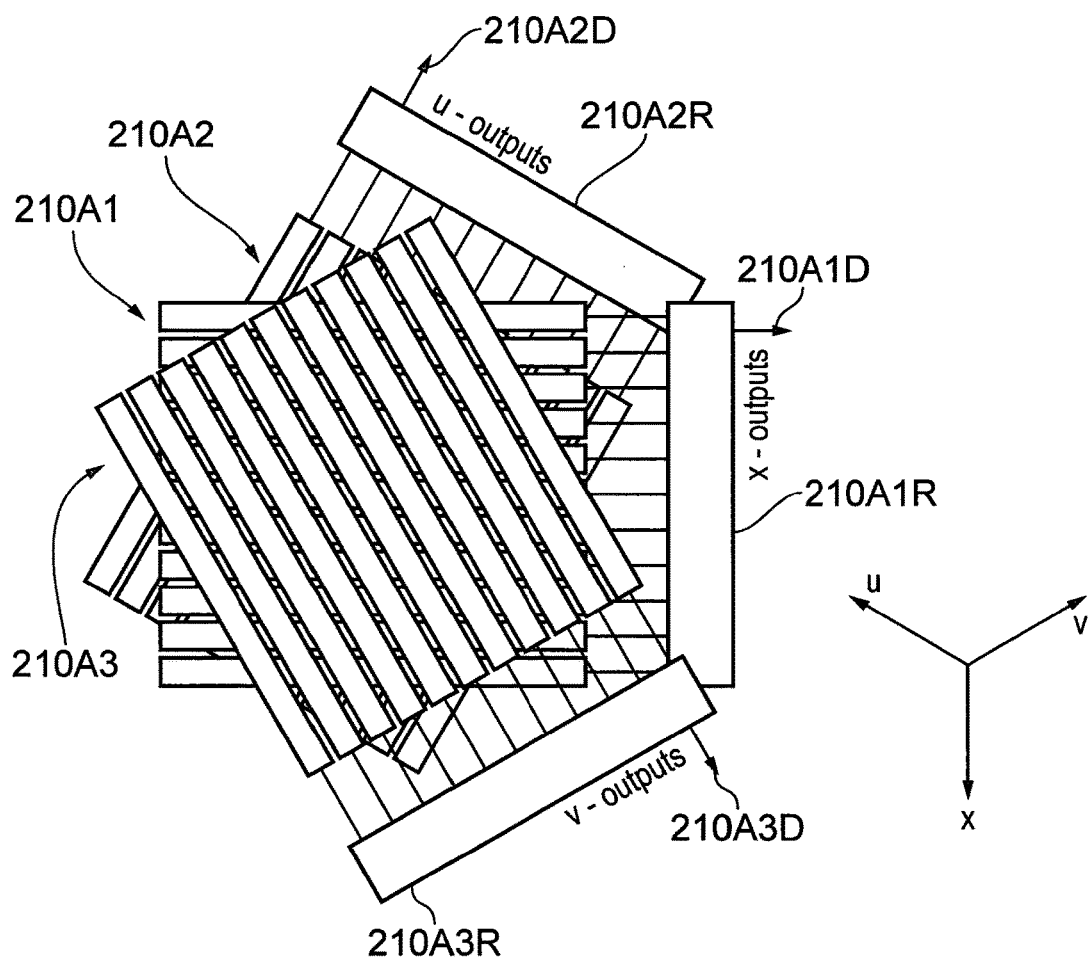
FIG. 9 is a schematic plan view, in a direction parallel to a direction of travel of a beam through a beam tracker structure, of a position sensitive detector (PSD) device according to an embodiment of the present invention having three equispaced strip detector devices oriented at 120 degrees with respect to one another.

Based on extensive simulations by the present applicant, three strip detector devices, with strip elements (100 um wide and length 50 mm) oriented respectively along axes u, v, and x arranged at 120° to one another as described with respect to FIG. 9, will have an ambiguity rate of only 0.6% for 5 actual hits at a read cycle of 40 ns. This is an improvement of over 660 times in the ambiguity rate compared to just two orthogonal strips.

The profile, that is the overall shape and intensity, of the proton beam within the boundary of an active area of a given detector device 210A, 210B, 220A, 220B can be reconstructed from the three profiles or histograms that may be produced from each of the corresponding strip detector devices 210A1-3, 210B1-3, 220A1-3, 220B1-3 over time using well-known mathematical techniques. Alternatively, if the requirement is simply to monitor the quality of the beam in terms of stability of the shape, position and intensity during treatment, then this can be achieved by considering the shape, positioning and magnitude of the profiles alone, with no need to reconstruct the two-dimensional image. This feature may be employed to monitor beam position, shape and/or flux during treatment of a subject Thus, beam position, shape and/or flux can be monitored even when substantially all of the protons are being absorbed by the subject in a treatment mode of operation of the system 200SYS.

It is to be understood that in order to record the paths of individual protons 201PR as they pass through the apparatus 200 to the subject 201S and to track the direction of the individual protons 201PR after they have passed through the subject 201S, the first beam tracker structure 210, which includes the first and second PSD devices 210A, 210B, is positioned immediately upstream of the subject 201S whilst the second beam tracker structure 220 which also includes first and second PSD devices 220A, 220B, is positioned immediately downstream of the subject 201S. It is to be understood that the beam tracker structures 210, 220 each have two PSD devices 210A, 210B, 220A, 220B since the incident proton beam 201B may not be fully collimated (that is, not travelling normal to the plane of the PSD devices 210A, 210B, 220A, 220B) and may exhibit divergence or other anomalies.

Figure 11A:
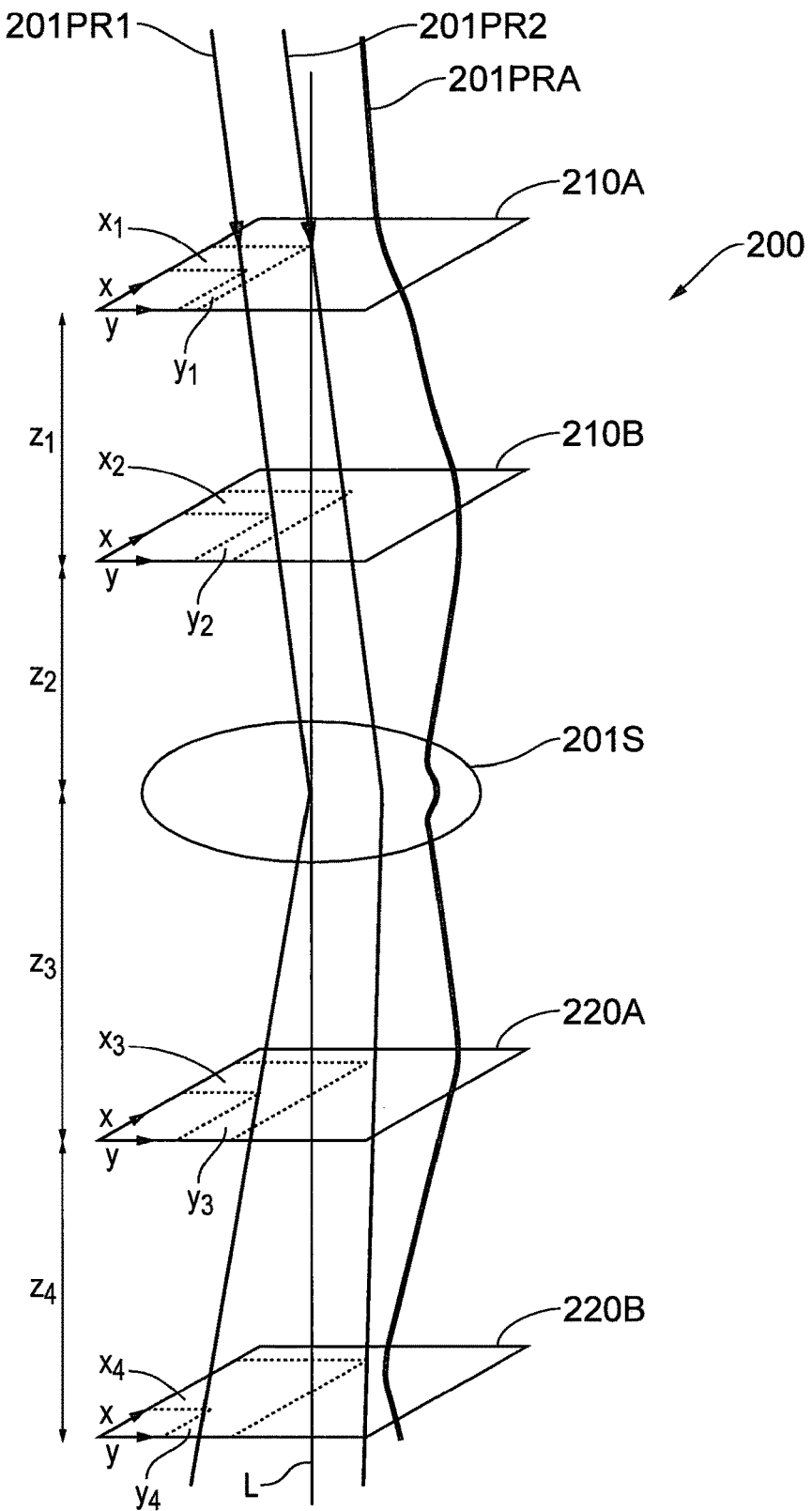
FIG. 11 is a schematic illustration of (a) a portion of apparatus according to an embodiment of the present invention illustrating proton track estimation using four position sensitive detector devices, (b) a side view of the apparatus shown in (a), and (c) a 3D view of a multiwire proportional chamber detector device suitable for use in embodiments of the present invention.

The basic geometry of the proposed arrangement of four detector devices 210A, 210B, 220A, 220B in different respective detector planes is illustrated in FIG. 11. The PSD devices 210A, 210B, 220A, 220B share a common longitudinal axis L and arranged at successive locations along the axis L, with their major plans substantially normal thereto. The tracks of two individual protons 201PR1, 201PR2 scattered in a subject 201S such as a human patient are illustrated. The upper and lower proximal PSD devices are shown at 210A, 210B respectively whilst the upper and lower distal PSD devices are labelled 220A, 220B respectively.

Knowing the spacings z1, z2, z3 and z4 between the PSD devices 210A, 210B, 220A, 220B and the subject 201S, and the corresponding <X,Y> coordinates at which hits occur in each PSD device 210A, 210B, 220A, 220B it is possible to reconstruct the paths of the protons 201PR1, 201PR2 as shown in FIG. 11. If the number of detected protons 201PR within one read-time is small, it is still possible to identify individual tracks. Proton tracks, in reality, follow a nondeterministic path as they undergo multiple scattering and other interactions and a typical actual path of a proton through the apparatus is shown at 201PRA. It is to be understood that an algorithm that is devised to correlate individual protons across the detectors will typically be required to assume a smooth overall path to which some cost function needs to be minimized.

Figure 11B:
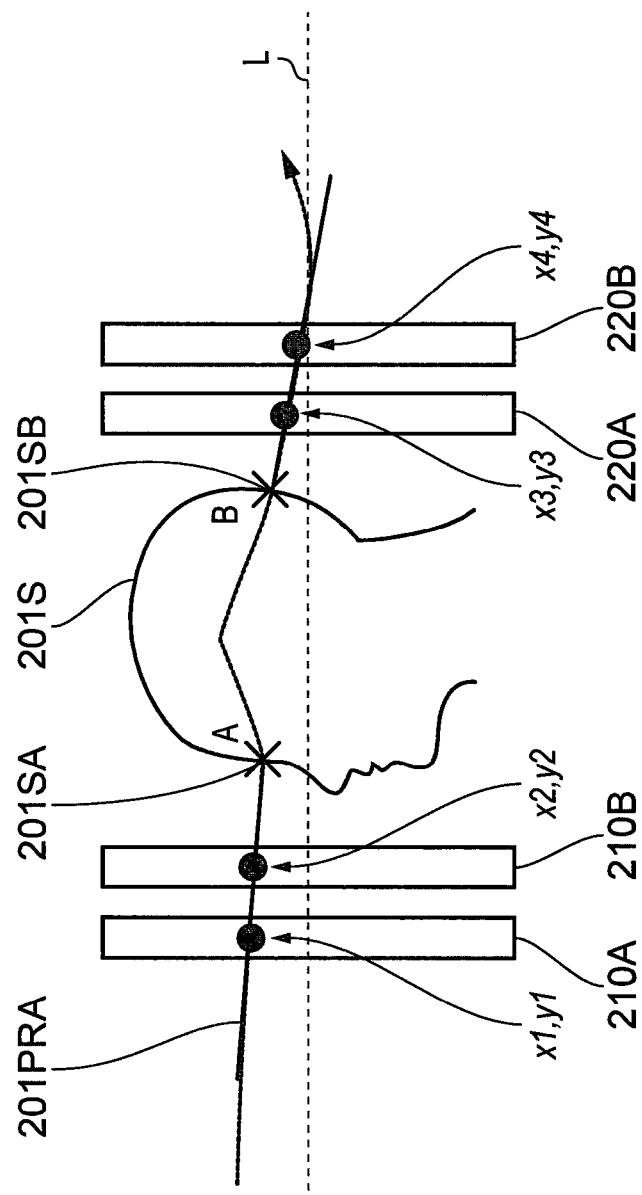

FIG. 11(b) illustrates passage of a proton 201PRA through the PSD devices 210A, 210B, 220A, 220B in side view. As noted above, two PSD devices 210A, 210B are positioned in front of the patient 201S and two PSD devices 220A, 220B are placed immediately after the patient 201S. Particles, such as protons, with sufficient energy will pass through the patient 201S and their tracks are recorded by events occurring in each of the PSD devices 210A, 210B, 220A, 220B. If the readout period of the PSD devices is sufficiently short and the particle flux is suitably low, then there can be only one particle 201PR traversing the PSD devices 210A, 210B, 220A, 220B and patient in the readout period. The co-ordinates (x1, y1) and (x2, y2) of the location at which the particle 201PR passes through each of the PSD devices 210A, 210B, in front of the patient 201S give the equation of a straight line in space since the spacing between the PSD devices 210A, 210B is known, and provide a good estimate of the entry position, 201SA, of the particle 201PR into the patient 201S. Similarly the co-ordinates (x3, y3) and (x4, y4) of the locations at which the particle 201PR passes through each of the PSD devices 220A, 220B behind the patient 201S give the equation of a straight line in space since the spacing between the PSD devices 220A, 220B is known. They enable a good estimate of the exit position, 201SB, of the particle 201PR from the patient 201S. Knowledge of the points of entry 201SA and exit 201SB can be helpful in the creation of CT images of the region of the patient 201S being irradiated.

In some embodiments, other types of strip detector may be employed such as detectors employing ionizing gas. Linear detector elements of the strip detector may be enclosed in a sealed environment of an ionizing gas or gas mixture, such that incident radiation creates a local ionization of the gas which in turn is detected by an electronic readout mechanism.

For example, a multi-wire proportional chamber device may be employed, a microstrip gas chamber, gas electron multiplier or any other suitable ionizing gas detector having an array of 1D electrodes for detecting ionization of gas by hadrons. Other types of detector may also be useful. The detectors may be arranged such that linear detector elements forming conductive electrodes such as wires or strips are enclosed in a sealed environment of an ionizing gas which may be a gas mixture. An electrical potential is established within the sealed environment between the electrodes or between the electrodes and a further one or more electrodes and flow of current between electrodes due to ionization of the gas by radiation is detected. By monitoring the identity of the electrodes experiencing current flow due to ionization of the gas by particles of radiation, information relating to the location of the device at which radiation passed through the device may be obtained.

Figure 11C:
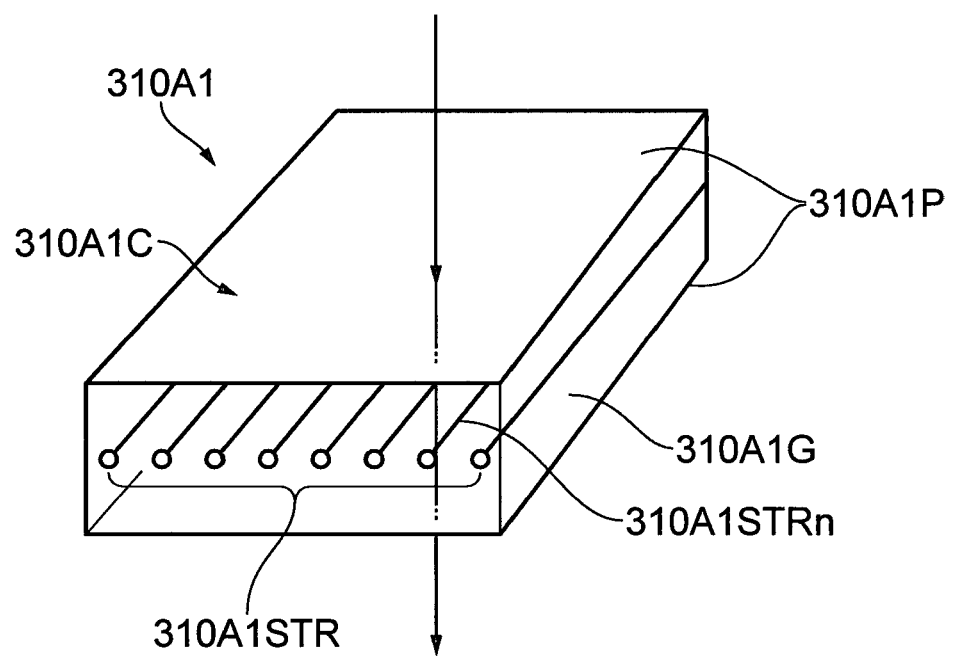

FIG. 11(c) illustrates a strip detector device 310A1 according to an embodiment of the invention in the form of a multiwire proportional chamber detector device 310A1. The device 310A1 has first and second planar conductive cathode plates 310A1P arranged a mutually parallel to and substantially coextensive with one another. The plates 310A1P define major faces of a gas-tight chamber 310A1C in which a gas 310A1G is contained. A 2D array of conducting metallic wires 310A1STR is arranged to span the chamber 310A1C from one side to the other. The wires 310A1STR are provided substantially midway between the plates 310A1P and run substantially parallel to the plates 310A1P. The wires 310A1STR terminate outside the chamber 310A1C allowing electrical connection to be made to the wires 310A1STR. It is to be understood that a PSD device suitable for use in an embodiment of the present invention may be produced by arranging three or more of the detector devices 310A1 at successive locations along a beamline. The devices 310A1 are located with the plane of each 2D array of wires substantially normal to the beamline and such that the wires 310A1STR of respective devices 310A1 are non-parallel.

It is to be understood that, in some embodiments, the PSD device may comprise a mosaic of detector elements that is structurally a 2D array but is employed as a 1D array.

Range Telescope

As described above, the apparatus 200 has a range telescope 270 illustrated in FIG. 5. The range telescope 270 is configured to enable measurement of the residual energy of protons 201PR entering the range telescope 270, that is their path lengths, which bears an equivalence with their residual energy, after passing through a subject 201S.

Figure 12:
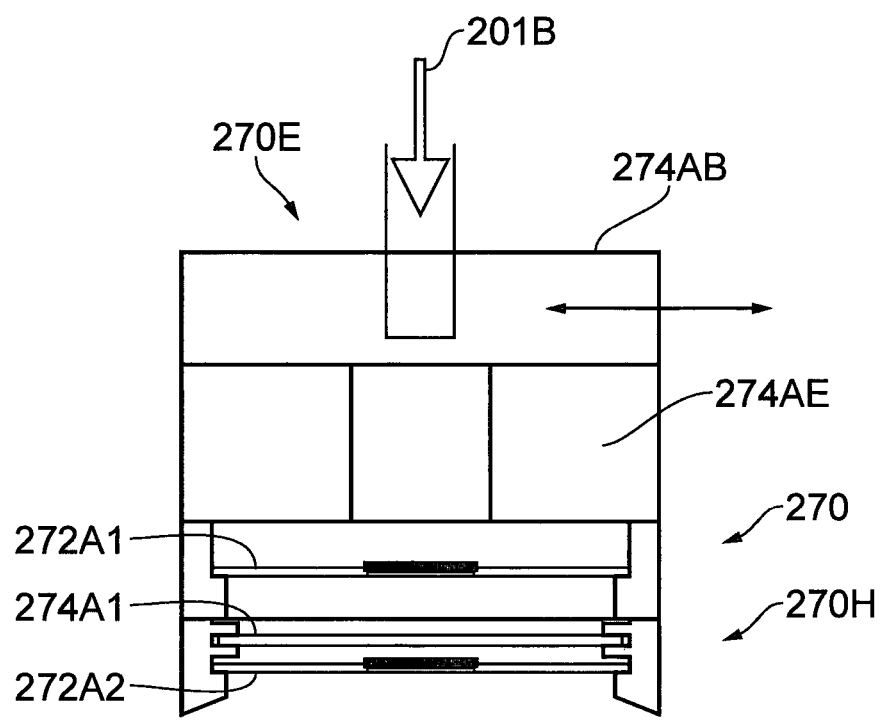
FIG. 12 is a schematic illustration of a moveable absorber portion provided at an entrance to a range telescope according to an embodiment of the present invention.

The residual energy, $E_R$, of a proton 201PR can be inferred through the concept of the water-equivalent path length (WEPL), and two-dimensional images of a subject 201S are constructed based on a knowledge of WEPL and proton trajectory through the first and second beam tracker structures 210, 220 and energy lost in the subject which can be inferred from the residual energy provided by the range telescope 270. Range telescopes 270 are often referred as energy-discriminating detectors. As described above, the range telescope 270 has a stack of two-dimensional CMOS detector devices 272A1-11 mounted within a housing 270H. Absorber elements 274A1-A10 may be provided between respective CMOS detector devices 272A1-11 that are configured to absorb predetermined amounts of energy from the beam 201B. In the embodiment of FIG. 5, an annular absorber element 274AE is provided at an entrance 270E of the telescope 270 in order to protect electronic assemblies within the telescope 270 from scattered radiation. A moveable absorber block 274AB is optionally positioned at the entrance of the telescope immediately upstream of annular absorber element 274AE to limit the energy range of protons entering it as illustrated schematically in FIG. 12.

Figure 13:
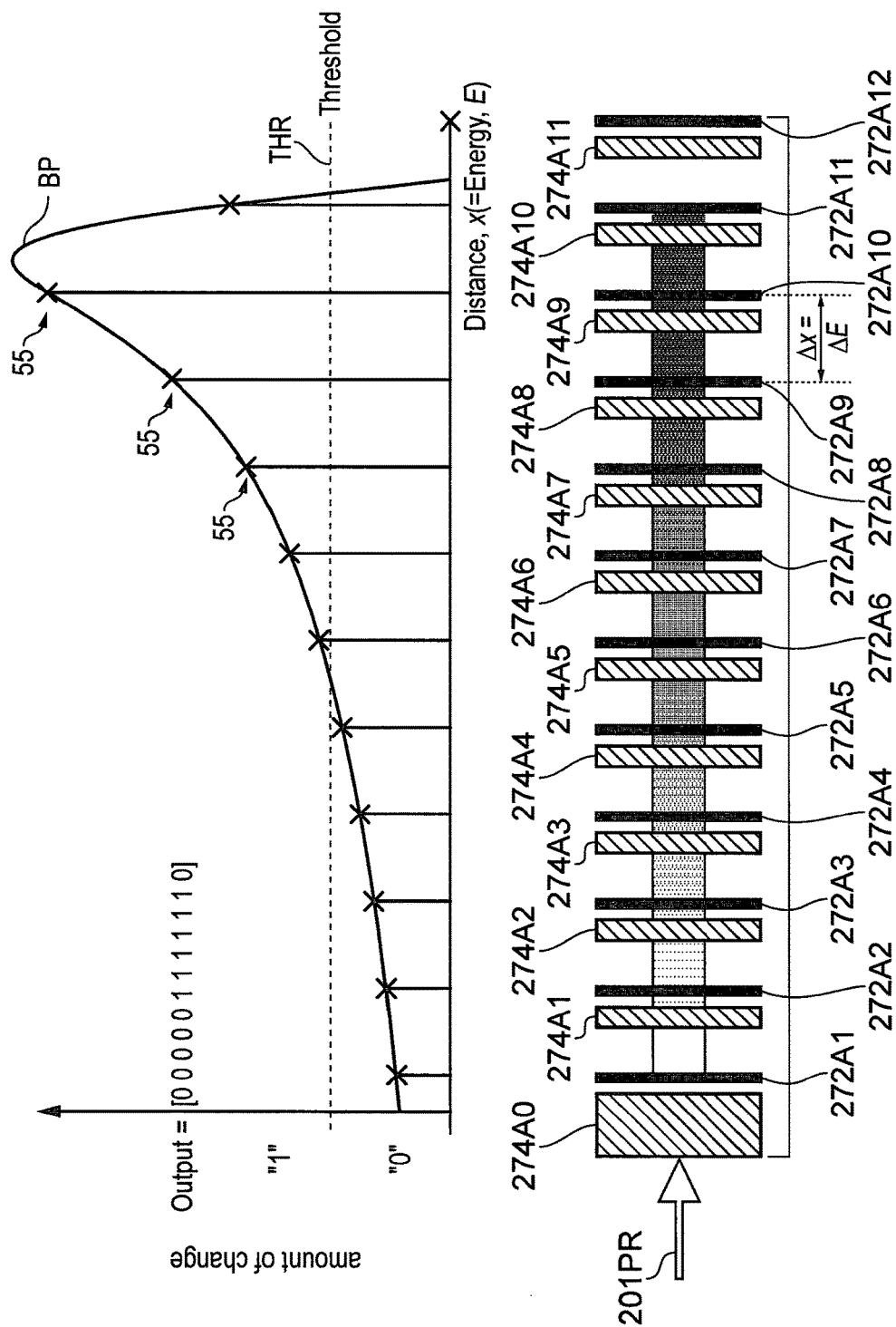
FIG. 13 is a schematic illustration of a range telescope according to an embodiment of the invention in cross-section showing a corresponding plot of an amount of charge generated in a pixel element of each CMOS detector device of the range telescope for a nominal proton passing through the telescope using a homogenous set of detector-absorber modules in the range telescope, the first absorber element being thicker than those downstream in order to effect a more substantial reduction in proton energy before protons interact with detector devices downstream thereof.

FIG. 13 is a schematic illustration of the range telescope 270 with twelve detector devices 272A1-12 mounted within the housing 270H. Above the telescope 270 is shown a plot of the amount of charge generated in a given detector device 272A1-12 as a function of position of the detector device as one particular proton 201PR passes through the telescope 270.

The detector devices 272A1-12 are each configured to produce an output signal that is responsive to an amount of energy lost by a proton 201PR as it passes through the device 272A1-12 and generates charge within the device 272A1-12. The detector devices 272A1-12 are configured to provide a binary output signal each time a proton 201PR is detected. If the amount of charge is below a threshold value THR, a binary '0' signal is generated whilst if the amount of charge is above the threshold value THR, a binary '1' signal is generated.

It is to be understood that the amount of charge generated in a detector device 272A1-12 as a proton passes through the telescope 270 is dependent on the amount of energy absorbed by each detector device. It can be seen from FIG. 13 that a majority of the energy of a given proton 201PR is lost in the region of the Bragg Peak BP towards the end of the proton's travel through the range telescope 270. If the detector devices 272A1-12 each have similar absorption characteristics, and the absorbers 274 also each have similar absorption characteristics, for example by being of substantially uniform composition and thickness, then the energy of a given proton 201PR passing through the telescope 270 can be simply correlated to the distance it travels within the telescope 270.

The range telescope 270 generates an output in the form of a binary string where the elements of a given string are the binary outputs of detector devices 272A1-12. The binary string is generated following each readout or integration period, being the period during which the amount of charge generated in a given detector device 272A1-12 is measured. In the example of FIG. 13, the binary string generated for the illustrated proton absorption event would be [0 0 0 0 0 1 1 1 1 1 1 0]. That is, six detector devices 272A1-12 produce a binary '1' output signal. The beam energy can be estimated by determining the identity of the most downstream CMOS detector device 272A1-12 that generates a binary '1' signal. In the illustrated example, it can be seen that this is the eleventh detector device 272A11.

If absorber element 274A0 is replaced with an element identical to the other absorber elements 274A1-274A11, and each detector-absorber pair (such as absorber 274A1 and detector 272A2) absorb 5 MeV of energy from a proton, the energy of the proton 201PR may be estimated as between 55 MeV and 60 MeV if the same binary output string was output by the detectors, i.e. [0 0 0 0 0 1 1 1 1 1 1 0]. As only a binary signal is produced by each CMOS detector device, in dependence on whether the charge generated in the device 272A1-12 is above a threshold THR, energy resolution is determined by the energy loss across a detector-absorber pair (that is, 5 MeV).

It is to be understood that in order to obtain a finer energy resolution, a larger number of absorber element/detector device pairs may be employed where the absorber elements are of lower absorption. In some embodiments, a relatively thick absorber element 274A0 may be placed at the entrance 270E of the telescope 270 to allow energy measurement over a different range of energies. For example, if the initial absorber-detector pair causes a proton energy loss of 100 MeV and eleven detector-absorber pairs downstream thereof each absorb 5 MeV of energy, the measurement range of the telescope will be 100 MeV to 155 MeV. If the absorbers 274A1-11 between detector devices 272A1-12 (or 'detector planes') have different thicknesses, then measurements can be concentrated over a smaller range. In this way, more measurements can be taken near the Bragg Peak to produce a finer estimate of the beam energy.

Figure 14:
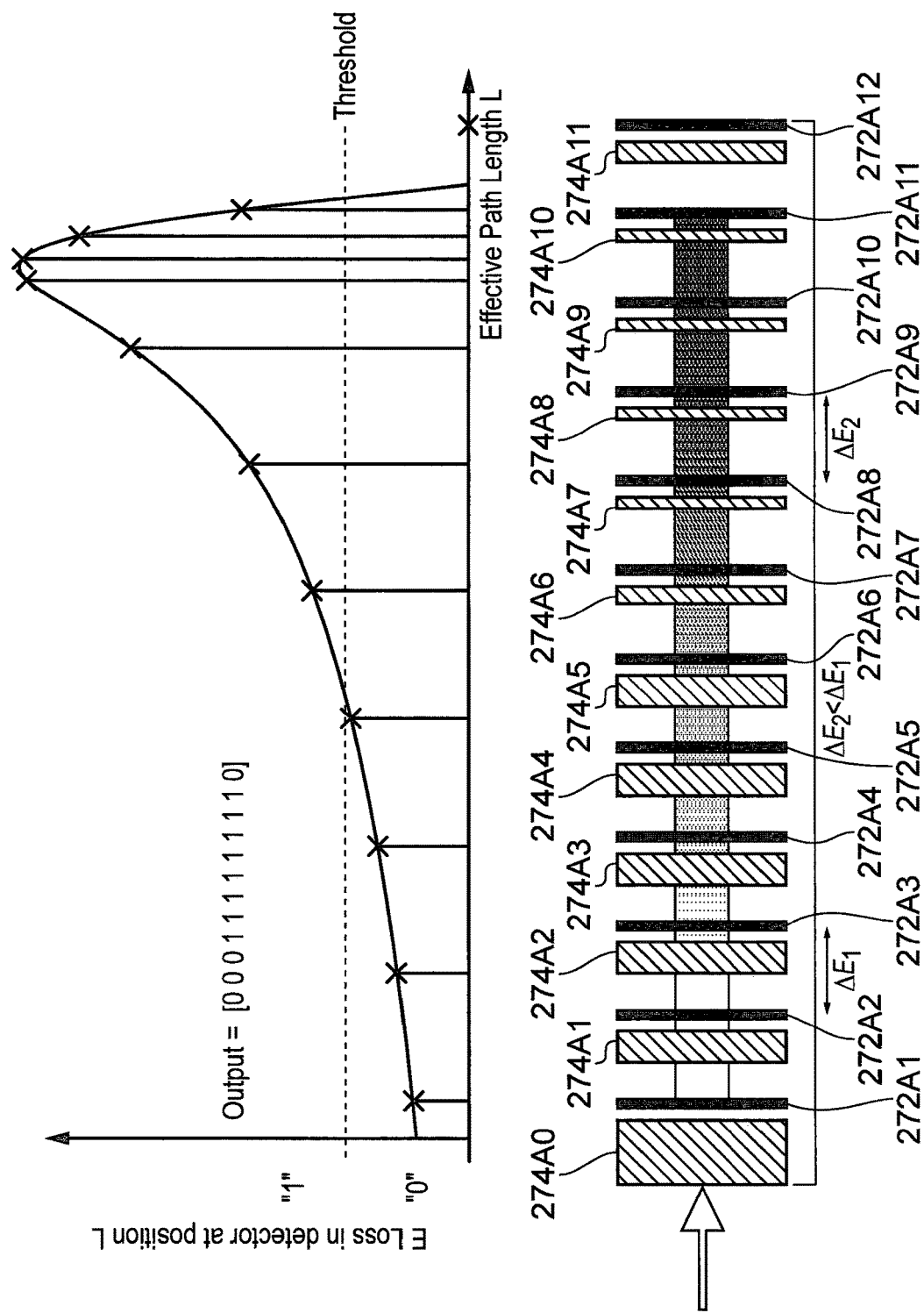
FIG. 14 corresponds to FIG. 13 and is a schematic illustration of a range telescope according to an embodiment of the invention in cross-section showing a corresponding plot of generated charge by a nominal proton as a function of distance using a heterogonous set of detector-absorber modules in the range telescope.

FIG. 14 shows the range telescope 270 of FIG. 14 fitted with absorber elements 274A0-11 of variable thickness. In the example illustrated, the first absorber element 274A0 and detector device 272A1 are configured to absorb a total of 100 MeV of energy. Absorber-detector pairs 274A1, 272A2-274A5, 272A6 are each configured to absorb 5 MeV of energy. Absorber-detector pair 274A6, 272A7 is configured to absorb, say, 3 MeV of energy.

Absorber-detector pairs 274A7, 272A8-274A10, 272A11 are each configured to absorb, say, 2 MeV of energy whilst absorber-detector pair 274A11, 272A12 is configured to absorb 4 MeV of energy. Other arrangements may be useful.

As noted above, the amount of charge generated within a given detector device 272A1-12 as a proton 201PR traverses the range telescope 270 is proportional to the amount of energy lost by the proton as it traverses the telescope 270. That is, protons 201PR of lower energy lose more energy as they pass through a given detector device 272A1-12 compared with protons 201PR of higher energy.

Figure 15:
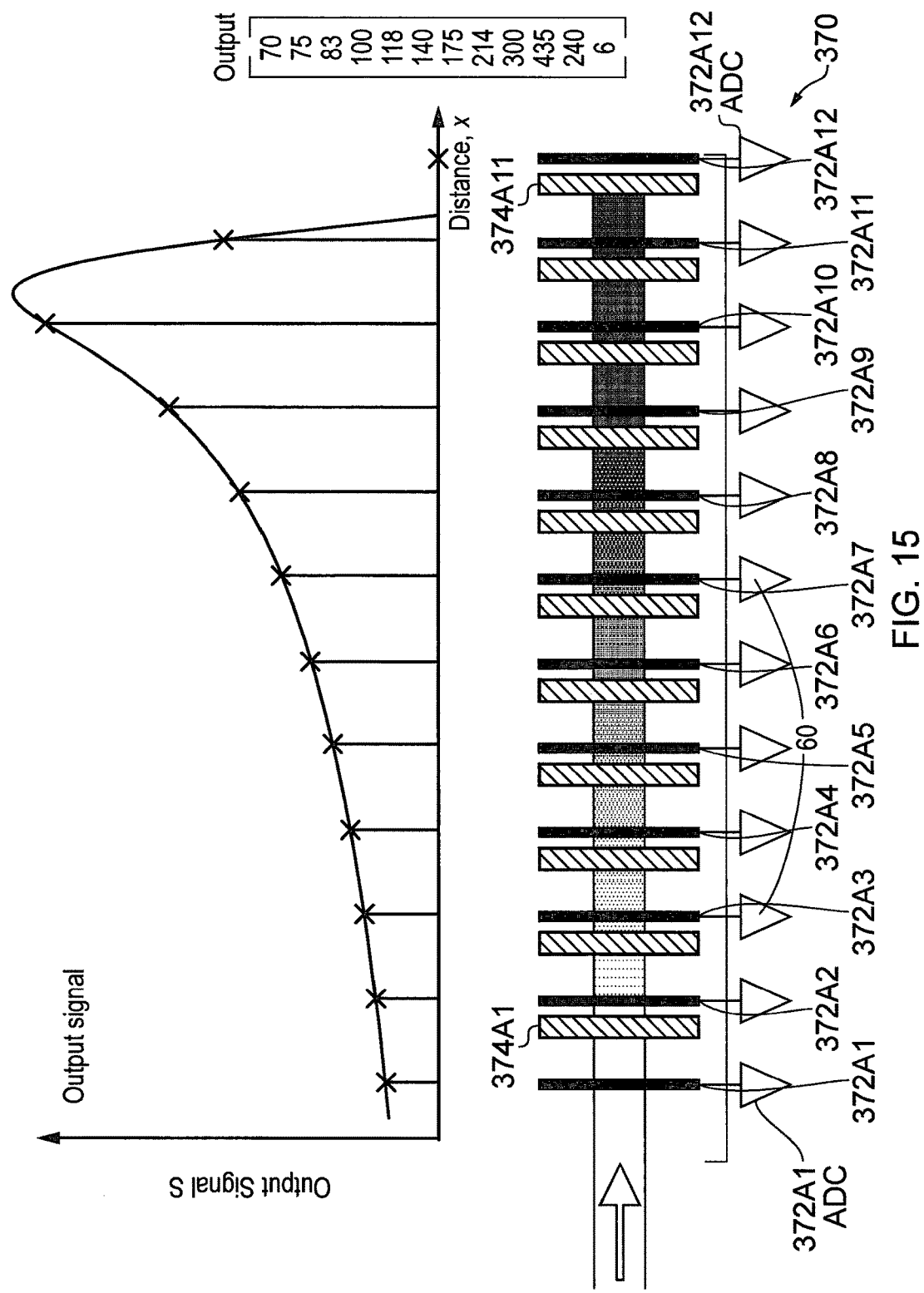
FIG. 15 corresponds to FIG. 13 and shows a range telescope having a homogenous set of detector-absorber modules similar to that shown in FIG. 13 and configured to provide an analogue output in respect of each detector device, the analogue output corresponding substantially to the amount of charge generated in a given pixel element; in the range telescope shown no absorber element is provided immediately upstream of the first detector device although in some embodiments an absorber element is provided immediately upstream of the first detector device.

FIG. 15 illustrates a range telescope 370 according to a further embodiment of the present invention. Like features of the embodiment of FIG. 15 to those of the embodiment of FIG. 5 are shown with like reference signs prefixed numeral 3 instead of numeral 2. In the embodiment of FIG. 15, the output of each CMOS detector device 372A1-12 (corresponding to the amount of charge generated by each photodiode of the CMOS detector device 372A1-12) is passed to a respective analogue to digital converter (ADC) circuit 372A1ADC-372A12ADC. In the embodiment of FIG. 15 the outputs of the detector devices 372A1-12 are digitised at 9-bit resolution, having values in the range 0 to 511, although other arrangements are also useful. Outputting a signal s that is indicative of the amount of charge generated in a given detector device 372A1-12, such as a signal proportional to the amount of charge, rather than a signal simply indicating whether the amount exceeds a threshold value THR, enables much-improved precision in determining the peak energy of the proton beam 201B. It allows interpolation between the discrete values of the amount of charge generated in each detector device 372A1-12 to determine the peak energy. This form of range telescope 370, in which signals proportional to the amount of charge generated in the detector devices is produced, will be referred to as a "hybrid range telescope".

As stated above, in the present embodiment the CMOS detector devices used in range telescopes 270, 370 have two-dimensional arrays of pixels and are radiation-hardened CMOS imaging devices (otherwise known as Active Pixel Sensors). Conventional CMOS circuits are adversely affected by radiation, so the design of the CMOS detector devices used in the range telescopes 270, 370 may incorporate design techniques to mitigate the effects of radiation. For example, enclosed-geometry transistors, guard-rings and inherent redundancy in logic circuits may be employed. Such techniques are widely known in CMOS device design.

The proton beam may have a cross-section that is at least several cm in diameter and this may be further broadened by scattering. Accordingly the active area of the detectors used in the range telescope 270, 370 may be typically 10 cm×10 cm square or larger. Smaller or larger active areas may be useful in some embodiments.

If the apparatus 200 is to be used in a subject imaging mode, then in order to enable the reconstruction of a proton CT image, it is necessary to track individual protons 201PR through the apparatus 200, including through the range telescope 270. Accordingly, CMOS detector devices used in the range telescope 270 (as well as the PSD devices used in the first and second beam tracker structures 210, 220) are operated at relatively high speed, typically many hundreds of frames per second. In typical known CMOS imaging devices, a 2D array of pixel elements is provided in which the pixels are arranged in rows (each row being parallel to an x-axis) and columns (each column being parallel to a y-axis, that is orthogonal to the x-axis). The devices are typically configured to output, in a row by row manner, a signal proportional to the amount of charge accumulated by a photodiode device of each pixel element. An amount of time required to readout the signals from each photodiode device is typically dependent on the number of rows (i.e. the number of pixels per column). For faster readout times this should be kept as small as possible.

Figure 16:
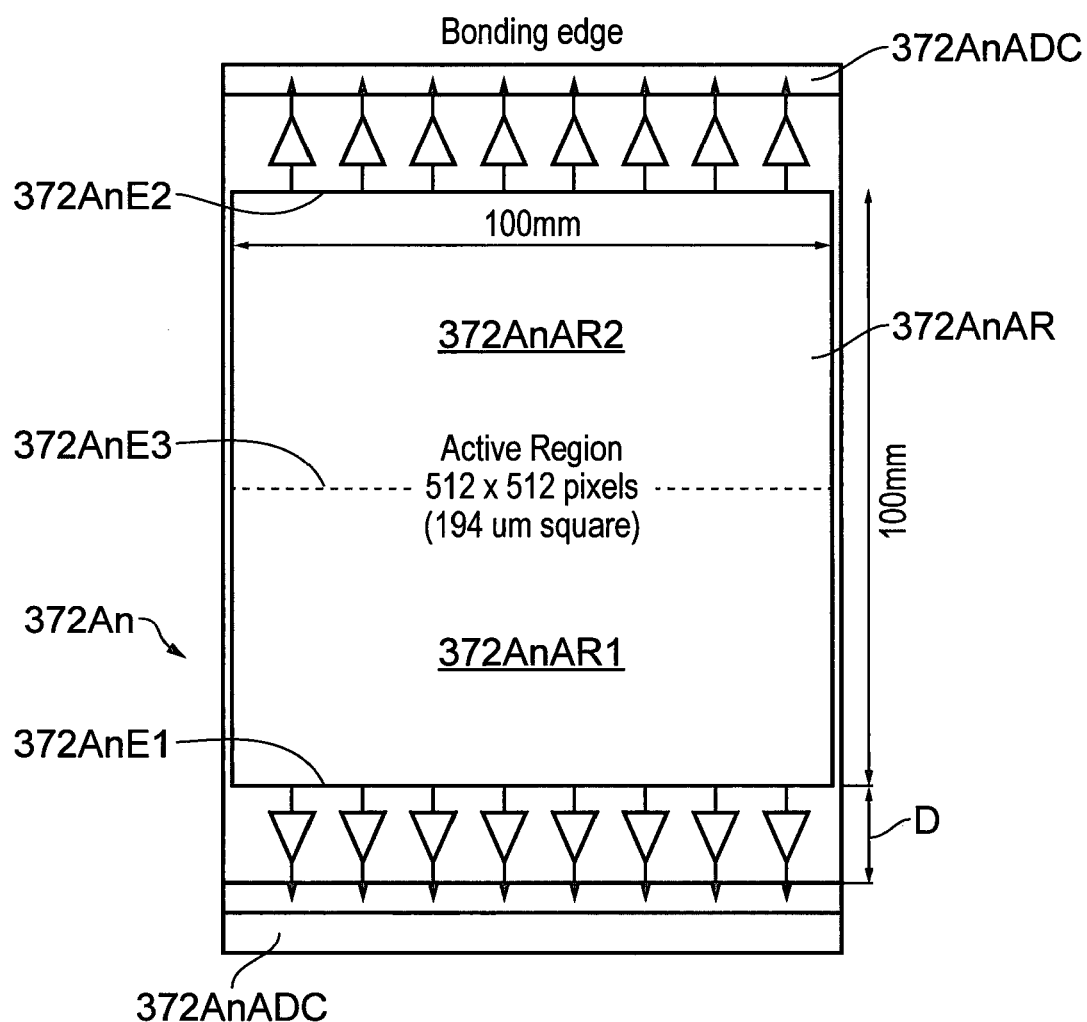
FIG. 16 is a schematic illustration of a CMOS detector device for a range telescope according to an embodiment of the present invention, the detector device being formed from two discrete semiconductor wafers.

FIG. 16 shows a CMOS imager structure of a detector device 372An used in the range telescope 370 of FIG. 15, where n is in the range 1 to 12. The device 372An has an active region 372AnAR having 512 rows of pixel elements, each row containing 512 pixel elements. The device 372An therefore has 512 columns of pixel elements. It is to be understood that in the arrangement of FIG. 16 the active region 372AnAR is split into two portions 372AnAR1, 372AnAR2 such that one half of the pixels (on portion 372AnAR1) provide output signals to respective analogue to digital converter (ADC) circuits along a first edge 372AnE1 of the detector device 372An and the other half of the pixels (on 372AnAR2) provide output signals to respective analogue to digital converter (ADC) circuits along a second edge 372AnE2 of the detector device 372An opposite the first edge 372AnE1. Thus, multiple column readout outputs are provided, in the present embodiment two sets of column readout outputs. In the embodiment of FIG. 16 the two sets of column readout outputs are configured to operate in parallel, i.e. to process signals generated by respective portions 372AnAR1, 372AnA2 of the detector device 372An substantially simultaneously.

It is to be understood that forming the detector device 372An to have two portions 372AnAR1, 372AnAR2, such that the pixel array is split between two dies (i.e. between two semiconductor substrates), has the advantage that a manufacturing yield of detector devices 372An may be increased. The portions 372AnAR1, 372AnAR2 are formed such that abutting edges 372AnE3 of the respective portions 372AnAR1, 372AnAR2 are fine-grained with effectively substantially no loss of coverage in terms of active area.

A distance D between the active area 372AnAR of the detector device 372An and a peripheral edge of the detector device 372An may be set to a value sufficiently large to reduce exposure of peripheral data processing circuits to radiation, such as the analogue to digital circuits 372AnADC. In the embodiment of FIG. 16 substantially all connections to the active areas 372AnAR are situated along one bonding edge 372AnE1, 372AnE2 of each portion 372AnAR1, 372AnAR2. Due to the inherent lateral scatter of the protons, the individual pixel size may advantageously be relatively large (typically 100 um to 200 um square).

The range telescopes 270, 370 described herein are configured to allow exchange of the absorber elements with absorber elements of different absorption cross-sections. The range telescopes 270, 370 are modular in construction, allowing a range telescope of substantially any required length to be fabricated. The telescopes 270, 370 are formed by coupling telescope module portions 270M (FIG. 17) together in an end to end configuration along a direction of propagation of protons 201PR through the telescopes 270, 370. The construction of module portions 270M of the range telescope 270 of FIG. 13 will now be described. It is to be understood that the construction of the range telescope 370 of FIG. 15 is similar with respect to modular construction and the discussion of modules 270M or the range telescope 270 of FIG. 13 is also applicable to the range telescope 370 of FIG. 15.

Figure 17:
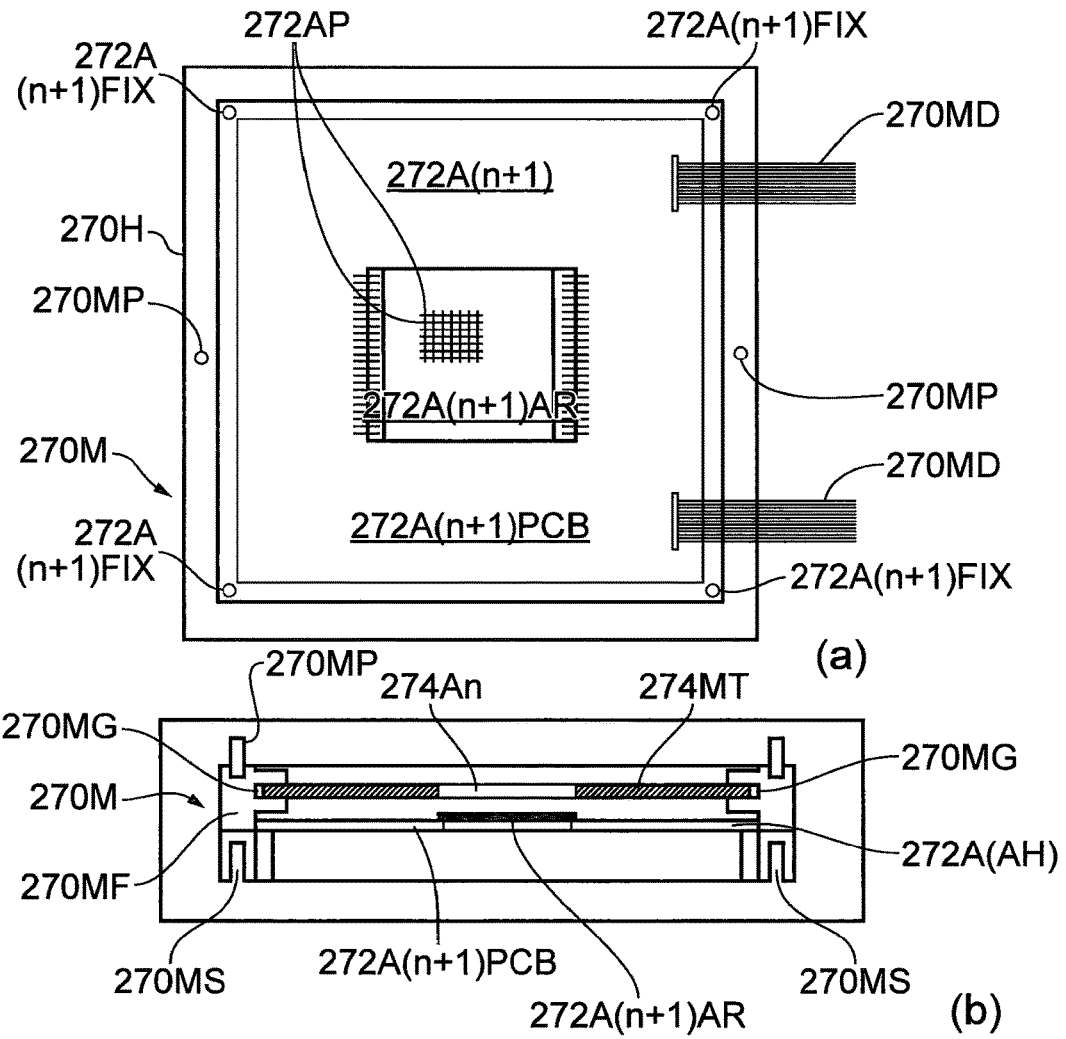
FIG. 17 is a schematic illustration of a telescope module portion for a range telescope according to an embodiment of the present invention.

FIG. 17 shows an example of a telescope module portion 270M that forms part of a stack of module portions 270M comprised by the range telescope 270 of FIG. 5. The module portion 270M is shown in plan view in FIG. 17(a). A front cross-sectional view is shown in FIG. 17(b).

The module portion 270M includes an absorber element 274An and a CMOS detector device 272A(n+1) comprising an array of pixels or pixel elements 272AP. The CMOS detector device 272A(n+1) has an active region 272A(n+1)AR provided by a CMOS imaging device mounted on a PCB 272A(n+1)PCB that also carries supporting electronics for data acquisition. The PCB 272A(n+1)PCB is in turn mounted within a precision metal frame 270MF. Electrical connections are provided between the PCB 272A(n+1)PCB and the range data processing system 270DP by means of ribbon cables 270MD.

Figure 18:
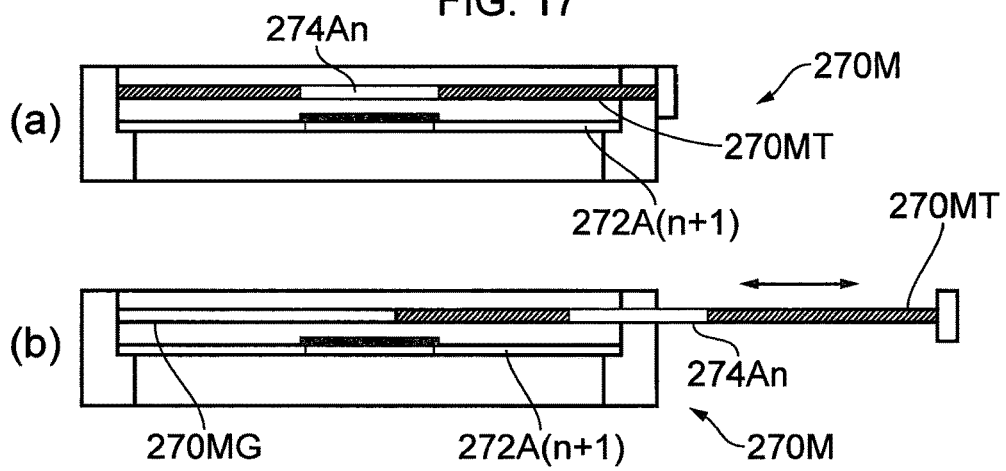
FIG. 18 is a schematic illustration (a) of the telescope module portion of FIG. 17 viewed along a direction orthogonal to that of the view of FIG. 17 showing a slidable holder for holding an absorber portion in a closed position, (b) the arrangement shown in (a) with the slidable holder in an open position, (c) a compound range telescope having strip detector devices interleaved with CMOS detector devices, (d) strip detector devices of the range telescope shown in (c) showing a substantially equal rotational increment angle between successive strip detector devices, in the present embodiment substantially 30 degrees (180/6), (e) a range telescope according to an embodiment of the invention in which three strip detector modules, each comprising a pair of crossed strip detectors, are provided such that two CMOS detector devices are provided between the middle strip detector module and each module upstream and downstream of the middle module, and (f) a portion of a range telescope according to an embodiment of the invention having a pair of strip detector modules with three CMOS detector devices sandwiched therebetween, showing a path of a proton through the telescope during (i) a first readout period of the strip detector module and (ii) a second readout period of the strip detector module immediately following the first readout period referred to in (i)

As shown in FIG. 18, the module portion 270M has removable trays 270MT running in guides 270MG that allow the trays 270MT to be introduced into the range telescope 270M. FIG. 18(a) is a cross-sectional side view of the module portion 270M with the tray 270MT in a closed position whilst FIG. 18(b) is a corresponding cross-sectional side view of the module portion 270M with the tray 270MT in an open position. The trays 270MT are arranged to support absorber elements 274An therein. The trays 270MT allow absorber elements 274An of different thicknesses to be interchanged readily, enabling adjustment of the range of energies of protons that the range telescope 270, 370 may detect and the energy resolution of the range telescope 270, 370 over the required range.

In the embodiments described herein, the removable absorber elements 274An are formed from polymethyl methacrylate (PMMA) or other suitable material (e.g., polyethylene). As noted above, the absorber elements 274An can be of different respective thicknesses. For example, absorber elements of lower thickness may be provided in the region of the telescope 270, 370 where the Bragg Peak is expected to occur, i.e. the location of the region of peak proton absorption, so enabling a better estimate of the Bragg Peak profile to be obtained.

The frame 270MF of the module 270M is configured to allow the PCB 272A(n+1)PCB of the CMOS detector device 272A(n+1) to be mounted substantially rigidly thereto by means of screw fixings 272A(n+1)FIX.

It is to be understood that the modules 270M may be precisely aligned mechanically by means of precision metal pins 270MP that project from a first side of the modules 270M and matching location holes or sockets 270MS that are formed in a second side of the modules 270M opposite the first. In the present embodiment, placement of position-critical components including the trays 270MT for the absorber elements 274An and detector device PCB 272A(n+1)PCB, are referenced to these pins.

In the present embodiment the correct position of the active region 272A(n+1)AR of the detector with respect to the metal frame 270MF of the module 270M is identified by means of fiducial markers provided on the surface of the semiconductor wafers during processing thereof. The pins 270MP are then employed in the assembly of the modules 270M to form a stack of modules 270M.

In some alternative embodiments, the CMOS detector devices of the range telescope 270, 370 may be replaced by sets (such as pairs or triplets) of strip detector devices such as devices similar to those used in the first and second beam tracker structures 210, 220. Other arrangements may also be useful in addition or instead.

Figure 18C:
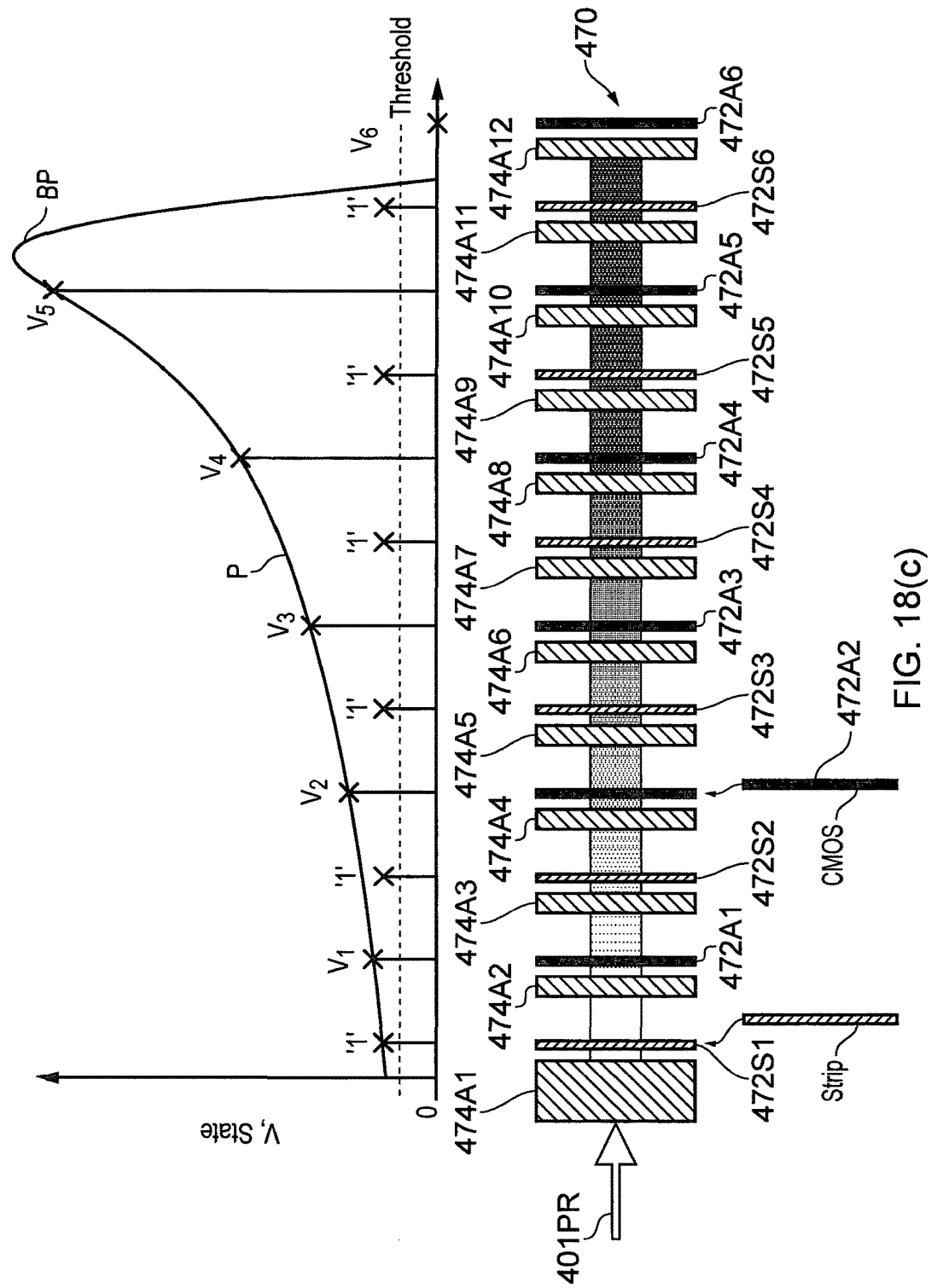

In some embodiments strip detector devices similar to those used in the first and second beam tracker structures 210, 220 may be employed in range telescopes according to embodiments of the present invention in addition to CMOS detector devices 272An. Such range telescopes may be referred to as compound range telescopes. FIG. 18(c) illustrates schematically an arrangement of strip detector devices 472Sn and CMOS detector devices 472An in a compound range telescope 470 according to a further embodiment of the present invention.

As can be seen from FIG. 18(c), the range telescope 470 has six strip detector devices 472Sn and six CMOS detector devices 472An arranged in an alternating configuration beginning with a first strip detector device 472S1 at an upstream end of the range telescope 470 with respect to a direction of travel of protons 472PR through the telescope 470. An absorber element 474A is provided upstream of each detector device 472Sn, 472An. In the embodiment illustrated in FIG. 18(c) absorber elements 474A2-474A12 have a similar absorption cross-section or WEPL to one another whilst first absorber element 472A1 upstream of the first detector device (first strip detector device 472S1) has a greater WEPL. This is in order to reduce the energy of protons to a value sufficiently low to ensure that a sufficient number of protons will be absorbed within the range telescope 470 This feature allows the absorber elements 474A2-474A12 downstream of the first absorber element 474A1 to be of lower WEPL in order to increase the resolution of the telescope 470, i.e. to reduce the uncertainty in proton energy determined by the telescope 470. As described above, the lower the WEPL of the absorber elements 474An in the region of the telescope in which absorption takes place, the lower the uncertainty in proton energy.

The strip detector devices 472Sn are similar to the solid-state strip detector devices 210A1, 210A2, 210A3, 210B1, 210B2, 210B3 employed in the first beam tracker structure 210 of the embodiment of FIG. 4. Each strip detector device 472Sn comprises an array of semiconductor strip elements 472SnSTR formed on a semiconductor substrate in a similar manner to the strip detector device 210A1 illustrated in FIG. 8(a) and FIG. 10.

Figure 18D:
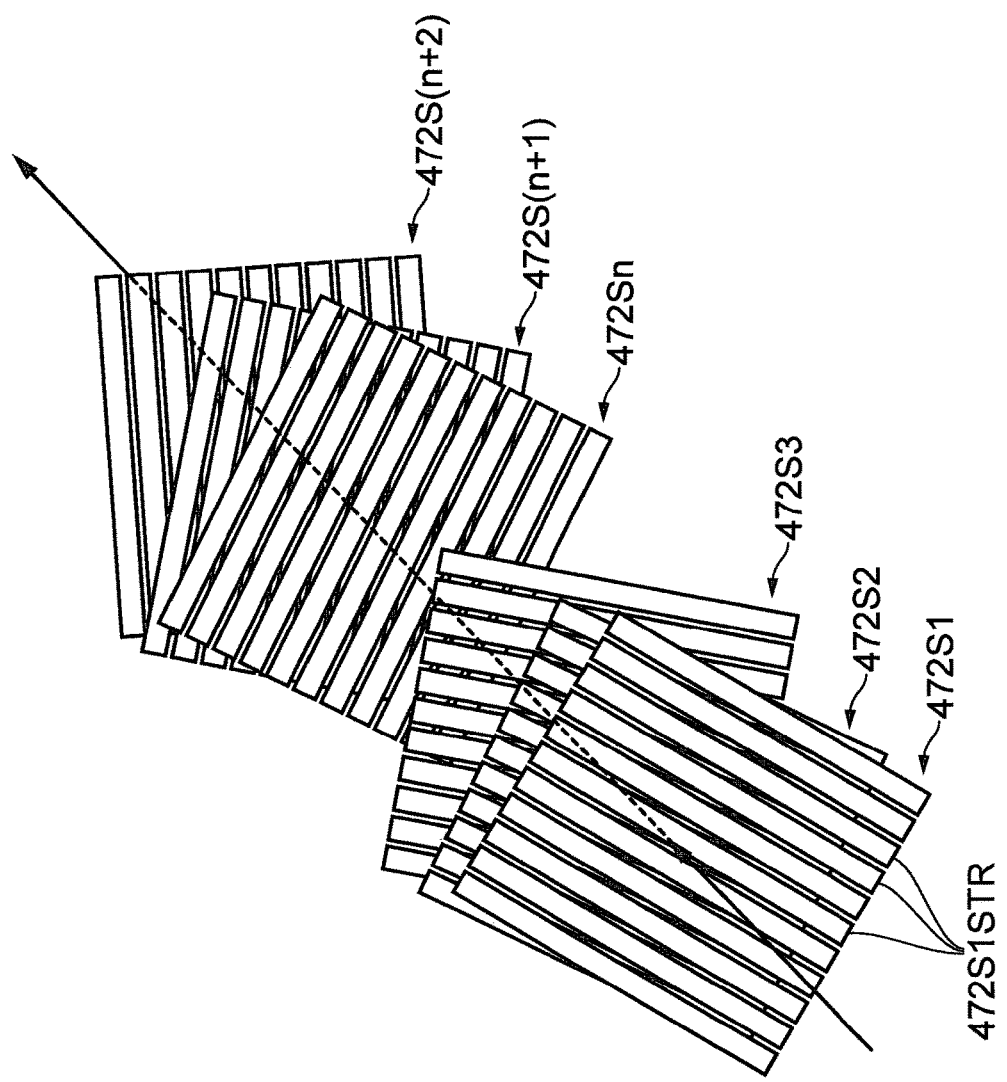

The longitudinal axes of the strip elements 472SnSTR of respective strip detector devices 472Sn are non-parallel and arranged such that the longitudinal axis of each successive strip detector device 472Sn is rotated by a substantially fixed angle relative to the preceding device 472Sn as illustrated schematically in FIG. 18(d). In the embodiment of FIG. 18(c) the range telescope 470 has six strip detector devices 472Sn and the longitudinal axes of successive devices 472Sn are rotated by substantially (180/6=60) degrees with respect to the preceding device 472Sn.

In some alternative embodiments, a group of two or more strip detector devices 472Sn may be provided at the location of each strip detector device 472Sn illustrated in FIG. 18(c) rather than only one. This features enables the 2D position, with respect to the active area of a given strip detector device 472Sn, at which a proton passes the location of a given group of devices 472Sn to be determined with greater precision, enabling the location at which a given proton detected by the strip detector devices 472Sn passed through each CMOS detector device 472An to be determined with greater precision. This enables more accurate tracking of protons through the telescope 470, thereby enabling the energy of individual protons to be determined more reliably, as discussed in more detail below.

Figure 18E:
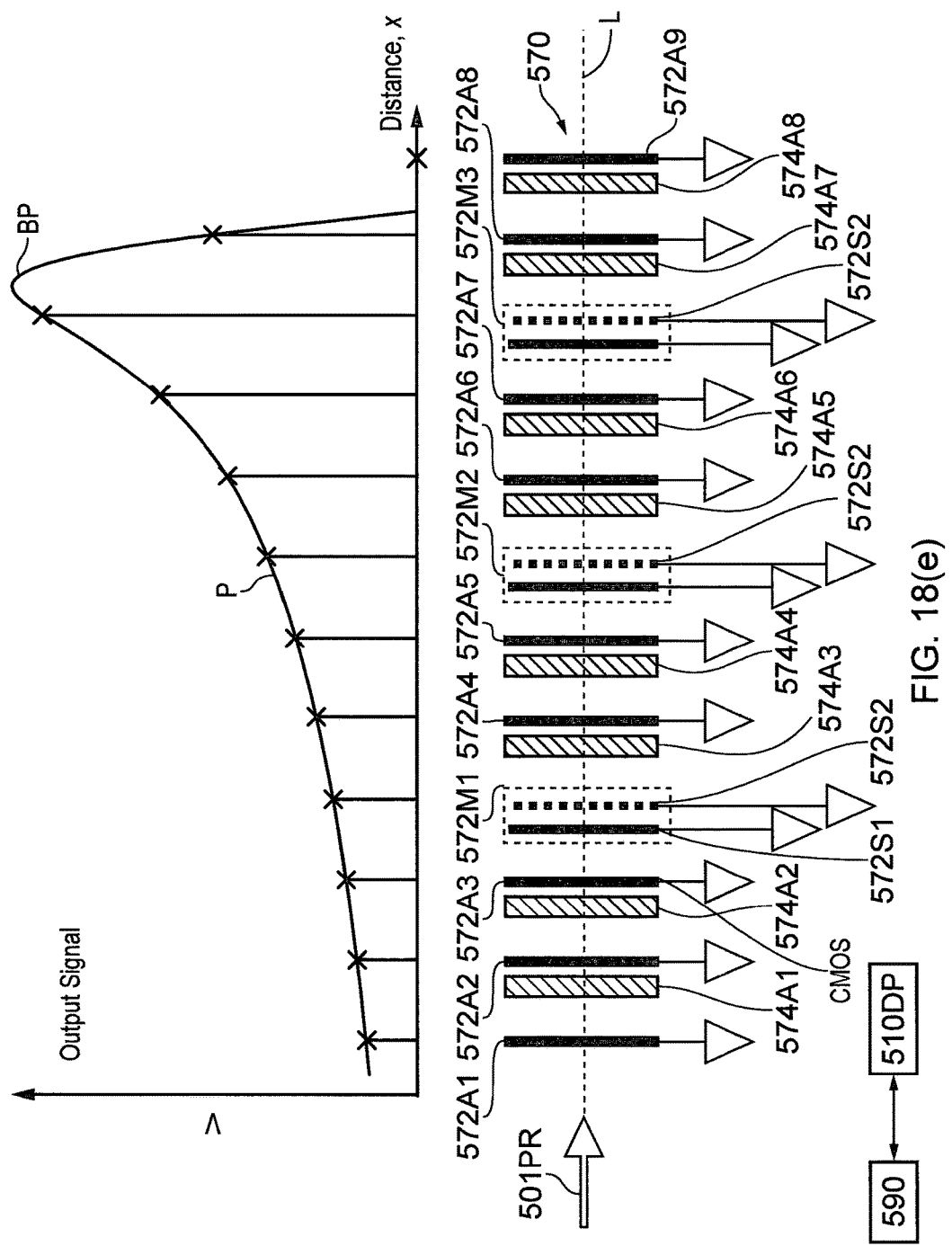
Figure 18F:
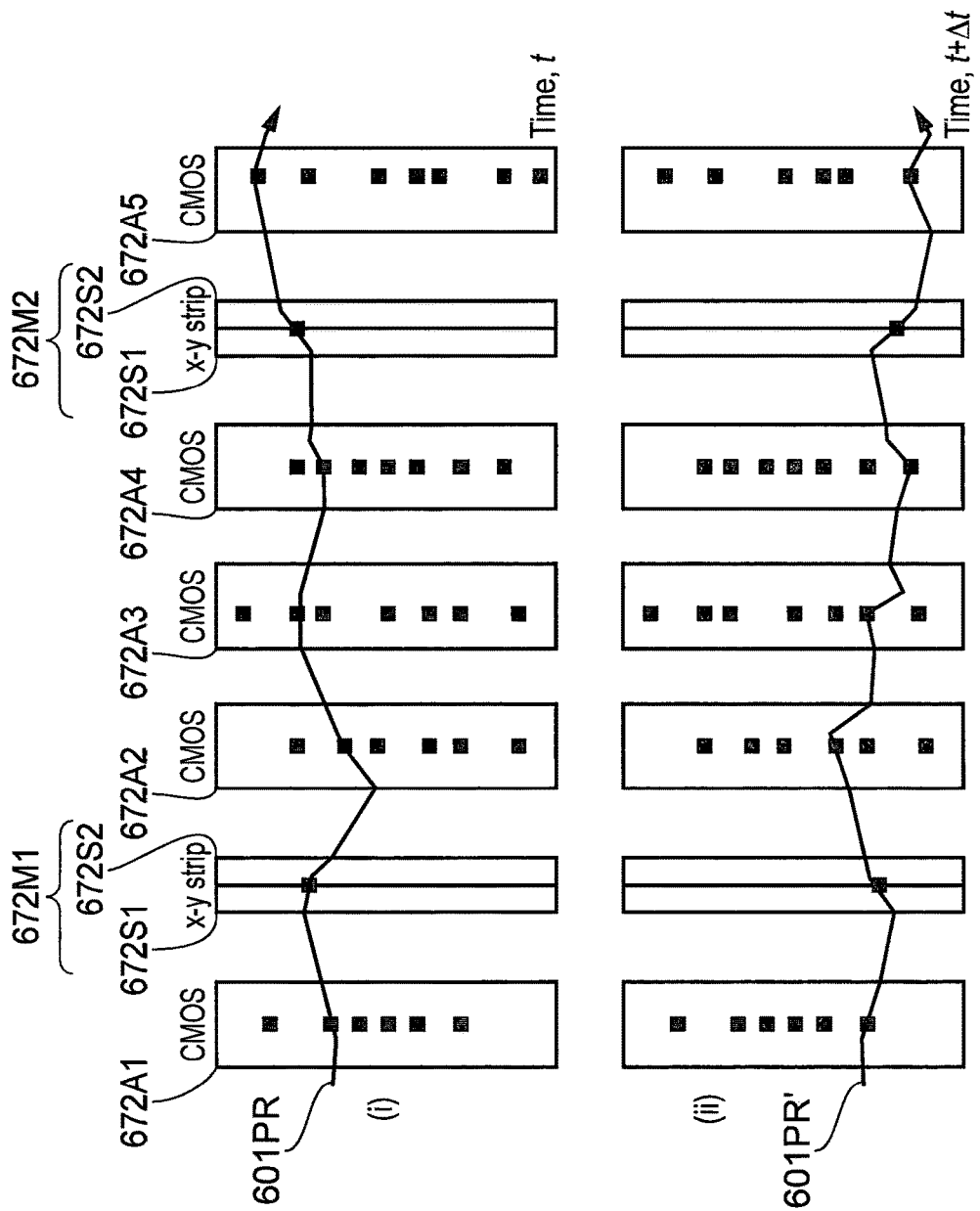

FIG. 18(e) illustrates a range telescope 570 according to a further embodiment of the invention. Like features of the embodiment of FIG. 18(e) to those of the embodiment of FIG. 18(d) are shown with like reference signs incremented by 100. In the embodiment of FIG. 18(e) nine CMOS detector devices 572An are provided in a substantially coaxial arrangement with respect to a longitudinal axis L of the telescope 570. A strip detector module 572Mn is provided between adjacent CMOS detector devices 572An at three locations along the longitudinal axis with two CMOS detector devices 572An between each strip detector module 572S. The strip detector modules 572S each comprise a pair of crossed strip detector devices 572S1, 572S2. The strip detector devices 572S1, 572S2 are similar to the devices 472Sn of the embodiment of FIG. 18(c) which are in turn each similar to the strip detector device 210 illustrated in FIG. 8(a). A first of the strip detector devices 572S1 is oriented with longitudinal axes of the strips thereof substantially vertical with respect to the illustrated arrangement, whilst a second of the strip detector devices 572S2 is oriented with longitudinal axes of the strips thereof substantially horizontal with respect to the illustrated arrangement.

Three CMOS detector devices 572A1-A3 are provided upstream of a first strip detector module 572M1, two CMOS detector devices 572A4-A5 are provided between the first and a second strip detector module 572M2 and two CMOS detector devices 572A6-A7 are provided between the second and a third strip detector module 572M3. Two further CMOS detector devices 572A8-A9 are provided downstream of the third strip detector module 572M3.

The spacing between immediately adjacent devices 572An, 572Mn is substantially uniform along the longitudinal axis of the telescope 570 although in some embodiments one or more spacings may be different. Thus in the embodiment of FIG. 18(e) a spacing CMOS detector devices 572A1-A3 is substantially the same, and substantially equal to the spacing between CMOS detector device 572A3 and the first strip detector module 572M1, and between the first strip detector module 572M1 and fourth CMOS detector device 572A4.

As shown in FIG. 18(e) an absorber element 574An is provided immediately upstream of each of CMOS detector devices 572A2-A9.

In the embodiment of FIG. 18(e) the CMOS detector devices 572A1-A9 and strip detector modules 572M1-M3 are connected to an associated range data processing system 570DP which is in turn connected to a primary control device 590 in a similar manner to the embodiment of FIG. 4. The range data processing system 570DP is configured to receive a signal from each of the CMOS detector devices 572A1-A9 corresponding to a location within a 2D active area, defined by the array of CMOS photodiode devices of each CMOS detector device 572A1-A9, at which a proton is detected by each CMOS detector device 572A1-A9.

The range data processing system 570DP also receives a signal from each strip detector module 572M1-M3 indicative of a 2D location within an active area defined by each module 572M1-M3 at which a proton has been detected passing through the respective module 572M1-M3. In the present embodiment the modules 572M1-M3 are configured to output data to the data processing system 570DP at intervals corresponding to the pulse period of the proton source. In the present embodiment the pulse period is around 50 ns but other periods may be useful. The CMOS detector devices 572A1-A9, in contrast, are configured to output data to the data processing system 570DP at intervals of 1 ms in the present embodiment although other intervals may be useful in some embodiments. The ability to employ readout periods as low as those accessible using strip detector modules reduces confusion in respect of the tracking of non-linear paths through the range telescope 570 to the distance between adjacent strip detector modules 572M1-M3, having two CMOS detector devices 572An therebetween in the present embodiment. Consequently, a greater number of particles can be present in the range telescope 570 within the time period that the CMOS detector devices 572A1-A9 (CMOS imagers) gather data and the paths of a substantial majority of the particles tracked sufficiently accurately. This, in term, means that the total time to record sufficient particles to create a CT image is reduced.

In creating images, both planar images (obtained by recording an image with a subject at a single angle with respect to the beamline) and CT images (obtained based on planar image data at multiple angles), it is necessary to know the entrance and exit position of a particle as it passes through a patient, together with its residual energy upon exiting the patient (and entering the range telescope). Hence it is necessary to track the non-linear paths of particles as they pass through the range telescope and release their energy. As the number of particles in the range telescope during the readout period of the CMOS detector devices 572A1-A9 increases (for example due to an increase in the flux of particles generated by the particle source) then there is an increasing probability that individual tracks can not be reliably followed.

Successive immediately adjacent devices 572An and modules 572Mn moving along the longitudinal axis L may be considered to represent successive layers, with device 572A1 representing a first layer, absorber element 574A1 in combination with device 572A2 representing a second layer, absorber element 574A2 in combination with device 572A3 representing a third layer, strip detector module 572M1 representing a fourth layer and so forth.

Particles may be considered to be scattered at each layer with a distribution that is essentially Gaussian. Accordingly, one relatively simple approach to particle tracking is to consider a particle at position (x,y) in layer N. The most likely position of the particle in layer (N+1) is (x+$\Delta$x, y+$\Delta$y) where ($\Delta x^2 + \Delta y^2$) is minimized. Extensive simulations by the present applicant suggests that for 1,000 particles in 1 ms and over 24 layers, then over 85% of particles can be reliably tracked.

More complicated algorithms can be employed to improve reliability of tracking over this simple approach. For example, methods used by computer scientists in tracking movement of people or vehicles, where a most likely path is estimated by considering all layers simultaneously, rather than pair-wise as discussed above It is to be understood that, as discussed above, the CMOS detector devices 472An typically have a much slower rate of output in respect of the identity of pixel elements (typically each comprising a photodiode device under reverse bias) than the strip detector devices. That is, the time required to read out the identity of a pixel element of a CMOS detector device 472An experiencing a hit is much greater than the time required to read out the identity of a strip that has experienced a hit. Accordingly, the strip detector devices 472Sn are employed to provide relatively fine time resolution whilst the CMOS detector devices 472An are employed to provide analogue values indicative of the amount of charge carriers generated in each pixel element due to passage of a proton therethrough. This enables more protons to be tracked unambiguously through the range telescope 470 in a given time frame, reducing the time required to acquire a CT image. This in turn may be employed to reduce the proton dose received by a subject whilst acquiring a CT image. It is to be understood that in some embodiments a reduction in the time required to obtain a full scan from 60 minutes to around 5 minutes may be achieved.

Above the illustration of the range telescope of FIG. 18(c) is plotted an indication of the amount of charge generated in a given pixel of each CMOS detector device 472An as one particular proton 401PR passes through the telescope 270, and an indication of whether each strip detector device 472Sn experienced a proton hit (indicated by parameter STATE, being '1' in the case of a hit by a given detector device 472Sn and '0' in the absence of a hit). The amount of charge generated in a given pixel of each CMOS detector device 472An is indicated by potential V, measured across the photodiode comprised by the respective pixel experiencing the hit.

As described above, it is to be understood that the amount of charge generated in a detector device 472An as a proton passes through the telescope 470 is dependent on the amount of energy absorbed by each detector device. It is to be understood that a majority of the energy of the proton 401PR is lost in the region of the Bragg Peak BP towards the end of the proton's travel through the range telescope 470. Since the detector devices 472A1-12 each have similar absorption characteristics, and the absorbers 474A2-A12 also each have similar absorption characteristics (being of substantially uniform composition and thickness), then the energy of a given proton 401PR passing through the telescope 470 can be simply correlated to the distance it travels within the telescope 470.

The strip detector devices 472S1-S6 are employed to generate an output in the form of a binary string indicating whether or not a proton 401PR has been detected passing through each device 472S1-S6. The binary string is generated following each readout or integration period of the devices 472S1-S6, being the period during which the amount of charge generated in a given detector device 472S1-S6 is measured. In the example of FIG. 18(c), the binary string generated for the illustrated proton absorption event would be [1 1 1 1 1 1]. That is, each of the six strip detector devices 472S1-S6 produce a binary '1' output signal.

The strip detector devices 472S1-S6 also provide an output indicative of the identity of the strip 472SnSTR that has experienced a hit, enabling correlation of hit data from the strip detector devices 472S1-S6 and hit data from the CMOS detector devices 472A1-A6. This in turn enables the trajectories of protons passing through the range telescope to be determined with greater confidence. That is, the location at which an individual proton passes through each CMOS detector device 472A1-A6 may be determined with greater confidence.

It is to be understood that the CMOS detector devices 472A1-A6 allow relatively fine energy resolution in terms of determining the energy of a given proton by identifying the position of the Bragg peak. This is at least in part because the amount of charge deposited in a pixel element of a given CMOS detector device 472A1-A6 is dependent on the energy of the proton. Furthermore, the position of the proton with respect to a 2D active area of the detector device 472A1-A6 may be determined without a requirement to deconvolve proton position by reference to three or more strip detector devices.

FIG. 18(*f*) further illustrates operation of a range telescope device having both CMOS detector devices and strip detector devices. In each of FIGS. 18(*f*)(*i*) and 18(*f*)(*ii*), a portion of a range telescope according to an embodiment of the present invention is shown in side view. Like features of the embodiment of FIG. 18(*f*) to those of the embodiment of FIGS. 18(*c*) and (*e*) are shown with like reference numerals incremented by 100. In the portion of the range telescope illustrated, a pair of strip detector modules 672M1, 672M2 are shown bracketing three CMOS detector devices 672A2-A4.

A further CMOS detector device 672A1 is provided upstream of first detector module 672M1, with respect to a direction of proton flux through the range telescope, and one CMOS detector device 672A5 is shown downstream of the second strip detector module 672M2.

Absorber elements (not shown) are located in front of (upstream of) each device 672An and module 672Mn.

In FIG. 18(*f*)(*i*), solid squares within each CMOS detector device 672An and detector module 672Mn show an example of the locations (in side view) at which individual protons pass through each device 672An during a single readout period of each respective CMOS detector device 672An and through each module 672Mn during a single readout period of the modules 672Mn that falls within the readout period of the CMOS detector devices 672An illustrated. As described herein, the readout period for each strip detector module 672Mn (50 ns in the embodiment shown) is much smaller than that for each CMOS detector device 672An (1 ms in the embodiment shown). Accordingly, the number of protons passing through each strip detector module 672Mn during a given readout period of the module 672Mn is much lower than that for a given CMOS detector device 672An during its corresponding readout period. In the example of FIG. 18(*f*) a single proton passes through each strip detector module 672Mn during the readout period for which the locations of proton passage through a given module 672Mn are shown. It is to be understood that, in some embodiments, the proton flux is sufficiently low that the likelihood of more than one proton being detected by the strip detector modules 672Mn during a given readout period is low.

FIG. 18(*f*)(*ii*) shows the locations (in side view) at which individual protons pass through each CMOS detector device 672An during the same readout period thereof as shown in FIG. 18(*f*)(*i*) is shown, together with the locations at which a single proton passed through the detector modules 672Mn during the subsequent module readout period to that shown in (i).

The coordinates (typically (x, y) coordinates) of protons passing through the respective strip detector modules 672M1, M2 define a unique proton path, and it is desirable to determine the corresponding locations at which the proton passed through the intervening CMOS detector devices 672A2-A4. Since the presence of the strip detector modules 672Mn enables the location at which a proton passes the location of each module 672Mn to be determined, the corresponding events in the intervening CMOS detector devices 672A2-A4 can be determined with greater confidence than in the absence of the modules 672Mn.

It is to be understood that the uncertainty in following a path through the CMOS detector devices 672An obeys binomial statistics. The uncertainty in following a path through the CMOS detector devices 672An falls rapidly as the number of layers of devices, whether CMOS detector devices 672An or strip detector devices 672S increases.

In an alternative embodiment, instead of providing strip detector modules 672Mn, a single strip detector device 672S1 with a single array of strip elements is provided at the location of module 672M1 shown in FIG. 18(*f*) and a single strip detector device 672S2 is provided at the location of module 672M2. In the arrangement of FIG. 18(*f*) the respective strip detector devices 672S1, 672S2 at the location of modules 672M1, 672M2 of FIG. 18(*f*) are arranged such that the longitudinal axes of the strip elements of the respective detector devices 672S1, 672S2 are substantially orthogonal to one another. In such an embodiment, the combination of the two strip detector devices 672S1, 672S2 enables an (x, y) coordinate of particle location to be determined, enabling a reduction in uncertainty in the determination of particle path through the range telescope. It is to be understood that in the case that strip detector modules are employed, the use of more than two detector devices 672S in each module may not provide a substantial increase in the certainty with which the location of a particle passing through the module may be determined in cases where the flux of particles through the apparatus is sufficiently low that the probability of two particles passing through the strip detector module during a single readout period is relatively low. It is to be understood that this will typically be the case within the range telescope due to the relatively low particle fluxes used during the conduction of CT scans. In contrast, during periods when the apparatus is used to treat a subject with particles, where the Bragg peak of particle absorption is arranged to coincide substantially with a volume of a subject to be treated such as a brain tumour, the flux of particles is typically much higher. Accordingly the flux of particles through the first beam tracker structure 210 of the apparatus is relatively high, such that the probability of more than one particle passing through the strip detector devices in a single readout period is much higher. The first beam tracker structure 210 is therefore advantageously provided with more than two strip detector devices 210An, such as three strip detector devices 210A1-A3, having mutually non-parallel strip elements 210AnSTR, enabling a more reliable determination of the coordinates of particles passing through the structure 210 during a given readout period.

Overall Assembly

FIG. 19 is an overall schematic illustration of the apparatus 200 of FIG. 11 incorporating the range telescope 370 illustrated in FIG. 15.

The first and second beam tracker structures 210, 220 and range telescope 370 are mounted in a substantially rigid, precision frame 200F that permits careful alignment of the apparatus 200 with a proton beam 201B, the subject 201S

(such as a patient) and other apparatus associated with a proton therapy system 200SYS.

The frame 200F offers relative motion of the apparatus 200 and the subject 201S. In the present embodiment, the apparatus 200 is arranged to move the subject 201S whilst in some alternative embodiments the apparatus 200 is arranged to move with respect to the subject 201S. The frame 200F is carefully aligned to the incoming portion of the proton beam 201Bin, i.e. with beam 201B as it approaches the frame 200F.

As shown in FIG. 19, the apparatus 200 has first, second and third absorber element devices 230A1-3 positioned upstream of the range telescope 370 and arranged in series along a direction of travel of the beam 201B.

The first absorber element device 230A1 has a pair of wedge-shaped absorber portions 230A1a, 230A1b. The absorber portions 230A1a, 230A1b are configured to be moved towards and away from one another so as to vary an amount of overlap of the portions 230A1a, 230A1b with respect to a direction of propagation of the proton beam 201B. This allows the first absorber element device 230A1 to exhibit an absorption characteristic that is substantially continuously variable in magnitude. This in turn allows an operator to determine the range of energies of protons 201PR that are to be permitted to enter the telescope 270. In the present embodiment the absorber portions 230A1a, 230A1b are in sliding contact with one another although in some alternative embodiments they are spaced apart from one another with respect to a direction of propagation of the beam 201B.

The second and third absorber element devices 230A2, 230A3 are of differing thicknesses and positioned between the first absorber element device 230A1 and the range telescope 370. The purpose of the second absorber element device 230A2 is to block incident protons from entering the range telescope 370 when the apparatus 200 is being used in an imaging mode to record images of the subject 201S, during the period of time when the apparatus 200 and subject 201S are experiencing relative movement or when there is a requirement to capture reference images using the range telescope 370 for calibration purposes. Since the residual energy of protons 201PR exiting the subject 201S is low compared to the primary beam energy (typically below 50 MeV compared to, say, 200 MeV) the second absorber element device 230A2 can be relatively thin compared with the third absorber element device 230A3. This thinner absorber element device 230A2 may for example be formed from brass and have a thickness of around 6 cm although other thicknesses and other materials may be useful in some embodiments.

The third absorber element device 230A3 is arranged to present an absorption cross-section that, in conjunction with the second absorber element device 230A2, is sufficient to stop the full primary beam energy, that is a beam of energy corresponding to the beam 201Bin introduced to the apparatus 200 from the proton source being used. Thus the proton beam 201B may be prevented from entering the range telescope 370 as a safety precaution should the need arise.

It is to be understood that an advantage of providing the second and third absorber element devices 230A2, 230A3 rather than a single absorber element device is that the second absorber element device may be made much lighter than the third. This has the advantage that relatively rapid movement of the second absorber element device 230A2 may be effected more efficiently, enabling faster operation of the apparatus 200 during a lengthy CT scan when proton energy/absorption data is collected at a number of relative orientations of a subject 201S with respect to the apparatus 200.

It is to be understood that movement of the first, second and third absorber element devices 230A1-3 may be achieved through the use of drive modules 230A1D-230A3D respectively. The drive modules 230A1D-230A3D each contain one or more lead-screws driven by one or more electric motors in order to translate the relevant portion of the respective absorber element device 230A1-3. The drive modules 230A1D-230A3D are controlled by primary control device 290.

In the present embodiment, the PSD devices 210A, 210B, 220A, 220B of the first and second beam tracker structures 210, 220 and the CMOS detector devices 372A1-12 of the range telescope 370 together with the associated electronic circuitry are cooled by cooling fans 200CF. Other cooling arrangements may be useful in addition or instead in some embodiments.

In the embodiment of FIG. 19 a beam shaper element 201BS is provided upstream of the first beam tracker structure 210. The beam shaper element 201BS is arranged to absorb energy from the proton beam 201B and is shaped to have a thickness in a direction parallel to a path of travel of the proton beam 201B arranged such that a beam 201B of desired intensity as a function of position over a cross-sectional area thereof, and of desired cross-sectional shape or profile, emerges from the element 201BS and enters the first beam tracker structure 210. In the present embodiment the beam 201B is configured to have a substantially circular cross-sectional profile although other cross-sectional shapes may be useful in some embodiments. The beam shaper element 201BS may be configured to modify the energy spectrum of the proton beam 201B so as to reduce the beam energy by a predetermined amount as a function of position with respect to a cross-sectional area of the beam, in some embodiments. The beam shaper element 201BS may be configured to cause a shape of the beam to corresponding substantially to a projected area of a subject 201S that is to undergo proton absorption, such as a projected area of diseased tissue, where the Bragg peak BP is to be located. Other absorber elements may be provided upstream of the subject 201S in addition or instead in some embodiments.

Operation

The apparatus 200 has three principal modes of operation which will now be described in turn with reference to FIG. 20.

Quality Assurance (QA) Mode

In this mode of operation illustrated in FIG. 20($a$), the first and second beam tracker structures 210, 220 are employed together with the range telescope 370 in order to measure various characteristics of the beam including beam energy, beam flux, total particle dose delivered, and beam profile.

The beam flux may be up to $2 \times 10^7$ protons/cm$^2$/s in some embodiments. In order to prevent the detector devices 210A, 210B, 220A, 220B of the first and second beam tracker structures 210, 220 from saturating, the beam tracker structures 210, 220 may be configured to record a known fraction of the beam flux. This is also the case for the In-Treatment Monitoring (ITM) mode described below.

Figure 21:
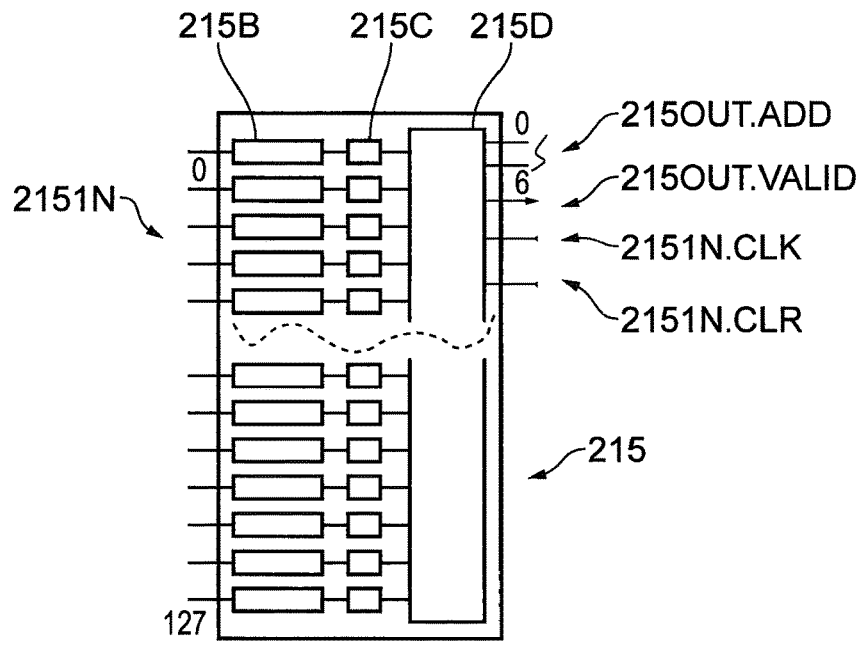
FIG. 21 is a schematic illustration of an architecture of a readout chip for a strip detector device according to an embodiment of the present invention.

FIG. 21 illustrates the architecture of the custom readout circuit 210A1R which, as noted above, is in the form of an application specific integrated circuit (ASIC) chip 215. The chip 215 has 128 input channels 215IN, each connected to an individual strip (such as strip 210A1STR) of the associated strip detector device 210A1-3, 210B1-3, 220A1-3, 220B1-3. In the present embodiment, each solid state strip detector device 210A1-3, 210B1-3, 220A1-3, 220B1-3 has 1000 strip elements and therefore 8 ASIC chips 215 are employed per strip detector device. In some embodiments, a smaller number of chips 215 may be employed by multiplexing.

Each input channel 215IN has an associated analogue processing portion 215B and a register 215C to record if the strip has been "hit". The register 215C provides an output to a logic block 215D that contains a priority encoder. The logic block 215D outputs the address of a strip that has been "hit" to an output 215OUT_ADD. The address data output to the output 215OUT_ADD is valid when a Valid Address output line 215OUT_VALID is high. The inputs to the chip 215 include a Master Clock input 215IN_CLK and a Clear Data input 215IN_CLR. A Master Clock signal is applied to the Master Clock input 215IN_CLK that is a multiple of the pulse period of the generator generating the proton beam 201B, and is synchronised to this pulse period. It is to be understood that in the present embodiment the generator generating the proton beam is configured to generated pulses of protons with a predetermined, substantially fixed pulse period. The readout chip 215 is configured to synchronise readout of data from the first and second beam tracker structures 210, 220 with the generation of pulses by the generator.

Figure 22:
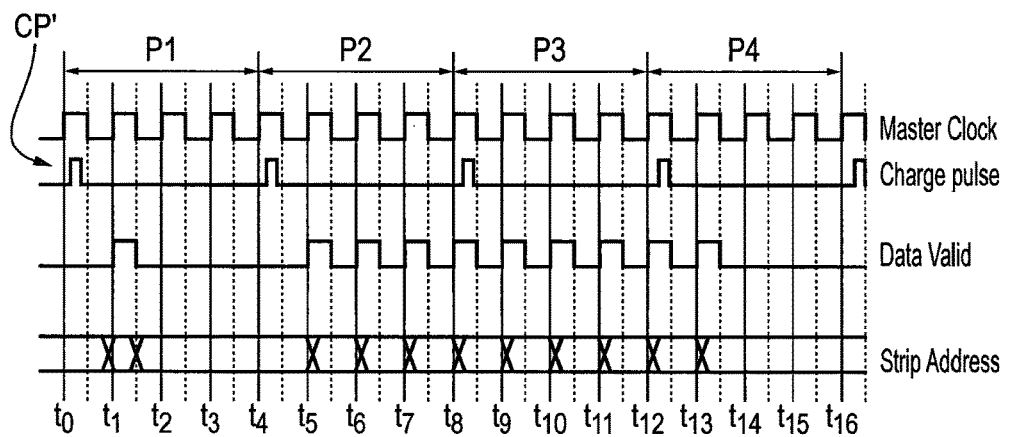
FIG. 22 is a schematic illustration of a timing diagram for a readout chip for a strip detector device according to an embodiment of the present invention.

FIG. 22 is a timing diagram for each chip 215 and illustrates an example of operation of the apparatus 200. It can be seen from FIG. 22 that a charge pulse CP' is generated by one of the strip detector devices 210A1-3, 210B1-3, 220A1-3, 220B1-3 during the first pulse period P1 in response to a single strip element of the strip detector device being "hit". The pulse period P1 runs from time t0 to time t4, with the charge pulse being generated between time t0 and time t1.

The strip address is read out via output 215OUT_ADD when the output 215OUT_VALID is high, during the period between time t1 and time t2

During the second pulse period P2, nine strips are "hit" during the period from time t4 to time t5. In the present embodiment, the Master Clock signal is four times faster than the accelerator repetition frequency and therefore only four valid strip addresses can be read out in a given pulse period P. Three addresses are read out in pulse period P2, with the remaining six strip addresses being read out during the subsequent two pulse periods, period P3 and period P4. Any "hits" occurring in these subsequent two pulse periods are ignored.

It is to be understood that by reading out all hits that take place in a given pulse period P and recording the total number of pulse periods that occur during a given period over which data is acquired, it is possible to form a good estimate of the integrated flux over a given time period even though the number of pulse periods for which data is read out may be unpredictable, and dependent on the particle flux.

The total number of hits during a given time period T, measured in Master Clock cycles, is given by:

Number of hits in time $T$(in Master Clock cycles)= (no of recorded hits*$T$)/(read period,$t$), where t is the number of Master Clock cycles to read all "hit" addresses.

It is to be understood that in an alternative method implemented in another embodiment, the readout chip 215 could be read less frequently, with a period between readout of address data, in response to a charge pulse, that is given by N times the Pulse period P. If N is chosen so that for a given primary beam current, all "hit" strip addresses will be read, then the total number of hits will be N * (no of recorded "hits").

The position at which a proton 201PR passes through a given detector device 210A, 210B, 220A, 220B, the direction of travel and any convergence or divergence of the beam 201B can be observed and/or recorded, using the detector devices 210A, 210B, 220A, 220B by reconstructing a two-dimensional (X-Y) image of proton position for each detector device 210A, 210B, 220A, 220B as described in mode detail below. Alternatively, this information may be observed and/or recorded more rapidly and directly by observing the one-dimensional profiles recorded by each strip detector device 210A1, 210A2, 210A3, 210B1, 210B2, 210B3, 220A1, 220A2, 220A3, 220B1, 220B2, 220B3.

Figure 23:
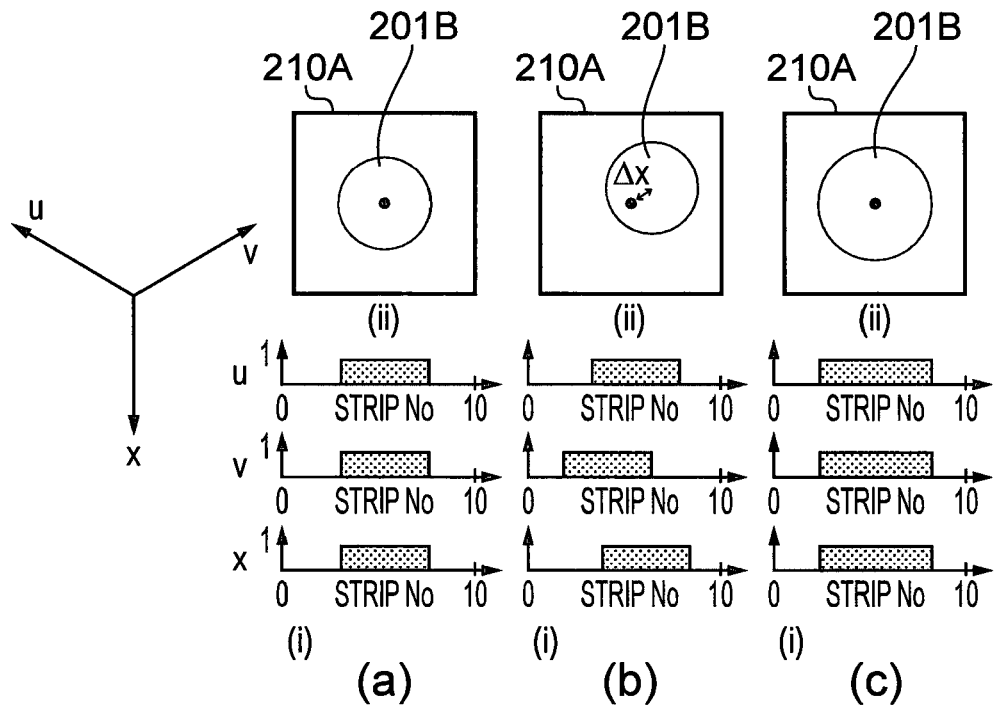
FIG. 23 is a schematic illustration of a beam profile measured by each of three strip detector devices of the PSD device of FIG. 9, the strip detector devices being oriented at substantially 120 degrees with respect to one another.

FIG. 23 (a) (i) shows a plot of strip state (logical 1 or logical 0) as a function of strip number, for each of the three strip detector devices 210A1-3 of the upper proximal detector device 210A. Logical '1' indicates that a strip has registered at least one hit in a given pulse period, whilst logical '0' indicates that a strip has not registered any hits in a given pulse period. The upper plot of FIG. 23(a) (i) corresponds to device 210A2, the middle plot corresponds to device 210A3 and the lower plot corresponds to device 210A1.

The three plots of FIG. 23(a) (i) are indicative of a beam 201B that is substantially centrally located with respect to the active area of the PSD device 210A. The distribution of the beam with respect to the active area as viewed normal to a plane of the detector device 210A, substantially parallel to a direction of travel of the beam 201B, is illustrated schematically in FIG. 23(a) (ii).

FIG. 23(b) shows corresponding data in respect of a beam deflected by a distance Δx in a direction parallel to axis v, i.e. in a direction parallel to the strips 210A3STR of strip detector device 210A3. FIG. 23(c) shows corresponding data in respect of a substantially centred beam exhibiting increased divergence compared with that of FIG. 23(a). Variations in beam size and position can be automatically monitored and used to control the proton source or other components of the apparatus 200.

During the quality assurance procedures, various phantoms (such as articles of known absorption characteristics) and/or calibration equipment (89) may be inserted into the space normally occupied by a patient, as required.

In-Treatment Monitoring (ITM) Mode

The ITM mode is illustrated in FIG. 20(b). The ITM mode allows an operator to obtain in-vivo verification of treatment delivery to a subject 201S such as a patient.

The primary clinical requirements for in-treatment monitoring may be twofold: (i) to provide a record of the radiation that has been delivered to the subject 201S (in comparison to what was planned) in terms of beam profile, position and fluence, and (ii) to provide a real-time warning if the delivered treatment is out of tolerance with that planned, so allowing a cessation of treatment. Thus, if any one of the beam profile, position and fluence differs from that planned by more than a predetermined amount, the apparatus 200 may automatically terminate exposure of the subject 201S to radiation.

For normal treatment, the energy of the protons 201PR is such that substantially no proton radiation exits the subject 201S since the protons 201PR are absorbed by the subject 201S. Accordingly, the only operational elements of the apparatus are the upper and lower proximal detector devices 210A, 210B of the first beam tracker module 210, i.e. the second beam tracker structure 220 and range telescope 370 are not used during actual patient treatment, in which the Bragg peak of particles is arranged to coincide with a region of tissue within the subject 201S that is to be treated, in some embodiments. For safety reasons, the range telescope 370 may be blanked by one or both of the absorber element devices 230A2, 230A3, i.e. one or both of the absorber element devices 230A2, 230A3 may be placed in the beamline in order to prevent protons from entering the range telescope 370. During treatment, an operator may monitor the position and shape of the beam 201B by reference to the outputs of the first beam tracker module 210 described with reference to FIG. 23. The fluence of the beam may also be monitored with reference to the outputs of the first beam tracker module 210 by monitoring the number of hits recorded by the module 210 in a given counting period.

Patient Imaging (PI) Mode

FIG. 20(c) illustrates the PI mode. The aim of this mode is primarily to enable the apparatus 200 to provide 2-dimensional projection images and a full proton CT scan of the subject 201S. This is a mode unlike the previous two modes in that it is desirable for the beam 201B to be as broad as possible and the beam current as low as feasible to record individual protons. This is because it is desirable to balance the ability to track individual protons with a high probability with the time required to acquire a full data set in the interests of the patient. The beam energy is increased to allow protons to exit from the patient with a residual energy in a range up to about 70 MeV.

It is useful to consider an estimate of the number of protons required to produce a reasonable quality CT image. To reconstruct a proton CT image adequate proton detection statistics are ideally required over a range of angles covering a range of angles of up to 180° or up to 360° around the patient. Each pixel in a 2D image or each voxel in a CT image recorded should have sufficient statistical accuracy to achieve the required density discrimination. It is also necessary to match angular sampling with spatial sampling to enable correlation between features in respective 2D images recorded at different angles of the proton beam 201B with respect to the subject 201S. Calculations suggest that some $4 \times 10^5$ protons per voxel are required for a 25 cm diameter object imaged with 200 MeV protons with a voxel size of 1 mm and 1% density discrimination. Such a sized CT image, and with 1% tissue contrast discrimination would be highly beneficial as this is the contrast difference between white and grey brain matter. If imaging at 1° intervals over 180°, this gives $2 \times 10^3$ protons per voxel per angle. For a $2 \times 10^5$ protons/cm$^2$/s proton flux and 1 mm voxel size, this requires a capture time of 1 s. Allowing for physical rotation time, the entire process could take approximately 5 min, which is acceptable to a patient.

Figure 24:
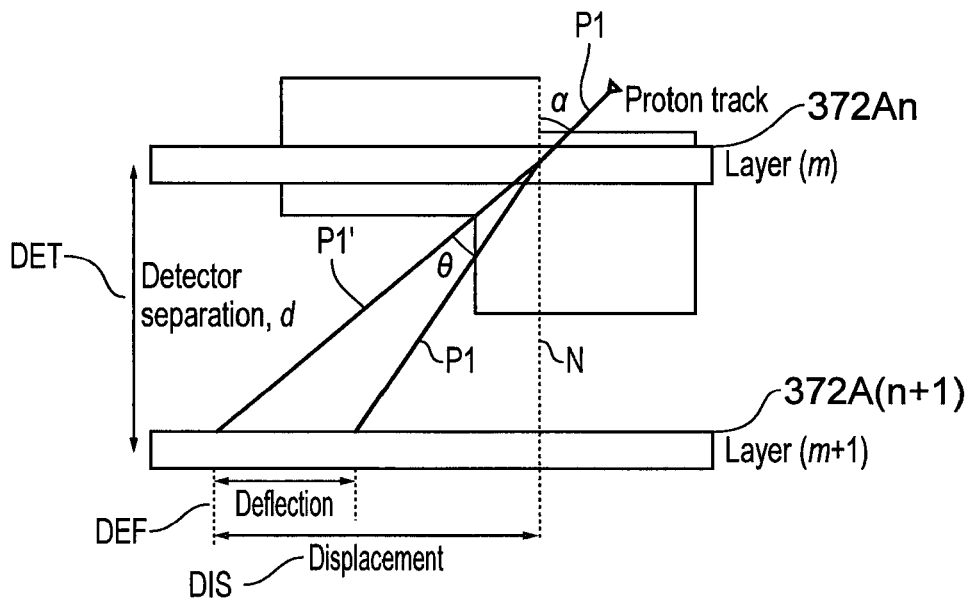
FIG. 24 is a schematic illustration of a beam interacting with a pair of respective strip detector devices of the PSD device of FIG. 9, the figure defining 'deflection' and 'displacement' components of a proton track deviation.

As protons experience multiple scattering, it is desirable that individual protons can be uniquely identified (or, as ensembles of protons are being considered, that a satisfactory majority of them can be so identified) as they pass through the various detectors in the apparatus. As shown in FIG. 24, protons are deflected, by some random angle, θ, at each detector (strip detector device or CMOS detector device) or absorber element so that a change in their previous trajectory occurs. Taking the example of passage of a proton 201PR through the portion of the range telescope 370 shown in FIG. 24, the "deflection" DEF and not the "displacement" DIS of a proton from one CMOS detector device 372An to the next CMOS detector device 372A(n+1) is indicative of the amount by which proton trajectory is modified by CMOS detector device 372An. It can be seen in the example of FIG. 24 that for a detector spacing DET, the actual proton path P1' may be considered to be a path that has been deflected by a deflection angle θ relative to a path P1 straight through detector device 372An. The fact that deflection angle θ is non-zero results in deflection of the location at which the proton passes through the next detector device 372A(n+1) by a distance DEF, resulting in a total displacement of the location at which the proton passes through the next detector device 372A(n+1) by a distance DIS from a location of detector device 372A(n+1) at which a notional line normal to the detector devices 372A through the location of the preceding detector device 372A(n) at which the proton passes through the device 372A(n) passes through said next detector device 372A(n+1).

An extensive Monte Carlo simulation of the apparatus 200 was performed, with the PSD devices 210A, 210B, 220A, 220B of the first and second beam tracker structures 210, 220 and the CMOS detector devices 372A and absorber elements 374A of the range telescope 370 appropriately parameterised. For the purpose of the simulation, a range telescope with 16 absorber elements 374A and corresponding detector devices 372A was employed, i.e. the range telescope 370 with 16 module portions 370M.

Figure 25:
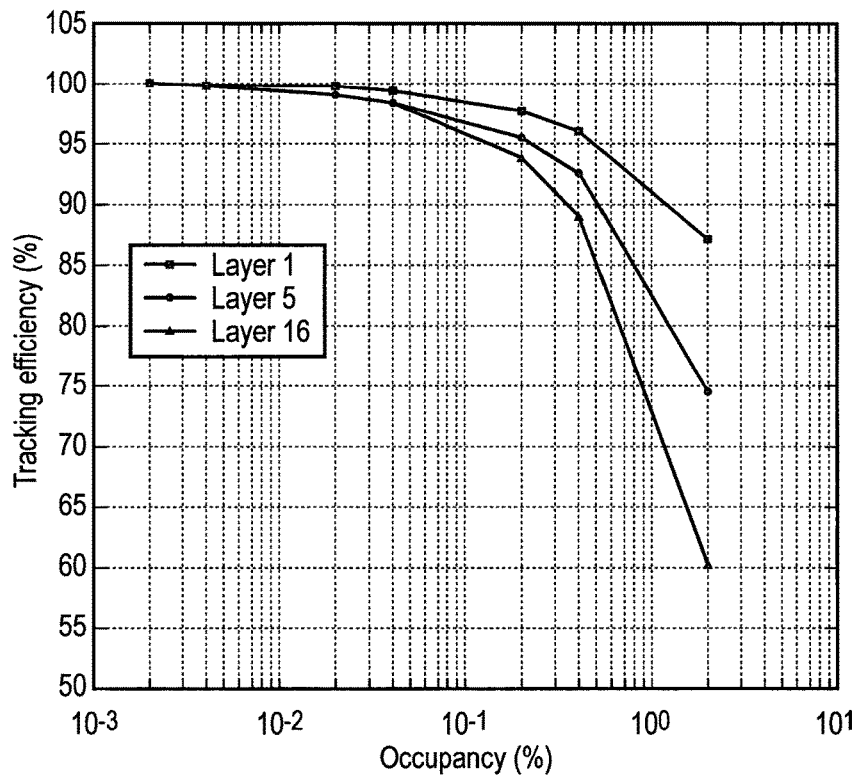
FIG. 25 is a plot of tracking efficiency by the apparatus of protons in terms of fraction of incident protons being detected as a function of occupancy for the $1^{st}$, $5^{th}$ and $16^{th}$ CMOS detector devices of a range telescope similar to that of FIG. 5 and having 16 CMOS detector devices.

From the simulation, the efficiency of tracking individual protons as a function of imager occupancy (that is the fraction of pixels that detect a proton) for the $1^{st}$, $5^{th}$ and $16^{th}$ (last) absorber element/detector device layers in the range telescope 370 was determined and the data obtained is plotted in FIG. 25. For up to 10 protons 201PR simultaneously present in the range telescope 370, the efficiency (in terms of fraction of incident protons being detected) of the first layer is 99.9%, and the efficiency of the last layer is 99.8%. For 1,000 simultaneous protons, the efficiency falls to 96.0% and 89.1% respectively; for 5,000 protons the efficiency falls further to 87.0% and 60.1% respectively. Due to multiple scattering of the protons 201PR (and a fraction may even be deflected out of the active region of the detectors), only a relatively low number of protons 201PR can be present in the apparatus 200 at a given moment in time if their tracks are to be reliably recorded. This implies relatively sparse data and therefore data compression may be employed in order to optimise data transfer, processing and storage.

Figure 26:
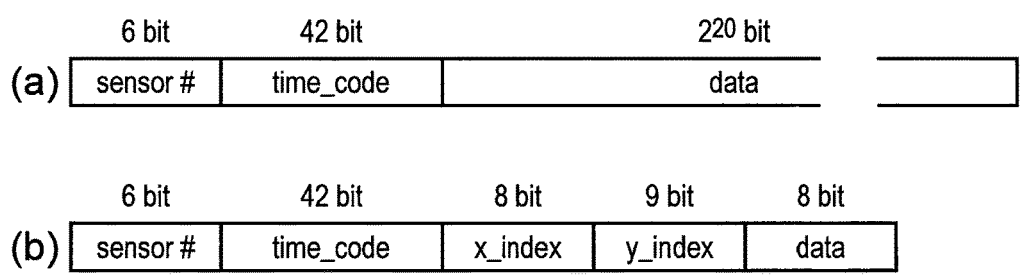
FIG. 26 illustrates data structures for uncompressed and compressed CMOS detector device output data.

With about 250,000 pixels in each CMOS imaging device 372A of the range telescope 370, only about 0.4% pixels are occupied with valid proton interaction events when a pulse of protons 201PR enters the telescope. Storing the full imager frames would yield 32 Mbits of raw data in one frame readout time—several thousand frames per second. FIG. 26 illustrates the different possible data structures for (a) uncompressed and (b) compressed data readout from a given CMOS detector device. Both structures contain an identification field (sensor #) to identify the individual detector device 372A in the telescope 370 with which the data is associated and a 42-bit counter (time_code). The counter time_code is a counter with respect to the master clock of the apparatus 200 and identifies the time at which readout of each detector device 372A occurs. The data field (data) records, for each pixel of the detector device 372A, whether a proton 201PR has been detected by that pixel, i.e. whether the pixel has experienced a 'hit'. For a master clock frequency of 100 MHz, a 42-bit time_code permits a total unique measurement time of up to about 12 hours.

In contrast to the uncompressed data format of FIG. 26(a), in the compressed data format illustrated in FIG. 26 (b) only the coordinates of those pixels "hit" are recorded. The coordinates of each hit are given in terms of x coordinate (x_index) and y coordinate (y_index) for each pixel that has experienced a "hit". For the compressed format, 8K bytes will encode nearly 900 events. In uncompressed format, around 131,078 bytes would be required to encode a similar number of events (that is a ~16:1 compression).

It is to be understood that since there are relatively few protons to capture in a frame and frame speeds are relatively high, it is advantageous if all detector devices of the apparatus 200, i.e. each of the PSD devices of the first and second beam tracker structures 210, 220 and the CMOS detector devices of the range telescope 370, capture data for all, or at least the majority, of the time.

Figure 27:
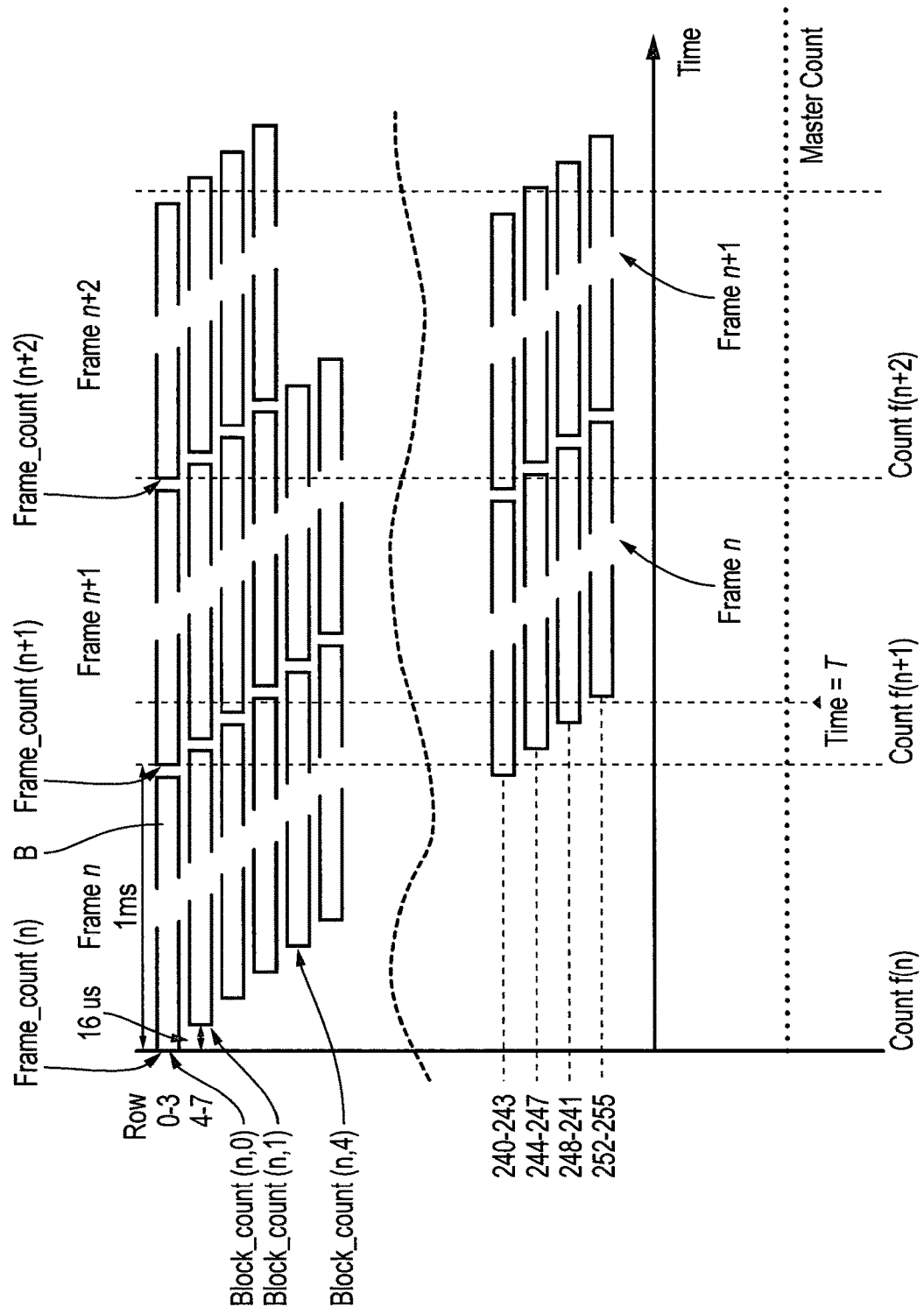
FIG. 27 is a schematic illustration of the data output structure as a function of time for a CMOS detector device employed in the range telescope of FIG. 5.

The CMOS detector devices 372A of the range telescope 370 (and range telescope 270) are operated in "rolling shutter" mode as illustrated in FIG. 27, as opposed to "snapshot" mode (or "global shutter" mode). This enables the devices 372A to collect data substantially continuously. In the present embodiment, as illustrated in FIG. 27, data from each detector device 372A of the range telescope 370 is read out in blocks of four rows at a time. In FIG. 27, the integration periods over which the pixel elements of a given block of four rows collect charge before being read out are indicated by a bar B. The period between bars representing a given block row corresponds to a period of approximately 16 microseconds, being the period required to read out the charge accumulated by each pixel element of each row of the block B. The integration period of each block is substantially 1 ms in the embodiment illustrated.

The number of rows that may be read out simultaneously is set by the number of outputs and the speed of the analogue-to-digital conversion.

Figure 28:
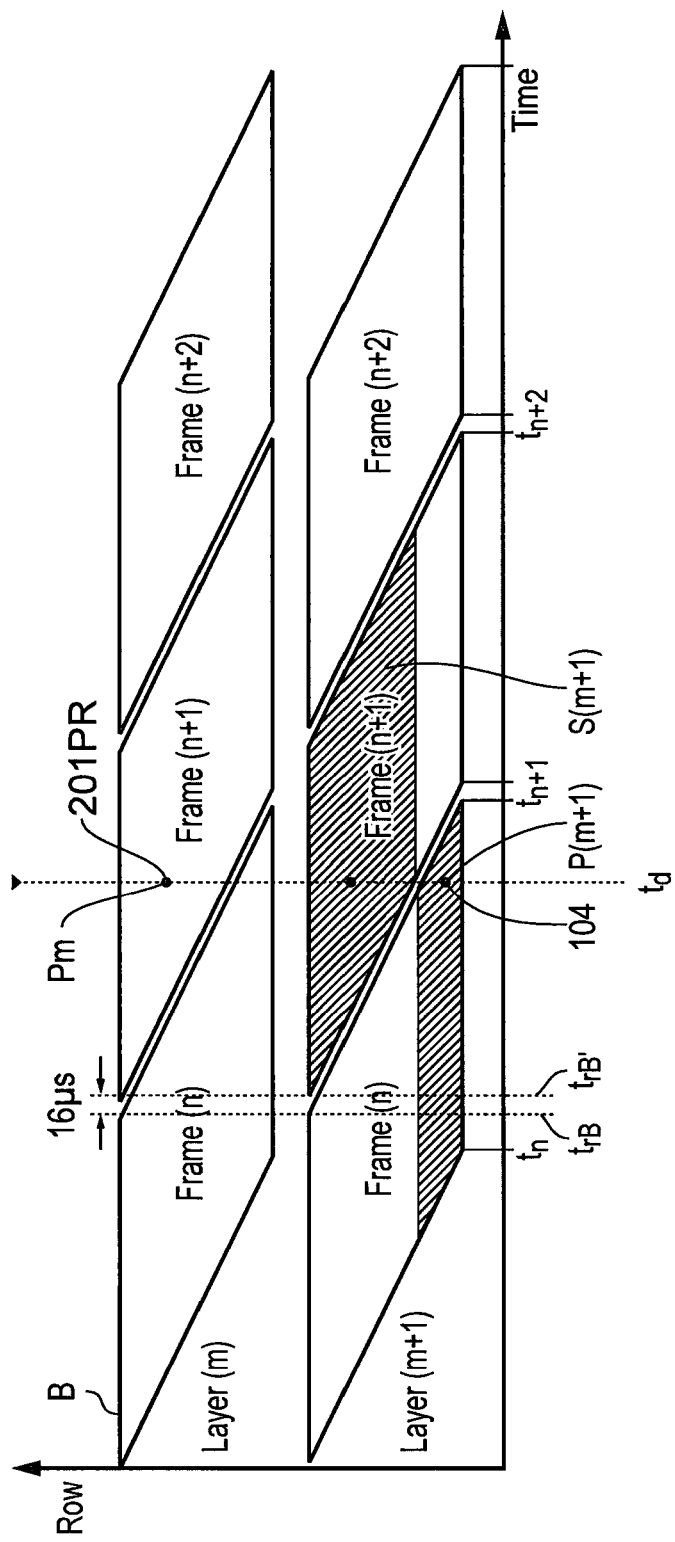
FIG. 28 is a schematic illustration of the search space across respective CMOS detector devices of the range telescope of FIG. 5 in the case of a single proton event.

If a proton 201PR passes through a given CMOS detector device 372A (or imager) at time T (FIG. 27) then it may be detected in any of the blocks B whose integration period includes time T. It is to be understood that the proton 201PR may be scattered in any direction by a given CMOS detector device 372A and a proton 201PR scattered by one detector device 372A may in principle be detected by any pixel of the device 372A of the next layer. If two consecutive layers of CMOS detector devices 372A are considered, i.e. two consecutive devices 372A, as illustrated in FIG. 28, then a proton 201PR may be detected at a given position Pm indicated in layer m at time, $t_d$, and also detected in the next layer (m+1) at location P(m+1) at time $t_d$. The blocks B of layer (m+1) that are responsive to the presence of the proton 201PR during the time $t_d$ are indicated by the shaded region S(m+1) of FIG. 28. That is, the proton 201PR could be detected in any of the blocks B of this shaded region S(m+1) of layer (m+1).

Figure 29:
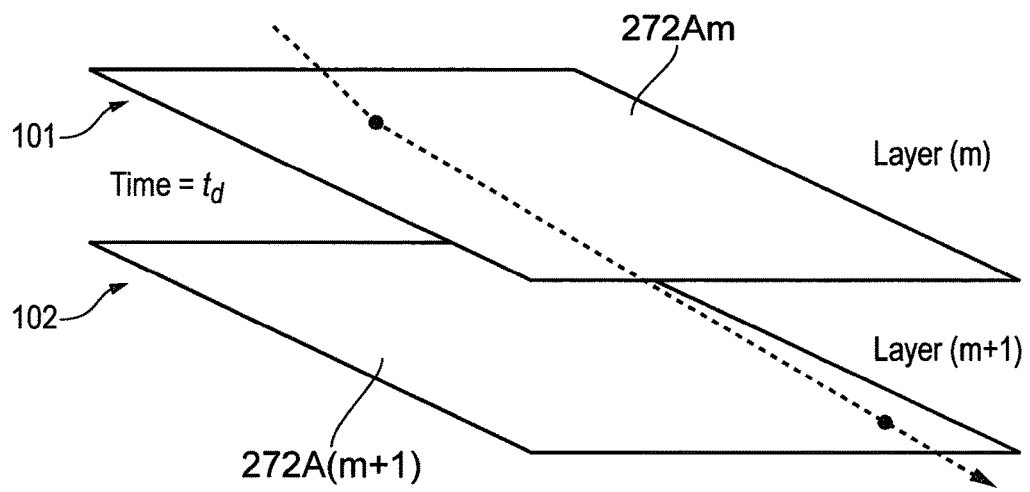
FIG. 29 is a schematic illustration of a proton trajectory between respective adjacent CMOS detector devices of the range telescope of FIG. 5.

FIG. 29 shows an example of a likely trajectory of proton 210PR at time $t_d$.

It is to be understood that CMOS-based photodiode imaging devices exhibit fixed pattern noise, due at least in part to differences in the gains and thresholds such as turn-on potential thresholds of the individual transistors at the pixel or column level, and temporal noise and drift due to leakage and temperature effects. It is desirable to minimise noise due to these effects, especially since the electrical signal generated in a CMOS detector device resulting from the passage of a high-energy proton through the device can be relatively small.

Offset Subtraction

Fixed pattern noise can be eliminated or at least reduced by subtracting from a given image acquired in the presence of a flux of protons, frame obtained from an image data taken under 'dark' conditions, i.e. in the absence of a flux of protons, in a pixel-wise manner.

In the present embodiment, a series of dark frames are recorded prior to a run and an average value of signal generated by each pixel of each detector device 372An over the series of dark frames is determined and stored as reference image data. Since the period of time over which it may be required to collect data in respect of a subject 201S may be relatively long, acquisition of dark frames in order to update the stored reference image data in respect of CMOS detector device condition may be performed regularly with relatively high frequency. It is to be understood that, during acquisition of image data in the presence of a flux of protons, the reference image data may be subtracted from image data captured by the apparatus in order to obtain an 'offset-subtracted' or 'corrected' image.

Thresholding

As noted above, the electrical signal generated in a detector device 372An resulting from the passage of a high-energy proton therethrough or absorption thereby can be relatively small and must be distinguished from the overall background readout and thermal noise of the CMOS detector device 372An. By recording the variance of the signal s, pixel-wise, obtained after acquisition of each dark field image, it is possible to estimate the noise. By setting a threshold signal value that is a predetermined multiple of this noise signal, on a pixel by pixel basis, and only accepting signal values above this threshold as proton events in respect of a given pixel, a beneficial increase in detector device performance may be obtained. That is, the number of events recorded by a detector device 372An that did not in fact correspond to passage of a proton through the detector device 372An or to absorption of a proton by the detector device, may be reduced. The multiplier may be in the range from around 2 to around 6 in some embodiments, such as substantially 2, 3, 4, 5 or 6. In the present embodiment the number is 4.

Defect Masking

It is advantageous also to take into account the presence of any defects in a detector device 372An, such as one or more 'bright' pixels, faulty columns readout defects, and so forth. A bright pixel is a pixel of a CMOS detector device 372An that outputs consistently a high signal when read out, indicating that a 'hit' has been recorded by that pixel, even in the absence of a hit. Similarly, a fault in a column of pixels may result in each pixel of that column indicating a hit has taken place when in fact no hit has taken place, or the column may be unresponsive to any hits. It is to be understood that bright pixels and column faults need to be considered as they may give rise to incorrect data in respect of the locations and number of 'hits' occurring. Since data corresponding to the occurrence of a proton 'hit' is expected to be sparse and data compression is employed before transferring the data to mass storage and further processing, it is advantageous if the masking of faulty pixels is performed at the time of image acquisition. With only a small number of events per frame (typically a few 100), a faulty column (that is always bright) could generate over 500 additional pixel values to be stored. Therefore, in the present embodiment, a pixel-wise mask is created as part of a process of system calibration, and used to ignore affected pixels. That is, data is not recorded in respect of affected pixels in subsequent data acquisition processes.

Figure 30:
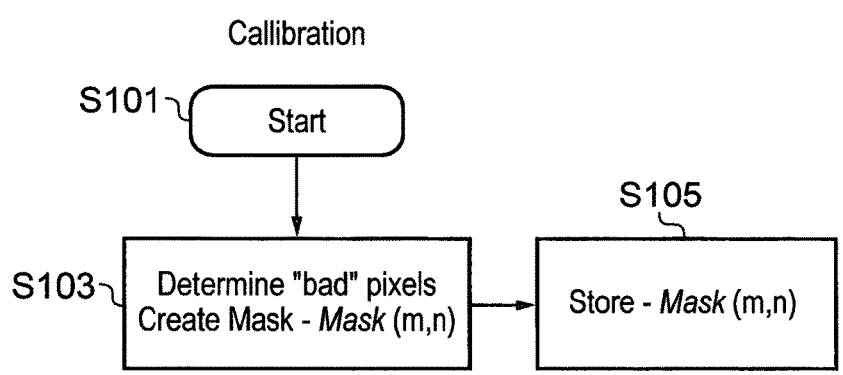
FIG. 30 is a flow diagram of a method of establishing a mask or masking function for image generation in apparatus according to an embodiment of the present invention.

FIG. 30 illustrates a method of establishing a pixel-wise mask according to an embodiment of the present invention. At step S101 the method commences. At step S103 the range data processing system 270DP of the range telescope 370 determines which pixels of a given detector device 372An of the telescope 372 are faulty and creates a mask or dataset recording the (x,y) position of each pixel 372AP with respect to the pixel array of each detector device 372An. At step S105 the mask is stored in a memory of the range data processing system 370DP. It is to be understood that the mask may in addition or instead be stored in a memory of the primary control device 290.

Figure 31:
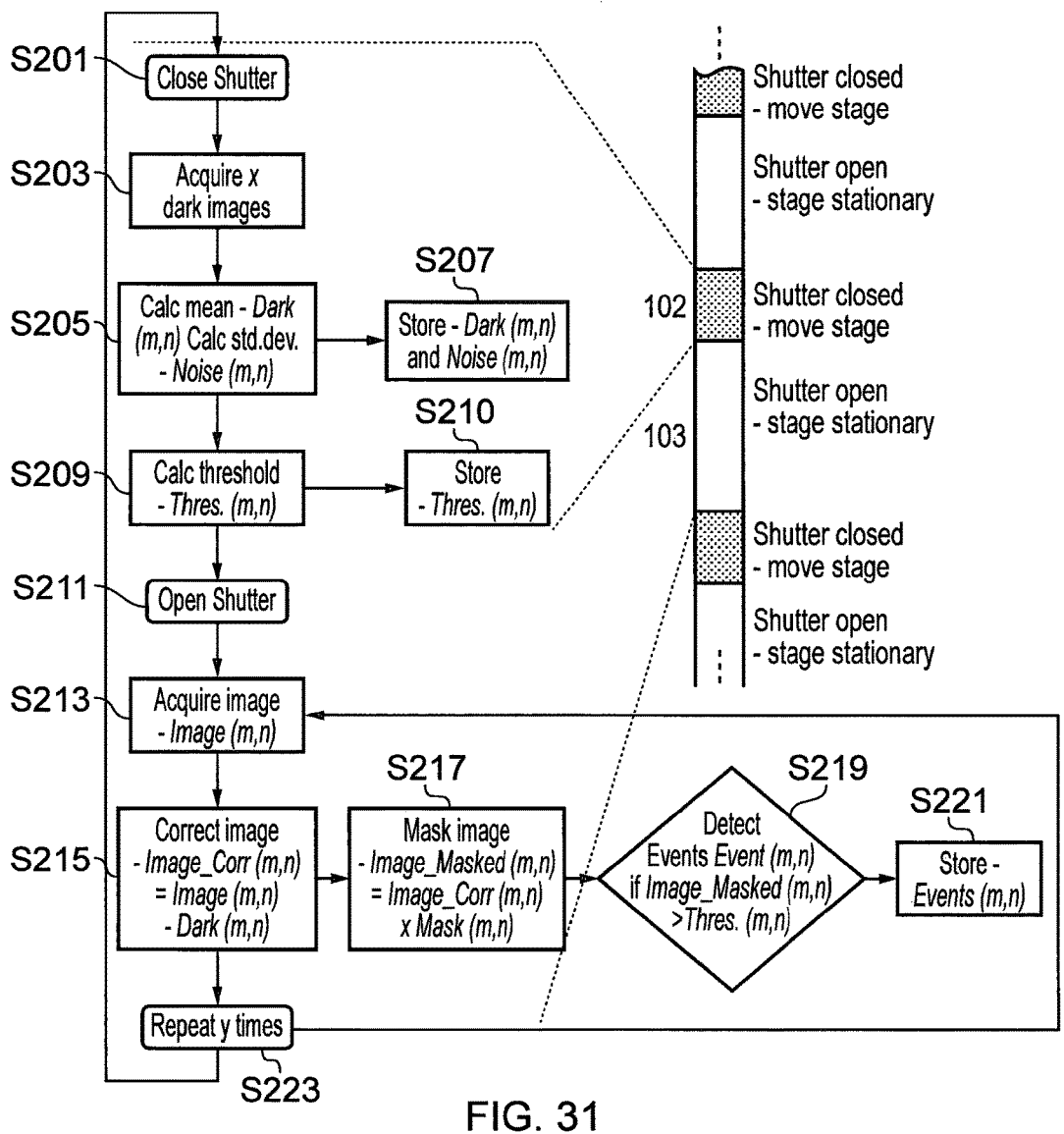
FIG. 31 is a flowchart of operations performed by CT scanner apparatus according to an embodiment of the present invention during a given period of readout of data from the CMOS detector devices of the range telescope of the apparatus of FIG. 4 when operated in a Patient Imaging (PI) mode, including the steps of correcting data for fixed pattern noise, establishing a masking function by the method illustrated in FIG. 30, and performing signal thresholding.

FIG. 31 is a flowchart of operations performed by the CT scanner apparatus 200 during a given 'run', or period of image acquisition, when the apparatus 200 is operated in the Patient Imaging (PI) mode.

At step S201 the primary control device 290 causes the second and third absorber element devices 230A2, 230A3 located upstream of the entrance 370E to the range telescope 370 to be placed in the closed position so as to substantially block protons 201PR from entering the range telescope 370.

At step S203 a predetermined number of dark field images are recorded by the range data processing system 370DP of the range telescope 370 by recording data output by the CMOS detector devices 372A of the range telescope 370 as described above. The data is in the form of image data values indicative of the amount of radiation detected by a given pixel 372AP of each CMOS detector device 372A.

At step S205 the mean value over time of the image data values for respective pixels of respective images is calculated in a pixel-wise manner in order to obtain a reference dark field image Dark(m.n) for each detector device 372An of the range telescope 370. A standard deviation of the dark field image data in a pixel-wise manner over the dark field images that were captured is calculated as Noise(m,n) in order to provide an estimate of the noise level associated with image capture.

At step S207 the data sets Dark(m,n) and Noise(m,n) are stored in a memory of the primary control apparatus 290.

At step S209 a threshold value dataset Thresh(m,n) is calculated for each pixel by the primary control device 290 based on the noise level estimate Noise(m,n). In the present embodiment the threshold value dataset Thresh(m,n) is calculated for each pixel by multiplying the value of each data element of the data set Noise(m,n) by a factor of four although other values of factor, particularly in the range 2-6, may be useful in some embodiments as noted above. At step S210 the dataset Thresh(m,n) is stored in a memory of the range data processing system 270DP.

At step S211 the second and third absorber element devices 230A2, 230A3 are placed in the open position so as to allow protons 201PR to enter the range telescope 270.

At step S213 the range data processing system 370DP of the range telescope 370 records data output by the CMOS detector devices 372A in order to capture a 'bright field' image Image(m,n) of a subject 201A located between the first and second beam tracker structures 210, 220.

At step S215 the range data processing system 370DP subtracts dark field image data Dark(m,n) from the image data image(m,n) in order to obtain a corrected image dataset Image_Corr(m,n).

At step S217 the range data processing system 370DP applies a mask dataset Mask(m,n) to the corrected image dataset Image_Corr(m,n) in order to set to a predetermined value any elements of the dataset that correspond to bright pixels or pixels of a damaged column that provide a permanent 'bright' output. In the present embodiment, application of the mask dataset Mask(m,n) results in any such pixel elements being set to a value of substantially zero although other arrangements are also useful provided the apparatus 200 does not recognise such elements as indicative of a proton 'hit'.

At step S219 the range data processing system 370DP detects whether any of the pixel elements 372AP of a given CMOS detector device 372A have a data value corresponding to a proton 'hit'. This is performed by determining whether the value of any element of the corrected image dataset Image_Corr(m,n) exceeds the corresponding value of the threshold value dataset Thresh(m,n). A dataset Event (m,n) is generated containing data indicative of whether the value of a given element of the dataset Image_Corr(m,n) exceeds the corresponding value of the dataset Thresh(m,n). Any such data elements are stored as having a value logical '1' in the dataset Event(m,n).

At step S223 the apparatus 200 causes the range data processing system 370DP to repeat steps S213 to S221 until the steps have been repeated a predetermined number of times. The predetermined number of times may have any suitable value, for example a value in the range from 5 to 100, from 5 to 1000, or any other suitable number.

Once steps S213 to S221 have been repeated a predetermined number of times, the apparatus 200 continues at step S201.

It is to be understood that during the period for which the collection of the dark field images is performed, and associated data processing to establish datasets Noise(m,n) and Thresh(m,n) is performed, the primary control device 290 may cause the subject 201S to be rotated with respect to the first and second beam tracker structures 210, 220 and range telescope 370 (or vice versa) prior to acquiring new bright field images with the subject 201S in the new orientation. That is, during the period in which the subject 201S (or apparatus 200) is moved to the next CT projection angle, dark field image acquisition and processing may be performed. This feature has the advantage that the effects of changes in fixed-pattern and temporal noise over the time period during which bright field images are captured can be mitigated without unduly increasing the time for which a subject 201S must be present, enabling a CT scan to be performed within an acceptable period of time.

It is to be understood therefore that capture of dark field images may be repeated on a regular basis during the course of a given run. As described above, this may be advantageously performed during the period of time between capturing a given image or set of images of a subject 201S when the subject 201S (or apparatus 200) is moved to the next CT projection angle. The range telescope 370 is shielded by the absorber element devices 230A2, 230A3 during this movement phase. In some embodiments the subject 201S is also not exposed to radiation during the movement phase, for example by introducing a beam-blocking absorber element in the beamline upstream of the subject 201S.

It is to be understood that, during operation of the apparatus in the patient imaging (PI) mode, there will typically be at most about 1,000 protons traversing the apparatus 200 within the integration time of the CMOS detector devices 372An used in the range telescope 370. This integration time may be of the order of 1 ms.

In contrast, the 'read' or 'dwell' period of the strip detector devices 210A1-3, 210B1-3, 220A1-3, 220B1-3 of the first and second beam tracker structures 210, 220 will typically be much shorter than this—perhaps, 3 to 4 orders of magnitude shorter, and in some embodiments of the order of 10 s of ns, for example around 40 ns in some embodiments. Accordingly, the probability of a proton being detected in one strip detector device read time will be less than unity.

Figure 32:
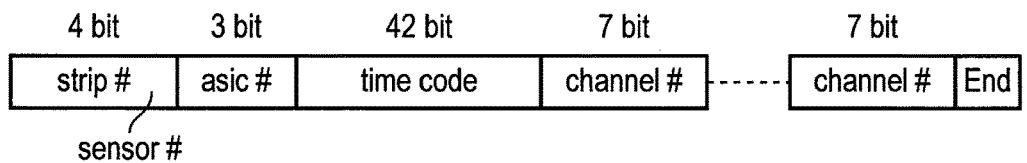
FIG. 32 is a schematic illustration of a compressed data structure being the structure in which data is output by a data processing unit associated with the range telescope of the apparatus of FIG. 4 when the apparatus is operated in the PI mode.

It is to be understood that only the time-stamped addresses of those strip elements (e.g. strip element 210A1STR) being "hit" are recorded, hence greatly reducing data transfer and storage requirements. FIG. 32 illustrates a possible data structure record for storing data output by the PSD devices of the first and second beam tracker structures 210, 220. Data field "sensor #" identifies an individual strip detector device 210A1-3, 210B1-3, 220A1-3, 220B1-3, field "asic #" identifies an individual readout chip 215 for this detector device 210A1-3, 210B1-3, 220A1-3, 220B1-3, field 'time code' is the time at which readout takes place as measured in master clock cycles, field "channel #" identifies the number of the individual strip (such as strip 210A1STR) that recorded a valid hit (there may be more than one event during a single pulse period) and field "End" is a record delimiter.

Other arrangements may also be useful in some embodiments.

Image Processing

Initial processing of the acquired data may include the following stages, in order to facilitate further processing and image reconstruction:

From the range telescope frames or blocks B with their identified events, create lists of valid events.

Figure 33:
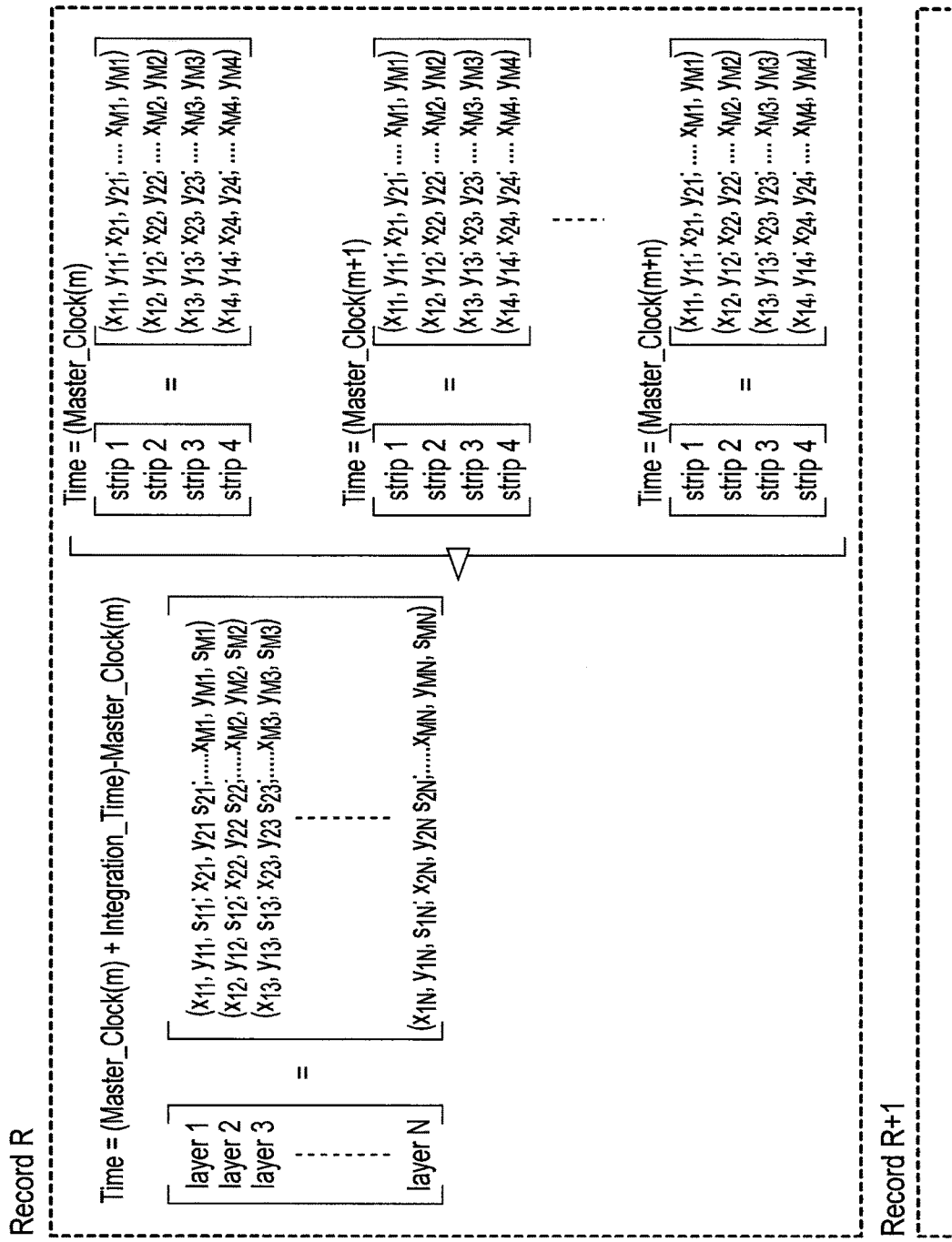
FIG. 33 is a schematic illustration showing data structures for detected paths of particles through the layers of PSD devices and CMOS detector devices of the range telescope of apparatus according to an embodiment of the present invention.

Strip-detector events are split into lists corresponding to the integration period of the range telescope frames or blocks B. A typical data structure is shown in FIG. 33. For each integration time period of the CMOS detector devices 372A1-372AN (i.e. layers 1 to N of CMOS detector devices 372A where N is the number of layers, in the present case 12), the co-ordinates (x, y) of each event detected by the strip detector devices of the first and second beam tracker structures 210, 220 are recorded. As the effective read time of the strip detectors is much shorter than the integration time of the CMOS detectors, there are many such lists recorded within a single integration period of a given CMOS detector device and therefore the numbers of events recorded by the PSD devices 210A, 210B, 220A, 220B may be much greater than that of the CMOS detector devices 371A1-371AN. It is to be understood that in the present embodiment, N=12 as shown in FIG. 15.

As can be seen in FIG. 33, during each integration period (of length Integration_time), for each Master Clock cycle Master_Clock(m), the coordinates of each "hit" or "event" detected by the CMOS detector devices 372A1 to 372AN of the range telescope (i.e. layers 1 to N of CMOS detector devices of the range telescope 370, denoted layer 1 to layer N) are stored. In the present embodiment, the value of a signal, s, corresponding to the amount of charge generated in a pixel element 372AP, is also stored in respect of pixel elements experiencing an event. A list of records for each integration period Integration_time of the CMOS detector devices 372A1 to 372AN, comprising the data in respect of the CMOS detector devices 372A1 to 372AN and the corresponding data in respect of the PSD devices 210A, 210B, 220A, 220B (denoted Strip 1, Strip 2, Strip 3, Strip 4 respectively) is also stored.

Thus, for a given CMOS detector device 372An, and the first proton trajectory determined, the apparatus stores a value $(x_{1n}, y_{1n}, s_{1n})$, where $(x_{1n}, y_{1n})$ are the (x, y) coordinates of the pixel of the nth CMOS detector device 272An that detected a "hit" and $s_{1n}$ is the data value indicative of the amount of charge generated in that pixel 272AP during a given integration period.

It is to be understood that in the case of the PSD devices 210A, 210B, 220A, 220B data is not stored in the dataset of FIG. 33 relating to the magnitude of the signal generated in a given strip element 210A1STR of each strip detector device. Rather, only the coordinate of each event detected by a given PSD device 210A, 210B, 220A, 220B. It is to be understood that the coordinates of all events occurring in the PSD devices 210A, 210B, 220A, 220B over a given integration period are stored, the readout period of each PSD device 210A, 210B, 220A, 220B being much shorter than the integration period Integration_time in respect of the CMOS detector devices 372A1 to 372AN.

The stored lists of events detected by the PSD devices 210A, 210B, 220A, 220B and CMOS detector devices 372A1 to 372AN of the range telescope 370, as illustrated in FIG. 33, are then correlated in order to generate proton trajectories. Thus, the (x, y) coordinates of the locations of each PSD device 210A, 210B, 220A, 220B and CMOS detector device 372A1 to 372AN at which a proton passed through the respective devices are correlated in order to determine the path of each detected proton through the apparatus 200.

Figure 36:
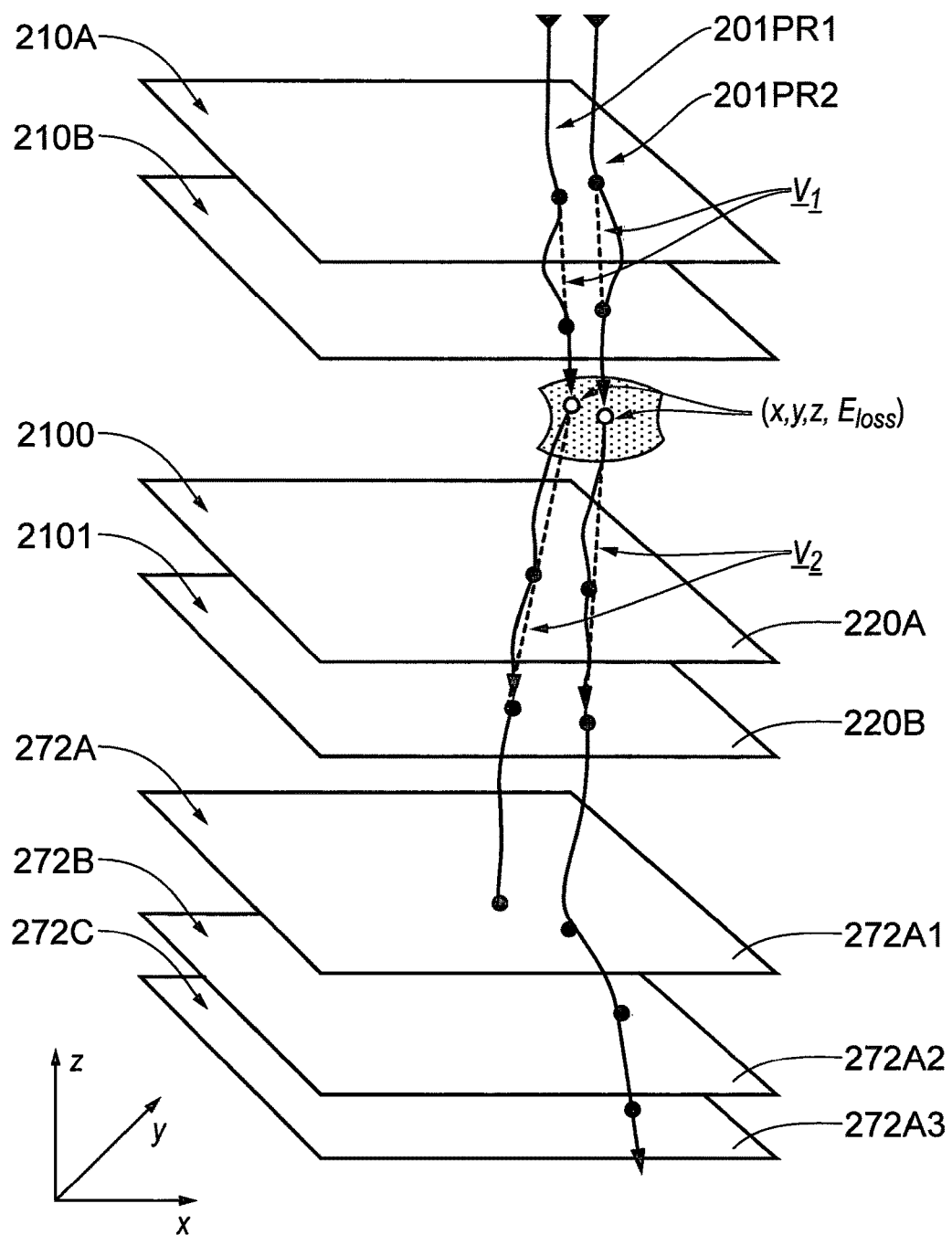
FIG. 36 shows the actual trajectories (solid line) and estimated trajectories as determined by apparatus according to an embodiment of the present invention (dotted line) of two protons, showing the estimated input and output vectors v1, v2 respectively of the protons, the coordinates of the locations of the scanned object at which the protons are scattered by the scanned object and the energy loss in the scanned object.

Events that cannot unambiguously be identified with a unique trajectory are discarded in the present embodiment. In the present embodiment, importantly, for each identified proton, the apparatus 200 calculates input vector v1 (which may also be referred to as $V_{in}$), and output vector v2 (which may also be referred to as $V_{out}$), as shown in FIG. 36 with respect to protons 201PR1 and 201PR2 respectively, together with its residual energy. Residual energy is calculated by tracing the trajectory through the range telescope 370 as described herein.

Figure 34:
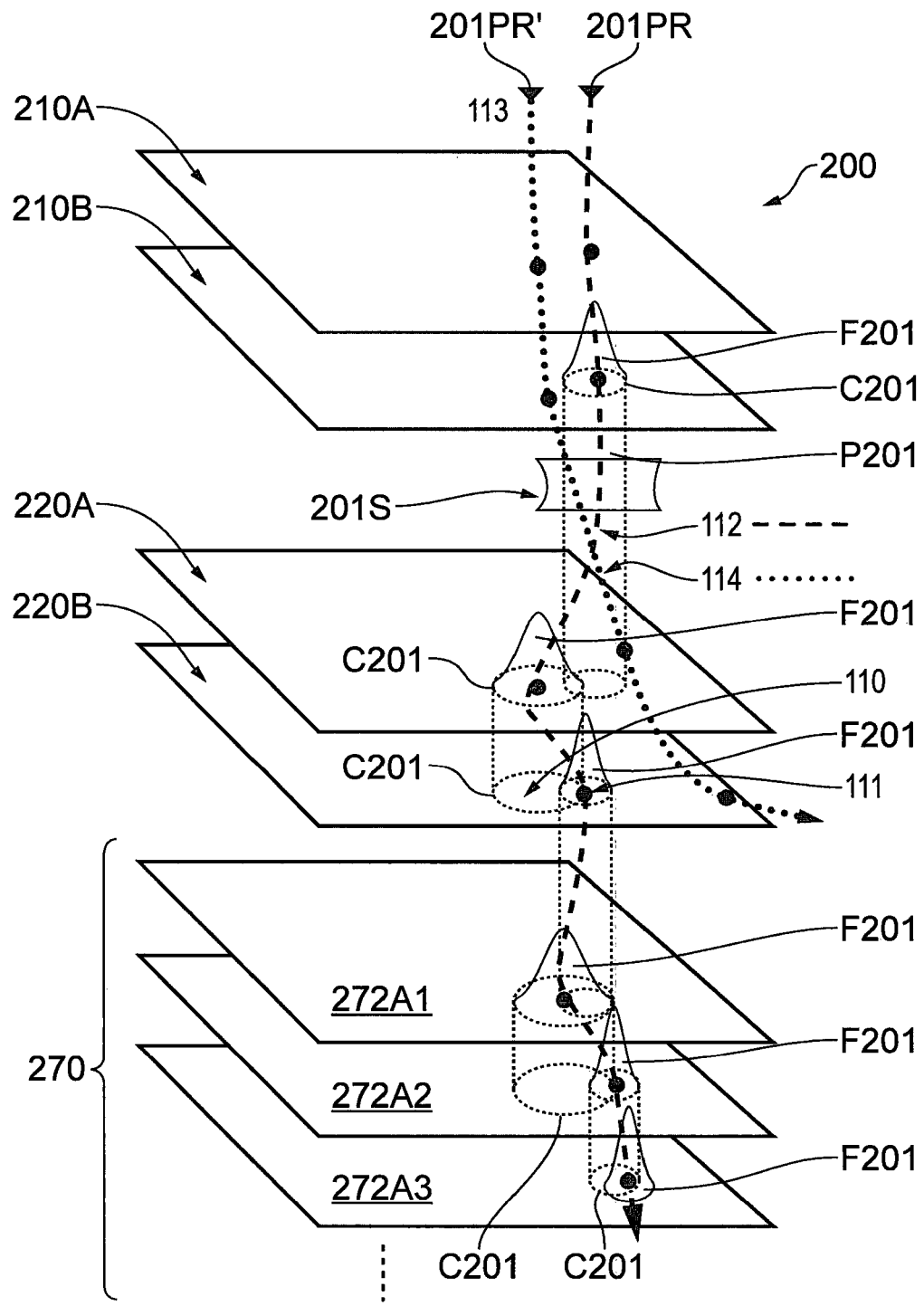
FIG. 34 is a schematic illustration of proton scattering between detector layers including scattering by a subject such as a human patient.

Since protons 201PR undergo multiple scattering, as well as losing energy, as they pass through the 'layers' of strip detector devices of the PSD devices 210A, 210B, 220A, 220B, the subject 201S, the CMOS detector devices 372A1-372A11 and the absorber portions 374A0-374A11, their paths may be as illustrated schematically in FIG. 34. An incident proton 201PR will experience random scattering in each layer. The region in which a given proton 201PR may be expected to interact with the next layer is defined by the dotted circles C201 superimposed on that layer. The probability that the proton 201PR passes through a given point within that circle C201 is given by the probability function F201, a peak in the probability function indicating the most probable point through which the proton 201PR will pass.

Optionally and advantageously, an algorithm to determine the most probable path P201 may take into account not only direct correlation of spatial locations between layers at which protons 201PR are detected, for example where a proton is detected in successive layers at substantially the same location indicative of a relatively small amount of scattering by a given layer, but also situations where a relatively large deflection takes place due to scattering. Several algorithms are available that could be applied in this situation. Such methods are used in the field of Computer Vision for tracking cells, people or vehicles. Examples of multipoint optimisation include Active Contours and Min-Max Graphs.

Some protons 201PR may, for various reasons, not present complete paths. For example, they may be scattered out of the active area or region of detection of a subsequent PSD device 210B, 220A, 220B or CMOS detector device 372A1-N. This is illustrated for the incident proton 201PR' in FIG. 34, which fails to enter the range telescope 370 after being scattered by the lower distal PSD device 220B.

In order more accurately to determine an energy of a proton 201PR, a range telescope according to the embodiment of FIG. 15 in which the outputs of the detector devices 372A1-12 are digitised may advantageously be employed. For optimum performance, the proton 201PR should come to rest before its full traverse of the CMOS detector devices 372A1-N of the range telescope 270. The coming to rest of a proton 201PR may be determined by inspecting the magnitude of the signal, s, corresponding to the amount of charge generated in a pixel element as discussed above, for each layer 1-N of CMOS detector devices 372A1-N at which the proton 201PR is detected. The position of the Bragg Peak, and hence the residual energy of the proton 201PR after passing through the subject 201S, can be inferred by determining the expected position of a peak in signal s as a function of distance along a length of the range telescope 370 from the recorded data. The plot above the illustration of the range detector device 370 of FIG. 15 is of the output signal s of the pixel element of each CMOS detector device 372A1-N with which a given proton interacts as a function of distance along the range telescope 370. It is to be understood that the magnitude of signal s corresponds to the amount of energy E absorbed by a given pixel element 372AP with which a proton interacts. It is to be understood that a curve may be fitted to the data points shown in the plot of FIG. 15 and the expected position of a notional peak in signal s determined. The residual energy of the proton may be calculated from a knowledge of the absorption characteristics and relative thicknesses of the materials in the range telescope 370 through which the proton travels. The further the proton travels, the more material the proton passes through, and therefore the greater the residual energy of the proton.

The presence in a subject 201S of many different tissue types, each with its own density and chemical composition, constitutes a challenge in simulating proton trajectory since an exhaustive simulation would need to simulate the proton passing through each of the tissue types. To overcome this problem, in the present embodiments use is made of an "equivalent path length" of a proton through a given material or combination of materials. The equivalent path length is the distance that a proton of a given energy would travel in water in order to lose the same amount of energy as it loses passing through a given portion of a subject 201S. The reference material may be any suitable substance or material such as water, a particular polymer, or any other suitable material. A water equivalent path length (WEPL) is often employed in radiotherapy calculations. By measuring the residual range of protons 201PR after interaction with the subject 201S, the WEPL distribution across the subject 201S can be inferred.

Figure 35:
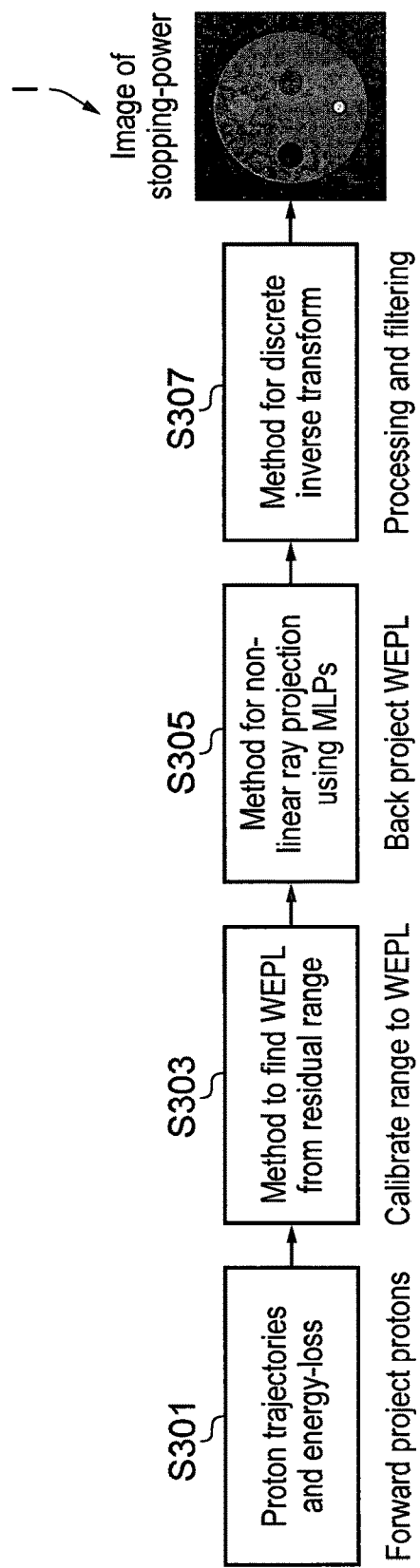
FIG. 35 is a flow diagram illustrating processing stages associated with image reconstruction from the data structure of FIG. 33.

The processing stages for the reconstruction of a 2-dimensional image are shown in FIG. 35.

At step S301 the trajectories of the protons 201PR detected by the range telescope 370 on the distal side of the subject 201S are calculated using the information in respect of path of travel of those protons 201PR provided by the first and second beam tracker structures 210, 220. As described above with respect to the known first and second beam tracker structures 110, 120 shown in FIG. 3, the first and second beam tracker structures 210, 220 of the embodiment of FIG. 4 enable calculation of vectors v1 and v2 (also referred to as $V_{in}$ and $V_{out}$), respectively, being the directions of travel of a proton 201PR through the first and second beam tracker structures 210, 220 respectively. This step may be described as 'forward projecting' the path of travel of the proton 201PR. The corresponding energy loss of the proton 201PR is calculated from the residual energy (the energy of the proton 201PR) as determined by means of the range telescope 370 and a knowledge of the energy of the proton 201PR entering the first beam tracker structure 210. In the present embodiment the energy of a proton 201PR entering the first beam tracker structure 210 is assumed to be substantially equal to that of protons 201PR generated by the source of protons 201PR less the amount of energy absorbed by any structures through which the protons 201PR pass before entering the first beam tracker structure 210.

At step S303 the amount of energy lost by each proton 201PR is converted into a WEPL based on the distance through the range telescope 370 travelled by each proton 201PR. That is, a value of WEPL of the volume of tissue of the subject 201S through which the proton 201PR has passed is determined based on the residual energy of the proton 201PR as determined by reference to data output by the CMOS detector devices 372A of the range telescope 370. By calculating values of WEPL of the subject 201S at different angles of the subject 201 with respect to the proton beam 201B, the WEPL of discrete volumes (voxels) of tissue may be calculated (at steps S305 and S307), allowing a 3D voxel map of the WEPL of tissue to be generated at steps S305 and S307. The advantage of using a water equivalent path length (or equivalent path length in any given reference material) allows the use of only one set of simulations of proton absorption (in the present case, simulations of proton absorption in water) in order to characterise the proton absorption properties of different regions of tissue.

At step S305 a non-linear ray projection algorithm is employed to estimate the most likely path (MLP) of the individual protons 201PR as they pass through the subject 201S based on the knowledge of vectors v1 and v2. Other algorithms or methods may be used in some embodiments to estimate the most likely path. It is to be understood that the WEPL of the MLP determined is stored in memory and used to build up a 3D model of the WEPLs and MLPs of all protons 201PR for which a WEPL and MLP is calculated. An X-Y map (or image) of WEPL of the patient across the 2D X-Y plane is established for each orientation of the subject 201S with respect to the beam 201B. As noted above, in the present embodiment the beam 201B is a 'broad' beam, that is the area of the beam is sufficient to irradiate the region of the subject 201S that is to be imaged without requiring scanning of the beam. In some embodiments, scanning of the beam 201B may be performed in order to allow an area greater than that of the beam area to be imaged.

As the individual protons 201PR follow non-linear paths, at step S305 it is necessary to back project the protons 201PR along their Most Likely Path (MLP) or a suitable approximation to the MLP. Several algorithms are available to perform this operation that employ measurements of a proton's energy and position at a small set of points. This is illustrated in FIG. 36, where for the two identified protons 201PR1, 201PR2, the location (x, y, z) with corresponding energy loss ($E_{loss}$) in the subject 201S is determined for each proton. MLP reconstruction is necessary for both radiographic imaging (2-dimensional) and CT imaging (3-dimensional) in order to obtain optimal spatial resolution.

It is estimated that the average lateral deviation of a MLP path from the true path in the patient should be less than 1 mm in order to provide sufficient resolution to permit treatment of brain tumours.

Finally, at step S307 a method of performing a discrete inverse transform is used to produce a 2-dimensional image I of the subject 201S, in terms of proton stopping power (in the present embodiment, WEPL). In the present embodiment, the apparatus 200 allows a user to select a pixel-size typically between 1 and 5 mm in order to provide a trade-off between noise-suppression and spatial-resolution through software binning of neighbouring pixels to effectively smooth the appearance of the image.

The CT reconstruction is formed from a set of 2-dimensional images acquired at differing relative angles of the proton beam 201B with respect to the subject 201S, the images indicating proton stopping power (determined by reference to the WEPL) as a function of X-Y position. The subject 201S or the beam 201B rotate about a common equicentre (with an axis of rotation perpendicular to the beam axis), with projection images captured typically every 1° up to 180° or up to 360° total rotation. Other angles of rotation between captured images may be useful in some embodiments. Other total angles of rotation may be useful in some embodiments.

The data capture sequence is typically as described above and illustrated with respect to FIG. 31. As described above with respect to FIG. 19, a beam shaper element or compensator 201BS, in the form of a non-uniform beam attenuator, may be placed upstream of the first beam tracker structure 201. The beam shaper element 201BS may be configured to ensure that the energy range of different protons 201PR on the downstream or distal side of the subject 201S remain essentially constant in order to avoid gross variations in energy due to protons that do not interact with the subject at all or pass through the widest parts of the subject. The effect of the beam shaper element 201BS is taken into account in calculations of proton stopping power of the tissue of the subject 201S.

The CT reconstruction calculations generate a cuboid 3-dimensional image built up of voxels, where each voxel value will relate to the proton stopping power of the corresponding volumetric region of tissue of the subject 201S. Several existing algorithms, such as Filtered Back Projection (FBP) are available to undertake the transformation for a set of 2-dimensional projection images to a 3-dimensional data set. In other words, the data in respect of the images of the subject 201S acquired at step S305 are combined to produce a proton CT 3D dataset of voxels, each voxel corresponding to a volume of tissue having a relative stopping power (WEPL) that is calculated during this step.

The 3D dataset generated at step S307 may be employed to generate an image that provides a 2D map of the relative stopping power of tissue at any given cross-sectional location of the subject S201, according to a user's selection. Image I in FIG. 35 is an example of a proton CT image in respect of a particular plane within the subject S201. Darker regions correspond to regions of relatively low stopping power including voids in the subject S201 whilst lighter regions correspond to regions of relatively high stopping power. There are three separate uses that have been identified for such 3D images, namely Treatment Planning, Image-Guidance and Treatment Progression.

As noted above, the position of the Bragg peak can be adjusted by means of an attenuator which absorbs a portion of the energy of a particle. By varying the amount of attenuation in real time, the Bragg peak associated with an otherwise monoenergetic proton beam (exhibiting a relatively sharp Bragg peak) may be effectively widened over a given time period by increasing the range of energies, so that a larger volume of tissue (for example tumour tissue) can be treated. Real-time adjustment of the amount of attenuation can be achieved by movement of a variable thickness attenuator such as by rotation of a wedge-shaped attenuator forming part of a spinning wedge attenuator device. This procedure yields what is commonly termed the Spread-Out Bragg Peak (SOBP)

Figure 37:
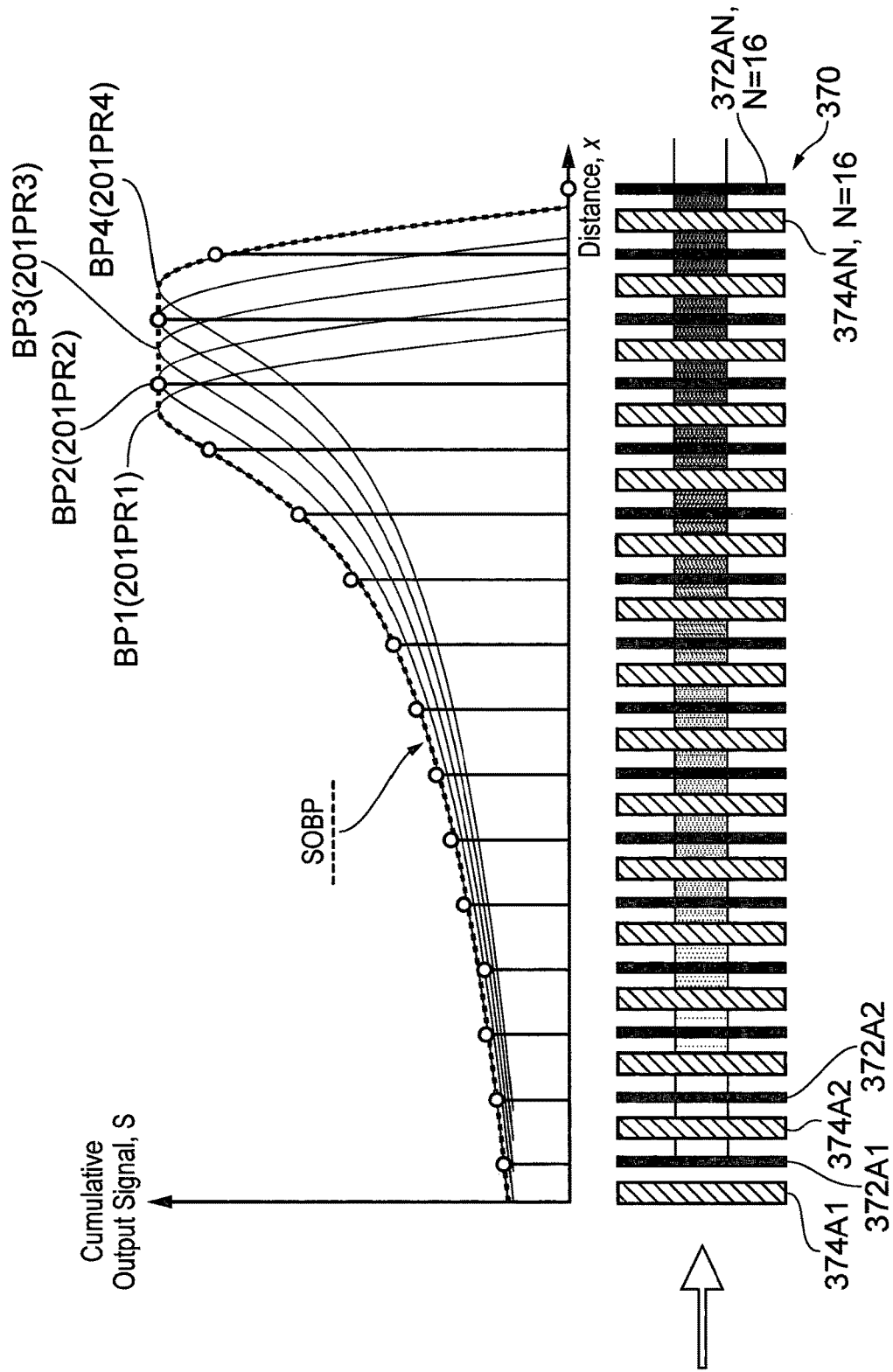
FIG. 37 illustrates the effect of real-time adjustment of the energy of particles upstream of a first beam tracker structure of apparatus in which the range telescope shown in FIG. 37 is installed (being the apparatus of FIG. 4) on the output signals s generated by the range telescope 370; the plot in the upper portion of FIG. 37 is of a value of the sum of output signals s of pixels in respective CMOS detector devices 372A1-N of the range telescope 370 that experience a 'hit' in a particular integration period as a function of distance of the CMOS detector devices 372A1-N from an entrance aperture of the range telescope 370.

FIG. 37 illustrates the effect of real-time adjustment of the energy of particles upstream of the first beam tracker structure 110 on the output signals s generated by the range telescope 370. The plot in the upper portion of FIG. 37 is of a value of the sum of output signals s of pixels in respective CMOS detector devices 372A1-N of the range telescope 370 that experience a 'hit' in a particular integration period as a function of distance of the CMOS detector devices 372A1-N from an entrance aperture of the range telescope 370. In the range telescope 370 illustrated in FIG. 37, N=16.

For the particular data illustrated in FIG. 37, the amount of charge generated in the CMOS detector devices 372A1-N is attributed to the passage of four protons 201PR1, 201PR2, 201PR3, 201PR4 through the range telescope 370. The protons are each of slightly different energy due to the real time adjustment of particle energy by the variable thickness attenuator, the energy of proton 201PR1 being less than that of proton 201PR2, which is in turn less than that of proton 201PR3, which is in turn less than that of proton 201PR4. The expected positions of the respective monoenergetic Bragg peaks in respect of protons 201PR1-4 are labelled BP1-4 in FIG. 37. It can be seen that the cumulative signal s corresponds substantially to the sum of the respective Bragg peaks BP1-4, and may be referred to as a 'spread out Bragg peak' (SOBP).

Some embodiments of the present invention provide a CT scanning apparatus in which proton beam detectors are employed that are based on silicon solid-state detector technologies designed and fabricated using the precision and cost-effective techniques of mainstream microelectronics. Some embodiments of the present invention provide a CT scanning apparatus that can successfully operate in a plurality of different modes as described herein. Such apparatus provides a single system that may perform a range of important functions. Such apparatus may enable a corresponding reduction in maintenance and/or training costs associated with the running of the apparatus, for example in a medical facility. In addition, use of a single system may provide better registration of data from each of its modes of operation, and so reduced error in combining such data.

Some embodiments of the present invention provide:

1. An apparatus for use in the treatment of cancer using beams of charged-particles, wherein such apparatus can be employed, in greatly differing flux conditions, for general quality assurance to ensure the correct operation of the therapy system for treatment, in-treatment monitoring to ensure that treatment is delivered as planned, and in-situ patient imaging for both conventional planar imaging and acquisition of image sets for charged-particle computerised tomography reconstruction. The apparatus contains a plurality of solid-state semiconductor detectors, arranged as two or more x-y positional detectors on either side of the patient undergoing treatment or being imaged, followed by an energy-resolving detector, a range telescope, with x-y positional capability. The apparatus being attached to a computer or computers to control the apparatus for the acquisition of data, storing and processing the data, and providing information, including images and computerised tomography reconstruction.

2. The apparatus of paragraph 1, wherein the charged particles are protons.

3. The detectors of paragraph 1, wherein the detectors are based on silicon semiconductor technology.

4. The detectors of paragraph 3, wherein the detectors are based on strip detectors or CMOS imagers.

5. The positional detectors of paragraph 1, on either side of the patient, can be employed for both high and low beam flux modes.

6. The energy-resolving detector of paragraph 1, on either side of the patient, can be employed for both high and low beam flux modes.
7. The detectors of paragraph 3, wherein these detectors do not perturbate the transmitted particle beam, so as to affect the quality of the beam for treatment or data collection purposes.
8. The positional detectors of paragraph 5 consist of two or more spatial separated planes that record the x-y positional coordinates of individual and identifiable particles.
9. The strip detectors of paragraph 4, where in the individual strips may be split into smaller strips each with an individual readout capability.
10. The strip detectors of paragraph 4, where the individual strips can produce a binary output signifying a hit or an analogue signal which may be further processed.
11. The positional detectors of paragraph 5 consist of two or more closely positioned single-layer strip detectors.
12. The detectors of paragraph 11, wherein they consist of three or more single-layer strip detectors arranged at differing angles to each other.
13. The detectors of paragraph 5, wherein used for quality assurance or in-treatment monitoring (high flux) record a known fraction of the particles passing through each plane.
14. The mode of operation of paragraph 13, wherein the summation of particles for any one strip detector plane is used to construct a histogram profile that can used directly to monitor the position, shape and integrated flux of the particle beam.
15. The profiles of paragraph 14, wherein can be employed to reconstruct the full two-dimensional profile and intensity of the particle beam.
16. The detectors of paragraph 5, wherein their speed of operation is such to record at a number of points the trajectory of a single or a plurality of protons.
17. The energy-resolving detector of paragraph 1, wherein consists of a stack of semiconductor detectors such that it can record the energy profile (residual range) of the particle beam for any of the operational modes.
18. The energy-resolving detector of paragraph 17, wherein its overall energy range of the detector can be adapted by the inclusion of a moderator at its entrance.
19. The energy-resolving detector of paragraph 17, wherein the detectors are a plurality of radiation-hardened CMOS imagers.
20. The energy-detector of paragraph 17, wherein the detectors are a plurality of multiple layer strip detectors.
21. The strip detectors of paragraph 20, wherein the detectors are arranged as of paragraph 12.
22. The CMOS imagers of paragraph 19, wherein each layer of the stack may contain one or more individual CMOS imagers.
23. The energy-resolving detector of paragraph 17, wherein the detectors are interleaved by absorbers to modify in a uniform or non-uniform manner the energy resolution of the overall energy-detector.
24. The detectors of paragraph 17, wherein each detector produces a binary output to register that a particle passed through the detector or lost energy in the detector in coming to rest.
25. The detectors of paragraph 17, wherein each detector produces an analogue or multi-level digital signal to denote that a particle lost energy in the detector in passing through or coming to rest within the detector.
26. The outputs of paragraph 24 are used to produce a profile to determine the energy or energy range of an individual particle or an ensemble of particles, wherein the energy resolution is limited by the effective separation of the detector and absorber layers.
27. The outputs of paragraph 25 are used to produce a profile to determine the energy or energy range of an individual particle or an ensemble of particles, wherein the energy resolution can be refined further by interpolation between the individual detector outputs.
28. The absorbers of paragraph 23, wherein absorbers can possess differing effective thicknesses.
29. For the energy-resolving detector of paragraph 17, wherein an absorber or absorbers at the entrance to this detector are employed limit the range of proton energies entering the detector.
30. The absorbers of paragraph 29, wherein the absorber can prevent any protons entering the detector.
31. The detectors and other components of paragraph 1 are mounted on a rigid frame able to rotate about a fixed patient.
32. The detectors and other components of paragraph 1 are mounted on a fixed rigid frame with a patient able to rotate relative to it.
33. The detectors of paragraph 1, wherein the detectors and associated electronics are synchronised to the period of the source generating the proton beam or some multiple of it.
34. The strip detectors of paragraph 4, wherein output the strip addresses of all strips "hit" within a specified period over several such periods.
35. The strip detectors of paragraph 4, wherein only the addresses of strip "hit" within a given period are output.
36. For the CMOS imagers of paragraph 19, wherein a calibration mask of non-operational or poorly performing pixels and columns, or other array defects, is constructed.
37. For the calibration mask of paragraph 36, wherein this mask is used to identify those regions or pixels of the array to be ignored in subsequent processing.
38. For CMOS imagers of paragraph 19, a series of dark frames is acquired either at the start of each data collection sequence, or at periods during the data collection sequence.
39. For the CMOS operation of paragraph 38, wherein during a series of exposures, during the time when there is relative motion between the patient and the instrument, dark frames are acquired and new
40. For the dark frames of paragraph 38, their average is subtracted from each of the subsequent data frames.
41. The x-y positional detectors on either side of the patient of paragraph 1, by recording the x-y coordinates of an interacting proton or protons it possible to estimate the trajectory of such protons through the instrument and the patient.
42. The trajectory or trajectories of paragraph 41 can be constructed with greater precision through use of curve-fitting algorithm to produce the most likely paths or an approximation to them.
43. For the CMOS detectors of paragraph 4, wherein they are readout in a rolling-shutter mode, either one row or several rows at a time.
44. For the CMOS detectors of paragraph 4, wherein their output data is represented in uncompressed or compressed data formats.
45. For the apparatus of paragraph 1, wherein when it is used quality assurance purposes, all elements of the instrument can be employed.

46. For the apparatus of paragraph 1, wherein when it is used in-treatment monitoring purposes, only the proximal set of strip detectors are employed.
47. For the apparatus of paragraph 1, wherein when it is used for in-situ patient imaging, all elements of the instrument can be employed.
48. For the in-situ patient imaging of paragraph 47, wherein the proton flux is greatly reduced but its energy is increased to ensure that there are distal protons.

Throughout the description of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:
1. A 2D position-sensitive detector assembly, comprising:
   at least three substantially planar detector portions arranged in overlapping relationship as viewed normal to a plane of the detector portions, each detector portion comprising an array of substantially parallel, linear detector elements, the detector elements of respective detector portions being mutually non-parallel, the detector elements each being configured to generate one or more electrical signals in response to interaction of a particle of radiation therewith; and
   a readout circuit portion configured to:
   receive the one or more electrical signals generated by each linear detector element in response to interaction of one or more particles therewith;
   provide an output signal indicative of an identity of each linear detector element in which the one or more electrical signals have been generated;
   receive the electrical signals generated by a predetermined number of linear detector elements in substantially real-time over a predetermined readout period; and
   provide the output signal indicative of the identity of the linear detector elements in which the electrical signal has been generated,
   the readout circuit portion being configured not to process further electrical signals generated by the predetermined number of linear detector elements until the output signal indicative of the identity of the linear detector elements in which the electrical signal has been generated has been provided,
   wherein the readout period corresponds to one pulse period or an integer number of pulse periods greater than one, wherein a pulse period is a repetition period of pulses of radiation generated by a source of radiation.
2. The detector assembly according to claim 1, wherein the linear detector elements of respective detector portions are oriented at substantially equal angles with respect to one another as viewed normal to a plane of the detector portions.
3. The detector assembly according to claim 1, having only three substantially planar detector portions, wherein the linear detector elements of respective detector portions are oriented at substantially 120 degrees with respect to one another.
4. The detector assembly according to claim 1, wherein the detector portions each comprise a plurality of substrates each comprising an array of substantially parallel linear detector elements, respective detector elements of each of the plurality of substrates being substantially parallel and/or substantially collinear.
5. The detector assembly according to claim 1, configured to receive a timing signal indicative of a time at which a source of radiation generates a pulse of radiation.
6. The detector assembly according to claim 1, configured to provide an output indicative of the magnitude of the electrical signal generated in a detector element during a given readout period.
7. A computerized tomography (CT) scanner apparatus comprising the detector assembly according to claim 1.
8. An apparatus comprising:
   a 2D position-sensitive detector assembly, comprising at least three substantially planar detector portions arranged in overlapping relationship as viewed normal to a plane of the detector portions, each detector portion comprising an array of substantially parallel, linear detector elements, the detector elements of respective detector portions being mutually non-parallel, the detector elements each being configured to generate one or more electrical signals in response to interaction of a particle of radiation therewith;
   a first beam tracker structure and a second beam tracker structure, wherein the apparatus is configured to allow passage of radiation through the first and second beam tracker structures, wherein the first and second beam tracker structures each comprise at least one said detector assembly; and
   an energy resolving portion comprising at least one energy resolving portion detector element, the energy resolving portion being configured to measure an energy of particles that have passed through the first and second beam tracker structures.
9. The apparatus according to claim 8, wherein the first and second beam tracker structures each comprise a pair of detector assemblies mutually spaced apart in a direction parallel to a direction of travel of radiation through the apparatus.
10. The apparatus according to claim 8, wherein each detector assembly comprises a readout circuit portion configured to:
   receive the one or more electrical signals generated by each linear detector element in response to interaction of one or more particles therewith, and
   provide an output signal indicative of an identity of each linear detector element in which the one or more electrical signals have been generated,
   wherein the readout circuit portion is configured to:
   receive the electrical signals generated by a predetermined number of linear detector elements in substantially real-time over a predetermined readout period; and
   provide the output signal indicative of the identity of the linear detector elements in which the electrical signal has been generated,
   the readout circuit portion being configured not to process further electrical signals generated by the predetermined number of linear detector elements until the output signal indicative of the identity of the linear detector elements in which the electrical signal has been generated has been provided, wherein the readout period corresponds to one pulse period or an integer number of pulse periods greater than one, wherein a pulse period is a repetition period of pulses of radiation generated by a source of radiation, wherein the apparatus is further configured to synchronise the readout period of the readout circuit portions of each detector assembly of the first and second beam tracker structures such that the readout periods begin at substantially the same time.

11. The apparatus according to claim 8, further configured to determine a direction of travel of individual particles of radiation through each of the beam tracker structures in dependence on detection of a location at which radiation passes through each detector assembly.

12. The apparatus according to claim 8, further configured to:
determine a number of particles of a beam of radiation interacting with each of a plurality of linear detector elements of each detector portion of a detector assembly over a predetermined time period; and
provide an output indicative of a position and shape of the beam of radiation with respect to an active area of each detector portion in dependence on the number of particles interacting with each of said plurality of linear detector elements over the predetermined time period.

13. The apparatus according to claim 12, further configured to provide the output in the form of plots indicative of the number of particles of a beam of radiation that have interacted with each of the plurality of linear detector elements of each respective detector portion of a detector assembly.

14. The apparatus according to claim 8, further configured to measure a location at which a particle interacts with at least one energy resolving portion detector element.

15. The apparatus according to claim 14, further comprising an energy resolving portion readout circuit portion configured to read out a location at which a particle interacts with the at least one energy resolving portion detector element during a readout period.

16. The apparatus according to claim 15, further configured to synchronise the readout period of the readout circuit portions of each detector assembly of the first and second beam tracker structures with the readout period of the energy resolving portion readout circuit portion.

17. A system, comprising:
a 2D position-sensitive detector assembly, comprising at least three substantially planar detector portions arranged in overlapping relationship as viewed normal to a plane of the detector portions, each detector portion comprising an array of substantially parallel, linear detector elements, the detector elements of respective detector portions being mutually non-parallel, the detector elements each being configured to generate one or more electrical signals in response to interaction of a particle of radiation therewith;
a first beam tracker structure and a second beam tracker structure, wherein the apparatus is configured to allow passage of radiation through the first and second beam tracker structures, wherein the first and second beam tracker structures each comprise at least one said detector assembly; and
a generator configured to generate radiation, the system being configured to deliver radiation from the generator to the apparatus, wherein the generator is configured to generate pulses of radiation, the system being configured to synchronize the generation of pulses of radiation by the generator and the readout period of the readout circuit portion via a timing signal such that the readout period includes the period in which electrical signals are generated in the detector assembly in response to the pulses of radiation, and wherein the detector assembly comprises a readout circuit portion configured to:
receive the one or more electrical signals generated by each linear detector element in response to interaction of one or more particles therewith, and
provide an output signal indicative of an identity of each linear detector element in which the one or more electrical signals have been generated,
wherein the readout circuit portion is further configured to:
receive the electrical signals generated by a predetermined number of linear detector elements in substantially real-time over a predetermined readout period; and
provide the output signal indicative of the identity of the linear detector elements in which the electrical signal has been generated, the readout circuit portion being configured not to process further electrical signals generated by the predetermined number of linear detector elements until the output signal indicative of the identity of the linear detector elements in which the electrical signal has been generated has been provided,
wherein the readout period corresponds to one pulse period or an integer number of pulse periods greater than one, wherein a pulse period is a repetition period of pulses of radiation generated by the generator.

18. The system according to claim 17, wherein the generator is configured to generate the timing signal or the apparatus is configured to generate the timing signal.

* * * * *